United States Patent
Holroyd et al.

(10) Patent No.: US 6,576,434 B1
(45) Date of Patent: Jun. 10, 2003

(54) METHODS FOR IDENTIFICATION OF AGENTS WHICH MODULATE CHLORIDE CHANNEL ACTIVITY

(75) Inventors: Kenneth J. Holroyd, Plymouth Meeting, PA (US); Roy C. Levitt, Plymouth Meeting, PA (US); W. Lee Maloy, Plymouth Meeting, PA (US); Jamila Louahed, Plymouth Meeting, PA (US); Mike McLane, Plymouth Meeting, PA (US); Nicholas C. Nicolaides, Plymouth Meeting, PA (US); Yuhong Zhou, Plymouth Meeting, PA (US); Qu Dong, Plymouth Meeting, PA (US)

(73) Assignee: Genaera Corporation, Plymouth Meeting, PA (US)

( * ) Notice: Subject to any disclaimer, the term of this patent is extended or adjusted under 35 U.S.C. 154(b) by 0 days.

(21) Appl. No.: 09/623,624

(22) PCT Filed: Mar. 3, 1999

(86) PCT No.: PCT/US99/04703

§ 371 (c)(1),
(2), (4) Date: Feb. 13, 2001

(87) PCT Pub. No.: WO99/44620

PCT Pub. Date: Sep. 10, 1999

Related U.S. Application Data

(60) Provisional application No. 60/076,815, filed on Mar. 3, 1998.

(51) Int. Cl.$^7$ .................. G01N 33/53; G01N 33/567
(52) U.S. Cl. .................. 435/7.21; 435/7.1; 435/7.2; 435/7.24
(58) Field of Search .................. 435/7.1, 7.2, 7.21, 435/7.24

(56) References Cited

U.S. PATENT DOCUMENTS 5,733,748 A   3/1998  Yu et al.
6,309,857 B1 * 10/2001  Pauli et al. ................ 435/69.1

FOREIGN PATENT DOCUMENTS

WO    WO 96/39419    12/1996

OTHER PUBLICATIONS

Chu et al., Glycophorin A interacts with interleukin–2 and inhibits interleukin–2–dependent T–lymphocyte proliferation, Cell. Immunol. 145:223–239 (1992).
Cunningham et al., SA, Cloning of an epithelial chloride channel from bovine traches, J. Biol. Chem. 270(52):31016–26 (1995).
Dong et al., IL–9 induces chemokine expression in lung epithelial cells and baseline airway eosinophilia in transgenic mice, Eur. J. Immunol. (7):2130–9 (1999).
Doucet et al., Interleukin (IL) 4 and IL–13 act on human lung fibroblasts. Implication in asthma, J. Clin. Invest. 101(10):2129–39 (1998).
Doull et al., Allelic association of gene markers on chromosomes 5q and 11q with atopy and bronchial hyperresponsiveness, Am. J. Respir. Crit. Care Med. 153(4 Pt 1):1280–4 (1996).
Dugas et al, Interleukin–9 potentiates the interleukin–4–induced immunoglobulin (IgG, IgM and IgE) production by normal human B lymphocytes, Eur. J. Immunol. 23:1687–1692 (1993).
Eklund et al., Induction by IL–9 and suppression by IL–3 and IL–4 of the levels of chromosome 14–derived transcripts that encode late–expressed mouse mast cell proteases, J. Immunol. 151:4266–4273 (1993).
Elble RC, Widom J, Gruber AD, Abdel–Ghany M, Levine R, Goodwin A, Cheng HC, Pauli BU. Cloning and characterization of lung–endothelial cell adhesion molecule–1 suggest it is an endothelial chloride channel. J Biol Chem 1997 Oct 31;272(44):27853–61.
Eng et al., Short–term efficacy of ultrasonically nebulized hypertonic saline in cystic fibrosis, *Pediatr. Pulmonol.* 21:77–83 (1996).
Kreitman et al., Site–specific conjugation to interleukin 4 containing mutated cysteine residues produces interleukin 4–toxin conjugates with improved binding and activity, Biochemistry 33(38):11637–44 (1994).
Levitt et al., Emerging therapeutic targets in asthma: a role for interleukin–9, Emerg. Thera. Targets, 3:1–11 (1999).
McLane et al., Interleukin–9 promotes allergen–induced eosinophilic inflammation and airway hyperresponsiveness in transgenic mice, Am. J. Respir. Cell Mol. Biol. 19(5):713–20 (1998).
Nicolaides et al., Interleukin 9: a candidate gene for asthma, Proc. Natl. Acad. Sci. USA, 94(24):13175–80 (1997).
Petit–Frere et al., Interleukin–9 potentoates the interleukin–4–induced IgE and IgG1 release from murine B lymphocytes, Immunology, 79:146–151 (1993).
Temann et al., Expression of interleukin 9 in the lungs of transgenic mice causes airway inflammation, mast cell hyperplasia, and bronchial hyperresponsiveness, J. Exp. Med. 188(7):1307–20 (1998).
Zav'yalov et al., Nonapeptide corresponding to the sequence 27–35 of the mature human IL–2 efficiently competes with RiL–2 for binding to thymocyte receptors [corrected], Immunol Lett. 31(3):285–8 (1992).
International Search Report dated Jul. 9, 1999 from International Application No. PCT/US99/04703, 2 pages.

* cited by examiner

Primary Examiner—Prema Mertz
(74) Attorney, Agent, or Firm—Morgan, Lewis & Bockius LLP

(57) ABSTRACT

A new gene in the calcium-activated chloride channel family has been discovered that is induced by L-9, thereby providing a therapeutic target in IL-9 mediated development of atopic allergy, asthma-related disorders and cystic fibrosis. A method for the identification and use of small molecule inhibitors of this gene and its products to treat these disorders has also been discovered.

32 Claims, 27 Drawing Sheets

FIG. 2A mICACC-1 cDNA Translated Sequence
Sequence Range: 1 to 2931

```
  1                                                 ctgcagg 8 atggaatcttttgaagagtcctgtcttcctcttgatcctccacctt
    M   E   S   L   K   S   P   V   F   L   L   I   L   H   L
 53 ctggaaggagttctgagtgagtccctcatccaactgaacaacaac
    L   E   G   V   L   S   E   S   L   I   Q   L   N   N   N
 98 ggctatgagggcatcgtcatcgccatagaccacgacgtgccggaa
    G   Y   E   G   I   V   I   A   I   D   H   D   V   P   E
143 gatgaagccctcattcaacacataaaggacatggtgactcaggcc
    D   E   A   L   I   Q   H   I   K   D   M   V   T   Q   A
188 tctccatacctgtttgaagctacaggaaaaagatttttacttcaaa
    S   P   Y   L   F   E   A   T   G   K   R   F   Y   F   K
233 aatgttgccattttgattcccgagagctggaaggcaaagcctgaa
    N   V   A   I   L   I   P   E   S   W   K   A   K   P   E
278 tatacgaggccaaaacttgaaaccttcaaaaacgctgatgtcctt
    Y   T   R   P   K   L   E   T   F   K   N   A   D   V   L
323 gtatcaacaaccagccctctaggcaatgatgagccctacaccgaa
    V   S   T   T   S   P   L   G   N   D   E   P   Y   T   E
368 catataggagcatgtggagaaaaggggatcaggattcacctgact
    H   I   G   A   C   G   E   K   G   I   R   I   H   L   T
413 cctgacttcttagcaggaaagaagctgactcagtatgggccacaa
    P   D   F   L   A   G   K   K   L   T   Q   Y   G   P   Q
458 gacaggacctttgtccatgagtgggctcacttccgatggggagtg
    D   R   T   F   V   H   E   W   A   H   F   R   W   G   V
503 tttaatgaatacaacaacgacgagaagttctacttatccaaagga
    F   N   E   Y   N   N   D   E   K   F   Y   L   S   K   G
548 aaaccccaagcagtgaggtgttcagcagccattaccggtaaaaat
    K   P   Q   A   V   R   C   S   A   A   I   T   G   K   N
593 caagttcgtcggtgccagggaggcagttgtatcactaacggaaag
    Q   V   R   R   C   Q   G   G   S   C   I   T   N   G   K
638 tgtgtaatcgacagagtaacgggactgtataaagacaattgtgta
    C   V   I   D   R   V   T   G   L   Y   K   D   N   C   V
683 tttgtaccagatccacaccaaaacgagaaggcttccatcatgttt
    F   V   P   D   P   H   Q   N   E   K   A   S   I   M   F
728 aaccaaaatatcaattctgtggttgaattctgtacagaaaaaaat
    N   Q   N   I   N   S   V   V   E   F   C   T   E   K   N
773 cacaatcaagaagccccaaatgaccaaaaccaacgatgcaatctc
    H   N   Q   E   A   P   N   D   Q   N   Q   R   C   N   L
818 cgaagcacgtgggaagtcatccaggaatctgaggacttcaagcaa
    R   S   T   W   E   V   I   Q   E   S   E   D   F   K   Q
863 accactcccatgacagcccagccacctgcacccaccttctcactg
    T   T   P   M   T   A   Q   P   P   A   P   T   F   S   L
908 ctgcaaattggacaagaattgtgtgcttagttcttgataagtcc
    L   Q   I   G   Q   R   I   V   C   L   V   L   D   K   S
953 gggagcatgctgaacgatgatcgtcttaaccgaatgaatcaggca
    G   S   M   L   N   D   D   R   L   N   R   M   N   Q   A
998 agccggcttttcctgctgcagactgtggagcagggatcctgggtc
    S   R   L   F   L   L   Q   T   V   E   Q   G   S   W   V
```

FIG. 2B

```
1043 gggatggtgacctttgacagtgctgcctatgtacaaagcgaactc
      G  M  V  T  F  D  S  A  A  Y  V  Q  S  E  L
1088 aaacagttaaacagtggtgctgacagagatctgctgatcaagcac
      K  Q  L  N  S  G  A  D  R  D  L  L  I  K  H
1133 ttacccacagtatctgcaggagggacatctatatgctctggcctt
      L  P  T  V  S  A  G  G  T  S  I  C  S  G  L
1178 cggacagcatttacagtgataaagaagaagtatccaactgatgga
      R  T  A  F  T  V  I  K  K  K  Y  P  T  D  G
1223 tctgaaattgtgctgctgaccgatggggaggacaacaccattagc
      S  E  I  V  L  L  T  D  G  E  D  N  T  I  S
1268 agctgctttgacctggtgaagcagagcggggccatcatccataca
      S  C  F  D  L  V  K  Q  S  G  A  I  I  H  T
1313 gtggccctgggaccggctgccgctaaagagcttgagcagctgtcc
      V  A  L  G  P  A  A  A  K  E  L  E  Q  L  S
1358 aaaatgacaggaggcctgcagacatactcttcggatcaggttcag
      K  M  T  G  G  L  Q  T  Y  S  S  D  Q  V  Q
1403 aacaatggtcttgttgatgctttcgcagcactctcctcaggaaat
      N  N  G  L  V  D  A  F  A  A  L  S  S  G  N
1448 gcggcgatcgctcagcactccatccagctggagagcaggggagtt
      A  A  I  A  Q  H  S  I  Q  L  E  S  R  G  V
1493 aatctccagaataaccaatggatgaatggctcagtgatcgtggac
      N  L  Q  N  N  Q  W  M  N  G  S  V  I  V  D
1538 agctcggtgggcaaggacaccttgtttcttatcacctggacaacg
      S  S  V  G  K  D  T  L  F  L  I  T  W  T  T
1583 catcctcctacaatatttatctgggatcccagcggagtggaacaa
      H  P  P  T  I  F  I  W  D  P  S  G  V  E  Q
1628 aatggttttatactagacacaaccactaaggtggcctacctccaa
      N  G  F  I  L  D  T  T  T  K  V  A  Y  L  Q
1673 gtcccaggcacggctaaggttggcttttggaaatacagcattcaa
      V  P  G  T  A  K  V  G  F  W  K  Y  S  I  Q
1718 gcgagctcacagactctcaccttgactgtcacctcccgtgcagca
      A  S  S  Q  T  L  T  L  T  V  T  S  R  A  A
1763 agtgctacactgcctcctattacagtgaccccggtagtgaataag
      S  A  T  L  P  P  I  T  V  T  P  V  V  N  K
1808 aacacagggaaattccccagccctgtaacagtgtatgcaagcatt
      N  T  G  K  F  P  S  P  V  T  V  Y  A  S  I
1853 cgccaaggagcctcgcctattctcagggccagcgtcacagccttg
      R  Q  G  A  S  P  I  L  R  A  S  V  T  A  L
1898 attgaatctgtgaatggaaaaacagtaaccctggaattactggat
      I  E  S  V  N  G  K  T  V  T  L  E  L  L  D
1943 aacggagcaggtgccgatgccaccaagaatgatggtgtctactca
      N  G  A  G  A  D  A  T  K  N  D  G  V  Y  S
1988 aggttttttacagcttttgatgcaaatggtagatacagcgttaaa
      R  F  F  T  A  F  D  A  N  G  R  Y  S  V  K
2033 atatgggctctggaggagtcacttcagacagacagagagcagca
      I  W  A  L  G  G  V  T  S  D  R  Q  R  A  A
2078 cctccgaagaacagagccatgtacatagatggctggattgaggat
      P  P  K  N  R  A  M  Y  I  D  G  W  I  E  D
2123 ggtgaagtaagaatgaacccaccacgtcctgaaactagttatgtt
      G  E  V  R  M  N  P  P  R  P  E  T  S  Y  V
```

FIG. 2C

```
2168 caagacaagcagctgtgcttcagcaggacatcttcaggggatcg
      Q   D   K   Q   L   C   F   S   R   T   S   S   G   G   S
2213 tttgtggccaccaatgtccccgcagcagctcccattcctgacctc
      F   V   A   T   N   V   P   A   A   A   P   I   P   D   L
2258 tttccaccctgtcaaatcactgacctgaaggccagcatccaaggg
      F   P   P   C   Q   I   T   D   L   K   A   S   I   Q   G
2303 cagaacctggtgaatctgacgtggacggctcctggggatgactac
      Q   N   L   V   N   L   T   W   T   A   P   G   D   D   Y
2348 gaccacgggagagcttccaactacatcatccgaatgagcaccagt
      D   H   G   R   A   S   N   Y   I   I   R   M   S   T   S
2393 atcgttgatctcagggaccacttcaacacctcactccaagtgaac
      I   V   D   L   R   D   H   F   N   T   S   L   Q   V   N
2438 actaccggtcttatccccaaagaggccagctctgaggaaatcttt
      T   T   G   L   I   P   K   E   A   S   S   E   E   I   F
2483 gagtttgaactgggaggcaacacttttggaaatggcacagatatc
      E   F   E   L   G   G   N   T   F   G   N   G   T   D   I
2528 ttcattgctatccaggctgtggataagtccaatctgaaatcagaa
      F   I   A   I   Q   A   V   D   K   S   N   L   K   S   E
2573 atctccaacattgcacgggtgtctgtgttcatccccgctcaggag
      I   S   N   I   A   R   V   S   V   F   I   P   A   Q   E
2618 ccgcccattcccgaagactcaactccccctttgtcctgacatcagc
      P   P   I   P   E   D   S   T   P   P   C   P   D   I   S
2663 atcaacagcaccattcctggcatccacgtgctgaagataatgtgg
      I   N   S   T   I   P   G   I   H   V   L   K   I   M   W
2708 aagtggctaggggaaatgcaggtgacactaggtttgcactga
      K   W   L   G   E   M   Q   V   T   L   G   L   H   *

2750 attttcaggcaagaaatcaaccagtcattcctttcactggagaat 2795 tttctaaaaatgtactttagacttcctgtaggggggcggtatagta 2840 acactcgaagctgtaaaactgggtctgggtgcattaaaaattatc 2885 tgttcaaatacaaaaaaaaaaaaaaaaaaaaaaaaaaaaaaaaaa 2930 aa
```

FIG. 3A

CLUSTAL W (1.82) sequence alignment of mICACC-1 and bovine CACC (b-CACC)

```
mICACC-1: MESLKSPVFLLILHLLEGVLSESLIQLNNNGYEGIVIAIDHDVPEDEALIQHIKDMVTQA 60
b-CACC:   MVPRLTVILFLTLHLLPG-MKSSMVNLINNGYDGIVIAINPSVPEDEKLIQNIKEMVTEA 59 mICACC-1: SPYLFEATGKRFYFKNVAILIPESWKAKPEYTRPKLETFKNADVLVSTTSPLGNDEPYTE 120
b-CACC:   STYLFHATKRRVYFRNVSILIPMTWKSKSEYLMPKQESYDQAEVIVANPYLKHGDDPYTL 119 mICACC-1: HIGACGEKGIRIHLTPDFLAGKKLTQYGPQDRTFVHEWAHFRWGVFNEYNNDEKFYLSK- 179
b-CACC:   QYGRCGEKGQYIHFTPNFLLTNNLPIYGSRGRAFVHEWAHLRWGIFDEYNGDQPFYISRR 179 mICACC-1: GKPQAVRCSAAITGKNQVRRCQGGSCITNGKCVIDRVTGLYKDNCVFVPDPHQNEKASIM 239
b-CACC:   NTIEATRCSTHITGTNVIVKCQGGSCITR-PCRRDSQTGLYEAKCTFIPEKSQTARESIM 238 mICACC-1: FNQNINSVVEFCTEKNHNQEAPNDQNQRCNLRSTWEVIQESEDFKQTTPMTAQPP--APT 297
b-CACC:   FMQSLHSVTEFCTEKTHNVEAPNLQNKMCNGKSTWDVIMNSTDFQNTSPMTEMNPPTQPT 298 mICACC-1: FSLLQIGQRIVCLVLDKSGSMLNDDRLNRMNQASRLFLLQTVEQGSWVGMVTFDSAAYVQ 357
b-CACC:   FSLLKSKQRVVCLVLDKSGSMSSEDRLFRMNQAAELFLIQIIEKGSLVGMVTFDSVAEIR 358 mICACC-1: SELKQLNSGADRDLLIKHLPTVSAGGTSICSGLRTAFT-VIKKKYPTDGSEIVLLTDGED 416
b-CACC:   NNLTKITDDNVYENITANLPQEANGGTSICRGLKAGFQAIIQSQQSTSGSEIILLTDGED 418 mICACC-1: NTISSCFDLVKQSGAIIHTVALGPAAAKELEQLSKMTGGLQTYSSDQVQNNGLVDAFAAL 476
b-CACC:   NEIHSCIEEVKQSGVIIHTIALGPSAAKELETLSDMTGGHRFYANKDIN--GLTNAFSRI 476 mICACC-1: SSGNAAIAQHSIQLESRGVNLQNNQWMNGSVIVDSSVGKDTLFLITWTTHPPTIFIWDPS 536
b-CACC:   SSRSGSITQQTIQLESKALAITEKKWVNGTVPVDSTIGNDTFFVVTWTIKKPEILLQDPK 536 mICACC-1: G--VEQNGFILDTT-TKVAYLQVPGTAKVGFWKYSIQ---ASSQTLTLTVTSRAASATLP 590
b-CACC:   GKKYKTSDFKEDKLNIHSARLRIPGIAETGTWTYSLLNNHASPQILTVTVTTRARSPTTP 596 mICACC-1: PITVTPVVNKNTGKFPSPVTVYASIRQGASPILRASVTALIESVNGKTVTLELLDNGAGA 650
b-CACC:   PVTATAHMSQNTAHYPSPVIVYAQVSQGFLPVLGINVTAIIETEDGHQVTLELWDNGAGA 656 mICACC-1: DATKNDGVYSRFFTAFDANGRYSVKIWALGGVTSDRQRAAPPKNRAMYIDGWIEDGEVRM 710
b-CACC:   DTVKNDGIYSRYFTDYRGNGRYSLKVHAEARNNTARLSLRQPQNKALYIPGYIENGKIIL 716 mICACC-1: NPPRPETS--YVQDKQLCFSRTSSGGSFVATNVPAAAPIPDLFPPCQITDLKASIQGQNL 768
b-CACC:   NPPRPEVKDDLAKAEIEDFSRLTSGGSFTVSGAPPGN-HPSVLPPNKIIDLEAKFK-EDH 774
```

FIG. 3B

```
mICACC-1:  VNLTWTAPGDDYDHGRASNYIIRMSTSIVDLRDHFNTSLQVNTTGLIPKEASSEEIFEFE  828
b-CACC:    IQLSWTAPANVLDKGKANSYIIRISKSFLDLQKDFDNATLVNTSSLKPKEAGSDENFEFK  834 mICACC-1:  LGGNTFGNGTDIFIAIQAVDKSNLKSEISNIARVSVFIPAQEPPIPEDSTPPCPDISINS  888
b-CACC:    PEPFRIENGTNFYIAVQAINEANLTSEVSNIAQAIKFIP-----MPEDSVP-ALGTKISA  888 mICACC-1:  TIPGIHVLKIMWKWLGEMQVTLGLH  913
b-CACC:    INLAIFALAMILSIV----------  903
``` hICACC-2 Translated Sequence
Sequence Range: 1 to 3190

FIG. 4A1

```
   1                         cttcttgtgttcttaaacccttgcaagtt 30 cagraagaaacccatctgcatccatattgaaaacctgacacaatg 75 tatgcagcaggctcagtgtgagtgaactggaggcttctctacaac 120 atgacccaaaggagcattgcaggtcctatttgcaacctgaagttt
     M  T  Q  R  S  I  A  G  P  I  C  N  L  K  F
 165 gtgactctcctggttgccttaagttcagaactcccattcctggga
     V  T  L  L  V  A  L  S  S  E  L  P  F  L  G
 210 gctggagtacagcttcaagacaatgggtataatggattgctcatt
     A  G  V  Q  L  Q  D  N  G  Y  N  G  L  L  I
 255 gcaattaatcctcaggtacctgagaatcagaacctcatctcaaac
     A  I  N  P  Q  V  P  E  N  Q  N  L  I  S  N
 300 attaaggaaatgataactgaagcttcattttacctatttaatgct
     I  K  E  M  I  T  E  A  S  F  Y  L  F  N  A
 345 accaagagaagagtattttcagaaatataaagattttaatacct
     T  K  R  R  V  F  F  R  N  I  K  I  L  I  P
 390 gccacatggaaagctaataataacagcaaaataaaacaagaatca
     A  T  W  K  A  N  N  N  S  K  I  K  Q  E  S
 435 tatgaaaaggcaaatgtcatagtgactgactggtatagggcacat
     Y  E  K  A  N  V  I  V  T  D  W  Y  R  A  H
 480 ggagatgatccatacaccctacaatacagagggtgtggaaaagag
     G  D  D  P  Y  T  L  Q  Y  R  G  C  G  K  E
 525 ggaaaatacattcatttcacacctaatttcctactgaatgataac
     G  K  Y  I  H  F  T  P  N  F  L  L  N  D  N
 570 ttaacagctggctacggatcacgaggccgagtgtttgtccatgaa
     L  T  A  G  Y  G  S  R  G  R  V  F  V  H  E
 615 tgggcccacctccgttggggtgtgttcgatgagtataacaatgac
     W  A  H  L  R  W  G  V  F  D  E  Y  N  N  D
 660 aaaccttctacataaatgggcaaaatcaaattaaagtgacaagg
     K  P  F  Y  I  N  G  Q  N  Q  I  K  V  T  R
 705 tgttcatctgacatcacaggcattttgtgtgtgaaaaaggtcct
     C  S  S  D  I  T  G  I  F  V  C  E  K  G  P
 750 tgcccccaagaaaactgtattattagtaagcttttaaagaagga
     C  P  Q  E  N  C  I  I  S  K  L  F  K  E  G
 795 tgcacctttatctacaatagcacccaaagtgcaactgcatcaata
     C  T  F  I  Y  N  S  T  Q  S  A  T  A  S  I
 840 atgttcatgcgaagtttatcttctgtggttgaattttgtaatgca
     M  F  M  R  S  L  S  S  V  V  E  F  C  N  A
 885 agtacccacaaccaagaagcaccaaacctacagaaccagatgtgc
     S  T  H  N  Q  E  A  P  N  L  Q  N  Q  M  C
 930 agcctcagaagtgcatgggatgtaatcacagactctgctgactttn
     S  L  R  S  A  W  D  V  I  T  D  S  A  D  F
 975 caccacagctttcccatgaacgggactgagcttccacctcctccc
     H  H  S  F  P  M  N  G  T  E  L  P  P  P  P
1020 acattctcgcttgtagaggctggtgacaaagtggtctgtttagtg
     T  F  S  L  V  E  A  G  D  K  V  V  C  L  V
```

FIG. 4A2

```
1065 ctggatgcgtccagcaagatggcagaggctgacagactccttcaa
      L   D   A   S   S   K   M   A   E   A   D   R   L   L   Q
1110 ctacaacaagccgcagaatttatttgatgcagattgttgaaatt
      L   Q   Q   A   A   E   F   Y   L   M   Q   I   V   E   I
1155 cataccttcgtgggcattgccagtttcgacagcaaaggagagatc
      H   T   F   V   G   I   A   S   F   D   S   K   G   E   I
1200 agagcccagctacaccaaattaacagcaatgatgatcgaaagttg
      R   A   Q   L   H   Q   I   N   S   N   D   D   R   K   L
1245 ctggtttcatatctgcccaccactgtatcagctaaaacagacatc
      L   V   S   Y   L   P   T   T   V   S   A   K   T   D   I
1290 agcatttgttcagggcttaagaaaggatttgaggtggttgaaaaa
      S   I   C   S   G   L   K   K   G   F   E   V   V   E   K
1335 ctgaatggaaaagcttatggctctgtgatgatattagtgaccagc
      L   N   G   K   A   Y   G   S   V   M   I   L   V   T   S
1380 ggagatgataagcttcttggcaattgcttacccactgtgctcagc
      G   D   D   K   L   L   G   N   C   L   P   T   V   L   S
1425 agtggttcaacaattcactccattgccctgggttcatctgcagcc
      S   G   S   T   I   H   S   I   A   L   G   S   S   A   A
1470 ccaaatctggaggaattatcacgtcttacaggaggtttaaagttc
      P   N   L   E   E   L   S   R   L   T   G   G   L   K   F
1515 tttgttccagatatatcaaactccaatagcatgattgatgctttc
      F   V   P   D   I   S   N   S   N   S   M   I   D   A   F
1560 agtagaatttcctctggaactggagacatttccagcaacatatt
      S   R   I   S   S   G   T   G   D   I   F   Q   Q   H   I
1605 cagcttgaaagtacaggtgaaaatgtcaaacctcaccatcaattg
      Q   L   E   S   T   G   E   N   V   K   P   H   H   Q   L
1650 aaaaacacagtgactgtggataatactgtgggcaacgacactatg
      K   N   T   V   T   V   D   N   T   V   G   N   D   T   M
1695 tttctagttacgtggcaggccagtggtcctcctgagattatatta
      F   L   V   T   W   Q   A   S   G   P   P   E   I   I   L
1740 tttgatcctgatggacgaaaatactacacaaataatttttatcacc
      F   D   P   D   G   R   K   Y   Y   T   N   N   F   I   T
1785 aatctaacttttcggacagctagtctttggattccaggaacagct
      N   L   T   F   R   T   A   S   L   W   I   P   G   T   A
1830 aagcctgggcactggacttacacccctgaacaatacccatcattct
      K   P   G   H   W   T   Y   T   L   N   N   T   H   H   S
1875 ctgcaagccctgaaagtgacagtgacctctcgtgcctccaactca
      L   Q   A   L   K   V   T   V   T   S   R   A   S   N   S
1920 gctgtgcccccagccactgtggaagcctttgtggaaagagacagc
      A   V   P   P   A   T   V   E   A   F   V   E   R   D   S
1965 ctccatttcctcatcctgtgatgatttatgccaatgtgaaacag
      L   H   F   P   H   P   V   M   I   Y   A   N   V   K   Q
2010 ggattttatcccattcttaatgccactgtcactgccacagttgag
      G   F   Y   P   I   L   N   A   T   V   T   A   T   V   E
2055 ccagagactggagatcctgttacgctgagactccttgatgatgga
      P   E   T   G   D   P   V   T   L   R   L   L   D   D   G
2100 gcaggtgctgatgttataaaaaatgatggaatttactcgaggtat
      A   G   A   D   V   I   K   N   D   G   I   Y   S   R   Y
2145 ttttctcctttgctgcaaatggtagatatagcttgaaagtgcat
      F   F   S   F   A   A   N   G   R   Y   S   L   K   V   H
```

FIG. 4A3

```
2190 gtcaatcactctcccagcataagcaccccagcccactctattcca
      V  N  H  S  P  S  I  S  T  P  A  H  S  I  P
2235 gggagtcatgctatgtatgtaccaggttacacagcaaacggtaat
      G  S  H  A  M  Y  V  P  G  Y  T  A  N  G  N
2280 attcagatgaatgctccaaggaaatcagtaggcagaaatgaggag
      I  Q  M  N  A  P  R  K  S  V  G  R  N  E  E
2325 gagcgaaagtggggctttagccgagtcagctcaggaggctccttt
      E  R  K  W  G  F  S  R  V  S  S  G  G  S  F
2370 tcagtgctgggagttccagctggcccccaccctgatgtgtttcca
      S  V  L  G  V  P  A  G  P  H  P  D  V  F  P
2415 ccatgcaaaattattgacctggaagctgtaaaagtagaagaggaa
      P  C  K  I  I  D  L  E  A  V  K  V  E  E  E
2460 ttgaccctatcttggacagcacctggagaagactttgatcaggc
      L  T  L  S  W  T  A  P  G  E  D  F  D  Q  G
2505 caggctacaagctatgaaataagaatgagtaaaagtctacagaat
      Q  A  T  S  Y  E  I  R  M  S  K  S  L  Q  N
2550 atccaagatgactttaacaatgctatttagtaaatacatcaaag
      I  Q  D  D  F  N  N  A  I  L  V  N  T  S  K
2595 cgaaatcctcagcaagctggcatcagggagatatttacgttctca
      R  N  P  Q  Q  A  G  I  R  E  I  F  T  F  S
2640 ccccagatttccacgaatggacctgaacatcagccaaatggagaa
      P  Q  I  S  T  N  G  P  E  H  Q  P  N  G  E
2685 acacatgaaagccacagaatttatgttgcaatacgagcaatggat
      T  H  E  S  H  R  I  Y  V  A  I  R  A  M  D
2730 aggaactccttacagtctgctgtatctaacattgcccaggcgcct
      R  N  S  L  Q  S  A  V  S  N  I  A  Q  A  P
2775 ctgtttattccccccaattctgatcctgtacctgccagagattat
      L  F  I  P  P  N  S  D  P  V  P  A  R  D  Y
2820 cttatattgaaaggagttttaacagcaatgggtttgataggaatc
      L  I  L  K  G  V  L  T  A  M  G  L  I  G  I
2865 atttgccttattatagttgtgacacatcatactttaagcaggaaa
      I  C  L  I  I  V  V  T  H  H  T  L  S  R  K
2910 aagagagcagacaagaaagagaatggaacaaaattattataa
      K  R  A  D  K  K  E  N  G  T  K  L  L  *

2952 ataaatatccaaagtgtcttccttcttagatataagacccatggc 2997 cttcgactacaaaaacatactaacaaagtcaaattaacatcaaaa 3042 ctgtattaaaatgcattgagttttgtacaatacagataagatttt 3087 tacatggtagatcaacaaattcttttgggggtagattagaaaac 3132 cttcactttggctatgaacaaataataaaaattattctttaaaa 3177 aaaaaaaaaaaaaa 3190
``` hICACC-1 FIG. 4B1

Sequence Range: 1 to 2745

```
   1 atggggccatttaagagttctgtgttcaccttgattcttcaccctt
     M  G  P  F  K  S  S  V  F  T  L  I  L  H  L
  46 ctagaaggggccctgagtaattcactcattcagctgaacaacaat
     L  E  G  A  L  S  N  S  L  I  Q  L  N  N  N
  91 ggctatgaaggcattgtcgttgcaatcgaccccaatgtgccagaa
     G  Y  E  G  I  V  V  A  I  D  P  N  V  P  E
 136 gatgaaacactcattcaacaaataaaggacatggtgacccaggca
     D  E  T  L  I  Q  Q  I  K  D  M  V  T  Q  A
 181 tctctgtatctgtttgaagctacaggaaagcgatttttatttcaaa
     S  L  Y  L  F  E  A  T  G  K  R  F  Y  F  K
 226 aatgttgccatttttgattcctgaaacatggaagacaaaggctgac
     N  V  A  I  L  I  P  E  T  W  K  T  A  D
 271 tatgtgagaccaaaacttgagacctacaaaaatgctgatgttctg
     Y  V  R  P  K  L  E  T  Y  K  N  A  D  V  L
 316 gttgctgagtctactcctccaggtaatgatgaacccctacactgag
     V  A  E  S  T  P  P  G  N  D  E  P  Y  T  E
 361 cagatgggcaactgtggagagaagggtgaaaggatccacctcact
     Q  M  G  N  C  G  E  K  G  E  R  I  H  L  T
 406 cctgatttcattgcaggaaaaaagttagctgaatatggaccacaa
     P  D  F  I  A  G  K  K  L  A  E  Y  G  P  Q
 451 ggtagggcatttgtccatgagtgggctcatctacgatggggagta
     G  R  A  F  V  H  E  W  A  H  L  R  W  G  V
 496 tttgacgagtacaataatgatgagaaattctacttatccaatgga
     F  D  E  Y  N  N  D  E  K  F  Y  L  S  N  G
 541 agaatacaagcagtaagatgttcagcaggtattactggtacaaat
     R  I  Q  A  V  R  C  S  A  G  I  T  G  T  N
 586 gtagtaaagaagtgtcagggaggcagctgttacaccaaaagatgc
     V  V  K  K  C  Q  G  G  S  C  Y  T  K  R  C
 631 acattcaataaagtwacaggactctatgaaaaaggatgtgagttt
     T  F  N  K  V  T  G  L  Y  E  K  G  C  E  F
 676 gttctccaatcccgccagacggagaaggcttctataatgtttgca
     V  L  Q  S  R  Q  T  E  K  A  S  I  M  F  A
 721 caacatgttgattctatagttgaattctgtacagaacaaaaccac
     Q  H  V  D  S  I  V  E  F  C  T  E  Q  N  H
 766 aacaaagaagctccaaacaagcaaaatcaaaaatgcaatctccga
     N  K  E  A  P  N  K  Q  N  Q  K  C  N  L  R
 811 agcacatgggaagtgatccgtgattctgaggactttaagaaaacc
     S  T  W  E  V  I  R  D  S  E  D  F  K  K  T
 856 actcctatgacaacacagccaccaaatcccaccttctcattgctg
     T  P  M  T  T  Q  P  P  N  P  T  F  S  L  L
 901 cagattggacaaagaattgtgtgtttagtccttgacaaatctgga
     Q  I  G  Q  R  I  V  C  L  V  L  D  K  S  G
 946 agcatggcgactggtaaccgcctcaatcgactgaatcaagcaggc
     S  M  A  T  G  N  R  L  N  R  L  N  Q  A  G
 991 cagcttttcctgctgcagacagttgagctggggtcctgggttggg
     Q  L  F  L  L  Q  T  V  E  L  G  S  W  V  G
1036 atggtgacatttgacagtgctgcccatgtacaaagtgaactcata
     M  V  T  F  D  S  A  A  H  V  Q  S  E  L  I
1081 cagataaacagtggcagtgacagggacacactcgccaaaagatta
     Q  I  N  S  G  S  D  R  D  T  L  A  K  R  L
1126 cctgcagcagcttcaggagggacgtccatctgcagcgggcttcga
     P  A  A  A  S  G  G  T  S  I  C  S  G  L  R
```

FIG. 4B2

```
1171 tcggcatttactgtgattaggaagaaatatccaactgatggatct
     S  A  F  T  V  I  R  K  K  Y  P  T  D  G  S
1216 gaaattgtgctgctgacggatggggaagacaacactataagtggg
     E  I  V  L  L  T  D  G  E  D  N  T  I  S  G
1261 tgctttaacgaggtcaaacaaagtggtgccatcatccacacagtc
     C  F  N  E  V  K  Q  S  G  A  I  I  H  T  V
1306 gctttggggccctctgcagctcaagaactagaggagctgtccaaa
     A  L  G  P  S  A  A  Q  E  L  E  E  L  S  K
1351 atgacaggaggtttacagacatatgcttcagatcaagttcagaac
     M  T  G  G  L  Q  T  Y  A  S  D  Q  V  Q  N
1396 aatggcctcattgatgcttttggggcccttttcatcaggaaatgga
     N  G  L  I  D  A  F  G  A  L  S  S  G  N  G
1441 gctgtctctcagcgctccatccagcttgagagtaagggattaacc
     A  V  S  Q  R  S  I  Q  L  E  S  K  G  L  T
1486 ctccagaacagccagtggatgaatggcacagtgatcgtggacagc
     L  Q  N  S  Q  W  M  N  G  T  V  I  V  D  S
1531 accgtgggaaaggacactttgtttcttatcacctggacaacgcag
     T  V  G  K  D  T  L  F  L  I  T  W  T  T  Q
1576 cctccccaaatccttctctgggatcccagtggacagaagcaaggt
     P  P  Q  I  L  L  W  D  P  S  G  Q  K  Q  G
1621 ggctttgtagtggacaaaaacaccaaaatggcctacctccaaatc
     G  F  V  V  D  K  N  T  K  M  A  Y  L  Q  I
1666 ccaggcattgctaaggttggcacttggaaatacagtctgcaagca
     P  G  I  A  K  V  G  T  W  K  Y  S  L  Q  A
1711 agctcacaaaccttgaccctgactgtcacgtcccgtgcgtccaat
     S  S  Q  T  L  T  L  T  V  T  S  R  A  S  N
1756 gctaccctgcctccaattacagtgacttccaaaacgaacaaggac
     A  T  L  P  P  I  T  V  T  S  K  T  N  K  D
1801 accagcaaattccccagccctctggtagtttatgcaaatattcgc
     T  S  K  F  P  S  P  L  V  V  Y  A  N  I  R
1846 caaggagcctccccaattctcagggccagtgtcacagccctgatt
     Q  G  A  S  P  I  L  R  A  S  V  T  A  L  I
1891 gaatcagtgaatggaaaaacagttaccttggaactactggataat
     E  S  V  N  G  K  T  V  T  L  E  L  L  D  N
1936 ggagcaggtgctgatgctactaaggatgacggtgtctactcaagg
     G  A  G  A  D  A  T  K  D  D  G  V  Y  S  R
1981 tatttcacaacttatgacacgaatggtagatacagtgtaaaagtg
     Y  F  T  T  Y  D  T  N  G  R  Y  S  V  K  V
2026 cgggctctgggaggagttaacgcagccagacggagagtgataccc
     R  A  L  G  G  V  N  A  A  R  R  R  V  I  P
2071 cagcagagtggagcactgtacatacctggctggattgagaatgat
     Q  Q  S  G  A  L  Y  I  P  G  W  I  E  N  D
2116 gaaatccaatggaatccaccaagacctgaaattaataaggatgat
     E  I  Q  W  N  P  P  R  P  E  I  N  K  D  D
2161 gttcaacacaagcaagtgtgtttcagcagaacatcctcgggaggc
     V  Q  H  K  Q  V  C  F  S  R  T  S  S  G  G
2206 tcatttgtggcttctgatgtcccaaatgctcccatacctgatctc
     S  F  V  A  S  D  V  P  N  A  P  I  P  D  L
2251 ttcccacctggccaaatcaccgacctgaaggcggaaattcacggg
     F  P  P  G  Q  I  T  D  L  K  A  E  I  H  G
2296 ggcagtctcattaatctgacttggacagctcctggggatgattat
     G  S  L  I  N  L  T  W  T  A  P  G  D  D  Y
2341 gaccatggaacagctcacaagtatatcattcgaataagtacaagt
     D  H  G  T  A  H  K  Y  I  I  R  I  S  T  S
```

FIG. 4B3

```
2386 attcttgatctcagagacaagttcaatgaatctcttcaagtgaat
      I  L  D  L  R  D  K  F  N  E  S  L  Q  V  N
2431 actactgctctcatcccaaaggaagccaactctgaggaagtcttt
      T  T  A  L  I  P  K  E  A  N  S  E  E  V  F
2476 ttgtttaaaccagaaaacattacttttgaaaatggcacagatctt
      L  F  K  P  E  N  I  T  F  E  N  G  T  D  L
2521 ttcattgctattcaggctgttgataaggtcgatctgaaatcagaa
      F  I  A  I  Q  A  V  D  K  V  D  L  K  S  E
2566 atatccaacattgcacgagtatctttgtttattcctccacagact
      I  S  N  I  A  R  V  S  L  F  I  P  P  Q  T
2611 ccgccagagacacctagtcctgatgaaacgtctgctccttgtcct
      P  P  E  T  P  S  P  D  E  T  S  A  P  C  P
2656 aatattcatatcaacagcaccattcctggcattcacattttaaaa
      N  I  H  I  N  S  T  I  P  G  I  H  I  L  K
2701 attatgtggaagtggataggagaactgcagctgtcaatagcctag 2745
      I  M  W  K  W  I  G  E  L  Q  L  S  I  A  *
```

FIG. 5A

CLUSTAL W (1.82) multiple sequence alignment of mouse and human ICACC proteins

```
mICACC-1:   --MESLKSPVFLLILHLLEGVLSESL------IQLNNNGYEGIVIAIDHDVPEDEALIQH  52
hICACC-1:   --MGPFKSSVFILILHLLEGALSNSL------IQLNNNGYEGIVVAIDPNVPEDETLIQQ  52
hICACC-2:   MTQRSIAGPICNLKFVTLLVALSSELPFLGAGVQLQDNGYNGLLIAINPQVPENQNLISN  60 mICACC-1:   IKDMVTQASPYLFEATGKRFYFKNVAILIPESWKAKPEYTRPKLETFKNADVLVSTTSPL 112
hICACC-1:   IKDMVTQASLYLFEATGKRFYFKNVAILIPETWKTKADYVRPKLETYKNADVLVAESTPP 112
hICACC-2:   IKEMITEASFYLFNATKRRVFFRNIKILIPATWKAN-NNSKIKQESYEKANVIVTDWYRA 119 mICACC-1:   GNDEPYTEHIGACGEKGIRIHLTPDFLAGKKLTQ-YGPQDRTFVHEWAHFRWGVFNEYNN 171
hICACC-1:   GNDEPYTEQMGNCGEKGERIHLTPDFIAGKKLAE-YGPQGRAFVHEWAHLRWGVFDEYNN 171
hICACC-2:   HGDDPYTLQYRGCGKEGKYIHFTPNFLLNDNLTAGYGSRGRVFVHEWAHLRWGVFDEYNN 179 mICACC-1:   DEKFYLS-KGKPQAVRCSAAITGKNQVRRCQGGSCITNGKCVIDRVTGLYKDNCVFVPDP 230
hICACC-1:   DEKFYLS-NGRIQAVRCSAGITGTNVVKKCQGGSCYTK-RCTFNKXTGLYEKGCEFVLQS 229
hICACC-2:   DKPFYINGQNQIKVTRCSSDITG---IFVCEKGPCPQE-NCIISK---LFKEGCTFIYNS 232 mICACC-1:   HQNEKASIMFNQNINSVVEFCTEKNHNQEAPNDQNQRCNLRSTWEVIQESEDFKQTTPM- 289
hICACC-1:   RQTEKASIMFAQHVDSIVEFCTEQNHNKEAPNKQNQKCNLRSTWEVIRDSEDFKKTTPM- 288
hICACC-2:   TQSATASIMFMRSLSSVVEFCNASTHNQEAPNLQNQMCSLRSAWDVITDSADFHHSFPMN 292 mICACC-1:   -TAQPPAPTFSLLQIGQRIVCLVLDKSGSMLNDDRLNRMNQASRLFLLQTVEQGSWVGMV 348
hICACC-1:   -TTQPPNPTFSLLQIGQRIVCLVLDKSGSMATGNRLNRLNQAGQLFLLQTVELGSWVGMV 347
hICACC-2:   GTELPPPPTFSLVEAGDKVVCLVLDASSKMAEADRLLQLQQAAEFYLMQIVEIHTFVGIA 352 mICACC-1:   TFDSAAYVQSELKQLNSGADRDLLIKHLPTVSAGGT--SICSGLRTAFTVIKKKY-PTDG 405
hICACC-1:   TFDSAAHVQSELIQINSGSDRDTLAKRLPAAASGGT--SICSGLRSAFTVIRKKY-PTDG 404
hICACC-2:   SFDSKGEIRAQLHQINSNDDRKLLVSYLPTTVSAKTDISICSGLKKGFEVVEKLNGKAYG 412 mICACC-1:   SEIVLLTDGEDNTISSCFDLVKQSGAIIHTVALGPAAAKELEQLSKMTGGLQTYSSDQVQ 465
hICACC-1:   SEIVLLTDGEDNTISGCFNEVKQSGAIIHTVALGPSAAQELEELSKMTGGLQTYASDQVQ 464
hICACC-2:   SVMILVTSGDDKLLGNCLPTVLSSGSTIHSIALGSSAAPNLEELSRLTGGLKFFVPDISN 472 mICACC-1:   NNGLVDAFAALSSGNAAIAQHSIQLESRGVNLQNNQWMNGSVIVDSSVGKDTLFLITWTT 525
hICACC-1:   NNGLIDAFGALSSGNGAVSQRSIQLESKGLTLQNSQWMNGTVIVDSTVGKDTLFLITWTT 524
hICACC-2:   SNSMIDAFSRISSGTGDIFQQHIQLESTGENVKPHHQLKNTVTVDNTVGNDTMFLVTWQA 532 mICACC-1:   H-PPTIFIWDPSGVE--QNGFILDTTTKVAYLQVPGTAKVGFWKYSIQ---ASSQTLTLT 579
hICACC-1:   Q-PPQILLWDPSGQK--QGGFVVDKNTKMAYLQIPGIAKVGTWKYSLQ---ASSQTLTLT 578
hICACC-2:   SGPPEIILFDPDGRKYYTNNFITNLTFRTASLWIPGTAKPGHWTYTLNNTHHSLQALKVT 592
```

FIG. 5B

```
mICACC-1: VTSRAASATLPPITVTPVVNKNTGKFPSPVTVYASIRQGASPILRASVTALIESVNGKTV 639
hICACC-1: VTSRASNATLPPITVTSKTNKDTSKFPSPLVVYANIRQGASPILRASVTALIESVNGKTV 638
hICACC-2: VTSRASNSAVPPATVEAFVERDSLHFPHPVMIYANVKQGFYPILNATVTATVEPETGDPV 652 mICACC-1: TLELLDNGAGADATKNDGVYSRFFTAFDANGRYSVKIWALGGVTSDRQRAAPPKNRAMYI 699
hICACC-1: TLELLDNGAGADATKDDGVYSRYFTTYDTNGRYSVKVRALGGVNAARRRVIPQQSGALYI 698
hICACC-2: TLRLLDDGAGADVIKNDGIYSRYFFSFAANGRYSLKVHVNHSPSISTPAHSIPGSHAMYV 712 mICACC-1: DGWIEDGEVRMNPPRPETS--YVQDKQLCFSRTSSGGSFVATNVPAAAPIPDLFPPCQIT 757
hICACC-1: PGWIENDEIQWNPPRPEINKDDVQHKQVCFSRTSSGGSFVASDVPN-APIPDLFPPGQIT 757
hICACC-2: PGYTANGNIQMNAPRKSVGR-NEEERKWGFSRVSSGGSFSVLGVPA-GPHPDVFPPCKII 770 mICACC-1: DLKASIQGQNLVNLTWTAPGDDYDHGRASNYIIRMSTSIVDLRDHFNTSLQVNTTGLIPK 817
hICACC-1: DLKAEIHGGSLINLTWTAPGDDYDHGTAHKYIIRISTSILDLRDKFNESLQVNTTALIPK 817
hICACC-2: DLEAVKVEEELT-LSWTAPGEDFDQGQATSYEIRMSKSLQNIQDDFNNAILVNTSKRNPQ 829 mICACC-1: EASSEEIFEFELGGNTFG-----NG-----TDIFIAIQAVDKSNLKSEISNIARVSVFIP 867
hICACC-1: EANSEEVFLFKPENITFE-----NG-----TDLFIAIQAVDKVDLKSEISNIARVSLFIP 867
hICACC-2: QAGIREIFTFSPQISTNGPEHQPNGETHESHRIYVAIRAMDRNSLQSAVSNIAQAPLFIP 889 mICACC-1: AQEP---PIPEDSTPPCPDISINSTIPGIHVLKIMWKWLGEMQVTLGLH-------- 913
hICACC-1: PQTPPETPSPDETSAPCPNIHINSTIPGIHILKIMWKWIGELQLSIA---------- 914
hICACC-2: PNSD---PVPARDYLILKGVLTAMGLIGIICLIIVVTHHTLSRKKRADKKENGTKLL 943
```

FIG. 7
ICACC-1 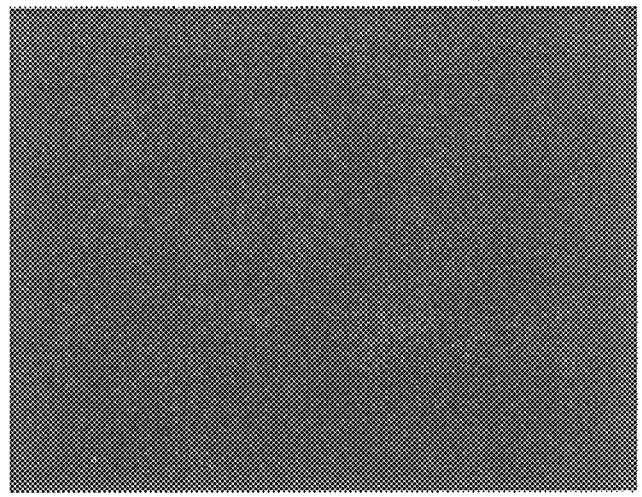
DHFR 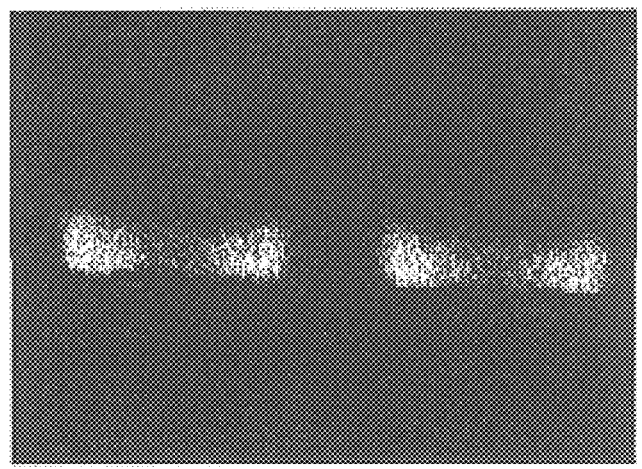

FIG. 8
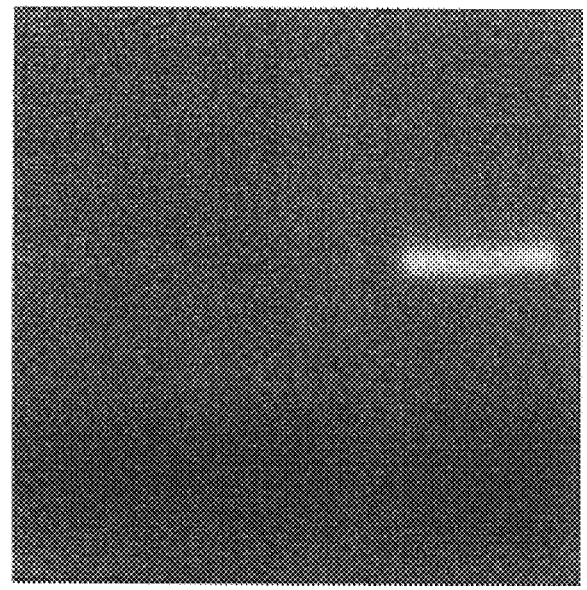
ICACC-1 –
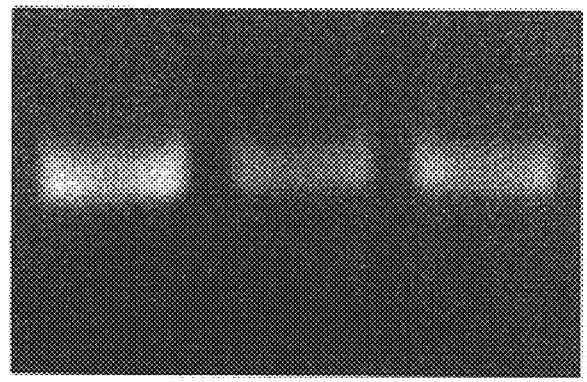
DHFR –

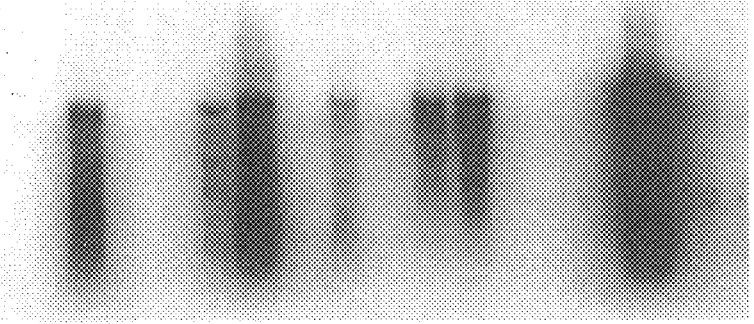
FIG. 9A IL-9 Transgenic Mouse
1 2 3 4 5 6 7 8 9 10 11 12 13 14 15
1. uterus
2. thymus
3. testis
4. stomach
5. Spleen
6. sml. intestine
7. ovary
8. muscle
9. lymph nodes
10. lung
11. liver
12. kidney
13. heart
14. colon
15. brain
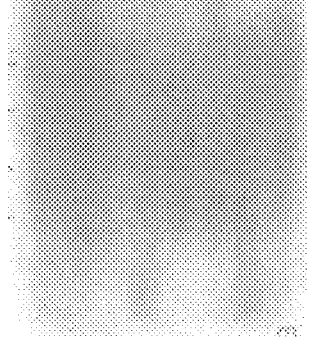
FIG. 9B Normal Mouse
1 2 3 4 5 6 7 8
1. heart
2. brain
3. spleen
4. lung
5. liver
6. skeletal muscle
7. kidney
8. testis

FIG. 18

METHODS FOR IDENTIFICATION OF AGENTS WHICH MODULATE CHLORIDE CHANNEL ACTIVITY

CROSS-REFERENCE TO RELATED APPLICATIONS

This application claims the benefit of U.S. Provisional Patent Application Serial No. 60/076,815 which was filed Mar. 3, 1998 and which is herein incorporated by reference in its entirety. This invention is a 371 of PCT/US99/04703 filed Mar. 3, 1999.

FIELD OF THE INVENTION

This invention relates to modulating activities associated with the IL-9 pathway for the treatment of atopic allergies and related disorders such as asthma.

BACKGROUND OF THE INVENTION

Inflammation is a complex process in which the body's defense system combats foreign entities. While the battle against foreign entities may be necessary for the body's survival, some defense systems respond to foreign entities, even innocuous ones, as dangerous and thereby damage surrounding tissue in the ensuing battle.

Atopic allergy is an ecogenetic disorder, where genetic background dictates the response to environmental stimuli. The disorder is generally characterized by an increased ability of lymphocytes to produce IgE antibodies in response to ubiquitous antigens. Activation of the immune system by these antigens leads to allergic inflammation and may occur after ingestion, penetration through the skin or after inhalation. When this immune activation occurs and is accompanied by pulmonary inflammation and bronchial hyperresponsiveness, this disorder is broadly characterized as asthma. Certain cells are important in this inflammatory reaction and they include T cells and antigen-presenting cells, B cells that produce IgE, basophils that bind IgE and eosinophils. These inflammatory cells accumulate at the site of allergic inflammation and the toxic products they release contribute to tissue destruction related to these disorders.

While asthma is generally defined as an inflammatory disorder of the airways, clinical symptoms arise from intermittent air flow obstruction. It is a chronic, disabling disorder that appears to be increasing in prevalence and severity (Gergen et al., 1992). It is estimated that 30–40% of the population suffer with atopic allergy and 15% of children and 5% of adults in the population suffer from asthma (Gergen et al., 1992). Thus, an enormous burden is placed on health-care resources.

Interestingly, while most individuals experience similar environmental exposures, only certain individuals develop atopic allergy and asthma. This hypersensitivity to environmental allergens known as "atopy" is often indicated by elevated serum IgE levels or abnormally intense skin test response to allergens in atopic individuals as compared to nonatopics (Marsh et al., 1982). Strong evidence for a close relationship between atopic allergy and asthma is derived from the fact that most asthmatics have clinical and serologic evidence of atopy (Clifford et al., 1987; Gergen, 1991; Burrows et al, 1992; Johannson et al., 1972; Sears et al., 1991; Halonen et al., 1992). In particular, younger asthmatics have a high incidence of atopy (Marsh et al., 1982). In addition, immunologic factors associated with an increase in total serum IgE levels are very closely related to impaired pulmonary function (Burrows et al., 1989).

Both the diagnosis and treatment of these disorders are problematic (Gergen et al., 1992). The assessment of inflamed lung tissue is often difficult and frequently the source of the inflammation cannot be determined. It is now generally accepted that failure to control pulmonary inflammation leads to significant loss of lung function over time.

Current treatments suffer their own set of disadvantages. The main therapeutic agents, β agonists, reduce the symptoms thereby transiently improving pulmonary function, but do not affect the underlying inflammation so that lung tissue remains in jeopardy. In addition, constant use of β agonists results in desensitization which reduces their efficacy and safety (Molinoff et al., 1995). The agents that can diminish the underlying inflammation, such as anti-inflammatory steroids, have their own list of disadvantages that range from immunosuppression to bone loss (Molinoff et al., 1995).

Because of the problems associated with conventional therapies, alternative treatment strategies have been evaluated. Glycophorin A (Chu et al., 1992), cyclosporin (Alexander et al., 1992; Morely, 1992) and a nonapeptide fragment of interleukin 2 (IL-2) (Zavyalov et al., 1992) all inhibit potentially critical immune functions associated with homeostasis. What is needed in the art is a treatment for asthma that addresses the underlying pathogenesis. Moreover, these therapies must address the episodic nature of the disorder and the close association with allergy and intervene at a point downstream from critical immune functions.

In the related patent applications mentioned above, applicants have demonstrated that interleukin 9 (IL-9), its receptor and activities effected by IL-9 are the appropriate targets for therapeutic intervention in atopic allergy, asthma and related disorders.

Mediator release from mast cells by allergen has long been considered a critical initiating event in allergy. IL-9 was originally identified as a mast cell growth factor and it has been demonstrated that IL-9 up-regulates the expression of mast cell proteases including MCP-1, MCP-2, MCP-4 (Eklund et al., 1993) and granzyme B (Louahed et al., 1995). Thus, IL-9 appears to serve a role in the proliferation and differentiation of mast cells. Moreover, IL-9 up-regulates the expression of the alpha chain of the high affinity IgE receptor (Dugas et al., 1993). Elevated IgE levels are considered to be a hallmark of atopic allergy and a risk factor for asthma. Furthermore, both in vitro and in vivo studies have shown IL-9 to potentiate the release of IgE from primed B cells (Petit-Frere et al., 1993).

There is substantial support for the role of IL-9 gene in asthma. First, linkage homology between humans and mice suggests that the same gene is responsible for producing biologic variability in response to antigen in both species. Second, differences in expression of the murine IL-9 candidate gene are associated with biologic variability in bronchial responsiveness. In particular, reduced expression of IL-9 is associated with a lower baseline bronchial response in B6 mice. Third, recent evidence for linkage disequilibrium in data from humans suggests IL-9 may be associated with atopy and bronchial hyperresponsiveness consistent with a role for this gene in both species (Doull et al., 1992). Moreover, a genetic alteration in the human gene appears to be associated with loss of cytokine function and lower IgE levels. Fourth, the pleiotropic functions of this cytokine and its receptor in the allergic immune response strongly support a role for the IL-9 pathway in the complex pathogenesis of asthma. Fifth, in humans, biologic variability in the IL-9 receptor also appears to be associated with atopic allergy and asthma Finally, despite the inherited loss of IL-9 receptor function, these individuals appear to be otherwise healthy. Thus, nature has demonstrated in atopic individuals that the therapeutic down-regulation of IL-9 and IL-9 receptor genes or genes activated by IL-9 and its receptor is likely to be safe.

While the role of the IL-9 gene, its receptor and their functions in atopic allergy, asthma and related disorders has been elucidated, a specific need in the art exists for elucidation of the role of genes which are regulated by IL-9 in the etiology of these disorders. Furthermore, most significantly, based on this knowledge, there is a need for the identification of agents that are capable of regulating the activity of these genes or their gene products for treating these disorders.

Cystic fibrosis is yet another disease which effects the lung and is associated with thick secretions resulting in airway obstruction and subsequent colonization and infection by inhaled pathogenic microorganisms (Eng et al., 1996). Cystic fibrosis airway epithelia exhibit a spectrum of ion transport properties that differ from normal, including not only defective cAMP-mediated chloride secretion, but also increased sodium absorption and increased calcium-mediated chloride secretion (Johnson et al., 1995). The increase in calcium-mediated chloride secretion is presumably an attempt to compensate for the overall decrease in chloride secretion due to the defect in cAMP-mediated chloride secretion. It does not adequately compensate for this defect, however, because normal chloride gradients are not maintained. Thus, potential therapeutic remedies for cystic fibrosis rely on mechanisms which increase chloride secretion in airway epithelial cells to compensate for defective cAMP-mediated chloride secretion. Such mechanisms are capable of restoring the cellular chloride gradient thereby alleviating sodium hyperabsorption associated with decreased chloride secretion. A specific need in the art therefore exists for identification of agents capable of enhancing calcium-dependent chloride secretion in cystic fibrosis airway epithelial cells.

SUMMARY OF THE INVENTION

The present invention includes new genes from the calcium activated chloride channel gene family designated ICACC (IL-9 Induced Calcium Activated Chloride Channel), particularly the mouse (SEQ ID NO:1) and human (SEQ ID NO:3 and SEQ ID NO:5) ICACC genes. The ICACC-1 genes are selectively up-regulated by IL-9 and therefore part of the IL-9 signaling pathway. The present invention also includes the protein products of the ICACC genes, particularly, the mouse (SEQ ID NO:2) and human (SEQ ID NO:4 and NO:6) ICACC genes.

The inventors have satisfied the need for diagnosis and treatment of atopic allergy, asthma and related disorders by demonstrating the role of ICACC-1 in the pathogenesis of these disorders. Therapies for these disorders are derived from the down-regulation of ICACC-1 as a member of the IL-9 pathway.

The identification of ICACC-1 has led to the discovery of compounds that are capable of down-regulating its activity. Activity is defined here as any alteration in either chloride channel function or expression of ICACC-1. Molecules that down-regulate ICACC-1 are therefore part of the invention. Down-regulation is defmed here as a decrease in activation, function or synthesis of ICACC-1, its ligands or activators. It is further defined to include an increase in the degradation of ICACC-1 gene, its protein product, ligands or activators.

Down-regulation is therefore achieved in a number of ways. For example, administration of molecules that can destabilize the binding of ICACC-1 with its ligands. Such molecules encompass polypeptide products, including those encoded by the DNA sequences of the ICACC-1 gene or DNA sequences containing various mutations. These mutations may be point mutations, insertions, deletions or spliced variants of the ICACC-1 gene. This invention also includes truncated polypeptides encoded by the DNA molecules described above. These polypeptides being capable of interfering with interaction of ICACC-1 with its ligand and other proteins.

A further embodiment of this invention includes the down-regulation of ICACC-1 function by altering expression of the ICACC-1 gene, the use of antisense gene therapy being an example. Down-regulation of ICACC-1 expression is accomplished by administering an effective amount of antisense oligonucleotides. These antisense molecules can be fashioned from the DNA sequence of the ICACC-1 gene or sequences containing various mutations, deletions, insertions or spliced variants. Another embodiment of this invention relates to the use of isolated RNA or DNA sequences derived from the ICACC-1 gene. These sequences containing various mutations such as point mutations, insertions, deletions or spliced variant mutations of ICACC-1 gene and can be useful in gene therapy.

Molecules that increase the degradation of the ICACC-1 protein may also be used to down-regulate its functions and are within the scope of the invention. Phosphorylation of ICACC-1 may alter protein stability, therefore kinase inhibitors may be used to down-regulate its function. Down-regulation of ICACC-1 may also be accomplished by the use of polyclonal or monoclonal antibodies or fragments thereof directed against the ICACC-1 protein. Such molecules are within the claimed invention. This invention further includes small molecules with the three-dimensional structure necessary to bind with sufficient affinity to block ICACC-1 interactions with its ligands or block function of the chloride channel. ICACC-1 blockade resulting in deregulation of calcium and chloride flux and other processes of proinflammatory cells where it is expressed make these small molecules useful as therapeutic agents in treating inflammation associated with atopic allergy, asthma and related disorders. In a further embodiment, aminosterol compounds are assessed for their ability to block ICACC-1 induction by IL-9 or antigen as a means of determining their usefulness in treating atopic allergies and related disorders.

The agents discussed above represent various effective therapeutic compounds in treating atopic allergies, asthma and other related disorders. Applicants have thus provided antagonists and methods of identifying antagonists that are capable of down-regulating ICACC-1. Applicants also provide methods for down-regulating the activity of ICACC-1 by administering truncated protein products, chloride channel blockers, aminosterols and the like.

Applicants also provide a method for the diagnosis of susceptibility to atopic allergy, asthma and related disorders by describing a method for assaying the induction of ICACC-1, its functions or downstream activities. In a further embodiment, Applicants provide methods to monitor the effects of ICACC-1 down-regulation as a means to follow the treatment of atopic allergy and asthma. Applicants also provide a method for diagnosing autoimmune type diseases such as inflammatory bowel disease (IBD) where suppression of TH2-associated responses (such as the biologic responses associated with IL-9 ) are a common molecular feature. The constitutive expression of ICACC-1 in the small intestine and colon suggest that this is a useful marker for monitoring treatment of Th1 associated disease states such as IBD, where down regulated expression of ICACC-1 will be associated with the disease.

In a further embodiment, Applicants identify a disease state, which can be treated through the up-regulation of ICACC-1. Applicants provide a method for treating the defect in cAMP-mediated chloride secretion in cystic fibrosis airway epithelia by further increasing calcium-dependent chloride secretion through up-regulation of ICACC-1. This up-regulation of ICACC-1 resulting in increased chloride secretion and thus restoration of the cellular chloride gradient resulting in normal airway epithelial cell function. Applicants provide a method for treating inflammatory bowel disease (IBD) with local delivery of ICACC-1 via gene therapy or up regulation of ICACC-1 to enhance TH2-associated responses for suppressing the Th1-associated IBD autoimmune disease.

The accompanying figures, which are incorporated in and constitute a part of this specification, illustrate several embodiments of the invention and together with the description, serve to explain the principle of the invention.

DESCRIPTION OF THE FIGURES

FIG. 2 shows the nucleotide (SEQ ID NO:1) and amino acid (SEQ ID NO:2) sequence of the murine ICACC-1 cDNA.

FIG. 3 shows an alignment of the murine ICACC-1 protein with a bovine calcium activated chloride channel (SEQ ID NO:18).

FIG. 4A shows the nucleotide (SEQ ID NO:3) and amino acid (SEQ ID NO:4) sequence of the human ICACC-2 cDNA.

FIG. 4B shows the nucleotide (SEQ ID NO:5) and amino acid (SEQ ID NO:6) sequence of the human ICACC-1 cDNA.

FIG. 5 shows an alignment of the murine ICACC-1 protein with the human ICACC-1 and ICACC-2 protein.

FIG. 7 shows the expression of ICACC-1 in the lungs of DBA and C57B6 mice.

FIG. 8 shows the expression of ICACC-1 in the lung of the C57B6 mouse with and without intratracheal administration of IL-9.

FIG. 9 shows the expression of ICACC-1 in tissues from normal (Balb/C) and IL-9 overexpressing (Tg5) mice.

FIG. 18 shows suppression of IL-9 induced eotaxin by chloride channel blockers

DETAILED DESCRIPTION OF THE INVENTION

Figure 1:
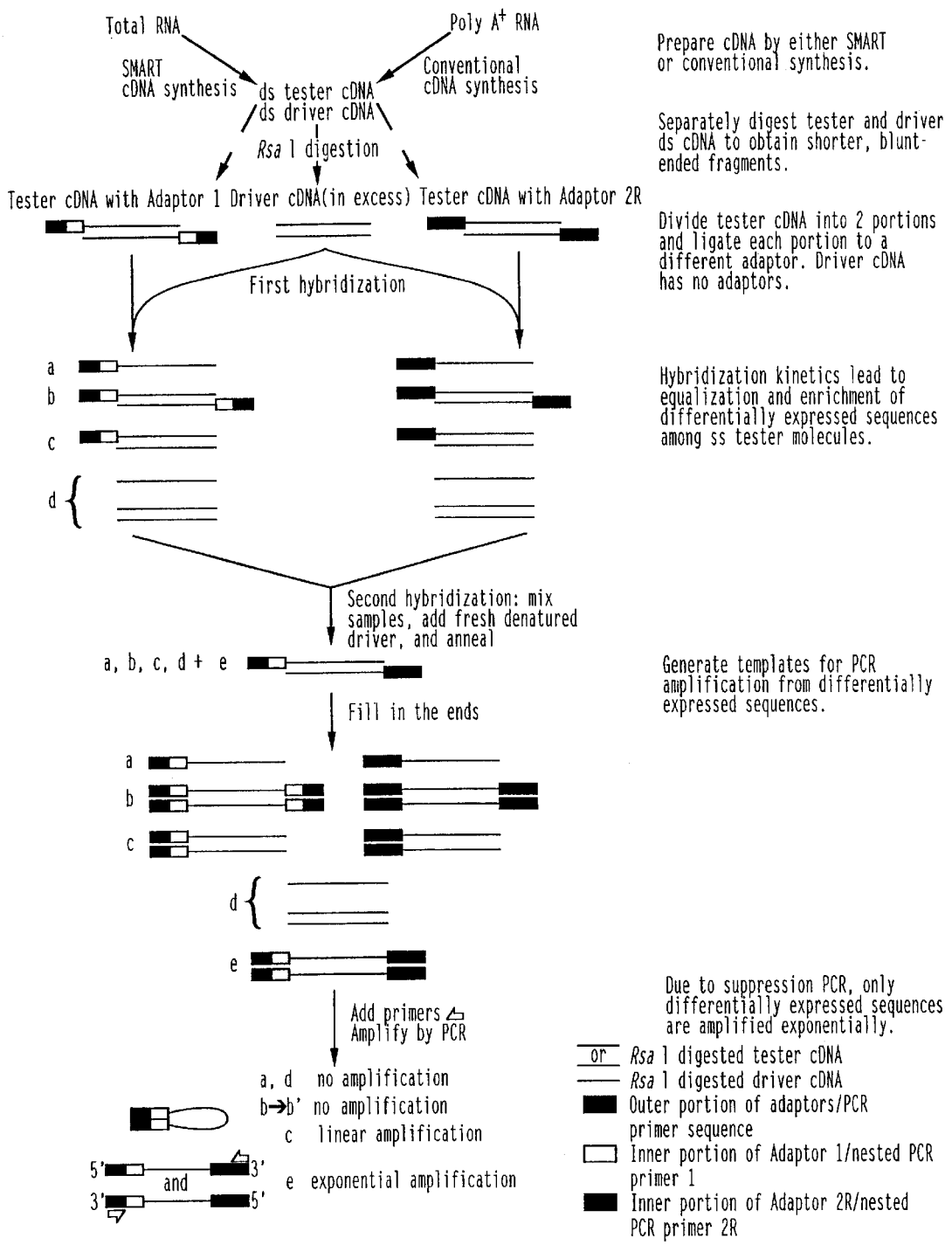
FIG. 1 shows a schematic diagram of the suppressive PCR cDNA subtraction technique.

The inventors have resolved a crucial need in the art by elucidating critical genes in the IL-9 pathway and compositions affecting that pathway which may be used in the diagnosis, prevention or treatment of atopic allergy including asthma and related disorders. Asthma encompasses inflammatory disorders of the airways with reversible airflow obstruction. Atopic allergy refers to atopy and related disorders including asthma, bronchial hyperresponsiveness, rhinitis, urticaria, allergic inflammatory disorders of the bowel and various forms of eczema. Atopy is a hypersensitivity to environmental allergens expressed as the elevation of serum total IgE or abnormal skin test responses to allergens as compared to controls. Bronchial hyperresponsiveness is a heightened broncho constrictor response to a variety of stimuli.

A. ICACC Proteins

The present invention provides isolated ICACC protein, allelic variants of the protein, and conservative amino acid substitutions of the protein. As used herein, the ICACC protein or polypeptide includes a protein that has the murine amino acid sequence of SEQ ID NO:2 or the human amino acid sequence depicted in SEQ ID No.4 or SEQ ID No.6. The invention includes naturally occurring allelic variants and proteins that have a slightly different amino acid sequence than that specifically recited above. Allelic variants, though possessing a slightly different amino acid sequence than those recited above, will still have the same or similar biological functions associated with the ICACC protein.

As used herein, the family of proteins related to the ICACC protein refer to proteins that have been isolated from organisms in addition to humans or mice. The methods used to identify and isolate other members of the family of proteins related to the human and/or murine ICACC proteins are described below.

The proteins of the present invention are preferably in isolated form. As used herein, a protein is said to be isolated when physical, mechanical or chemical methods are employed to remove the protein from cellular constituents that are normally associated with the protein. A partially isolated protein, as used herein, includes ICACC proteins isolated in membrane fragments, including cellular membrane fragments containing a recombinantly expressed ICACC protein. A skilled artisan can readily employ standard purification methods to obtain an isolated protein.

The proteins of the present invention further include conservative variants of the proteins herein described. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein may be altered without adversely affecting a biological activity. Accordingly, the amino acid sequence can be altered, for example to render the peptide more hydrophobic or hydrophilic, without adversely affecting the biological activities of the protein.

Ordinarily, the allelic variants, the conservative substitution variants, and the members of the protein family, will have an amino acid sequence having at least about 55%, at least about 75% amino acid sequence identity with the murine sequence set forth in SEQ ID No.2 or the human sequences of SEQ ID NO:4 or SEQ ID No.6, more preferably at least 80%, even more preferably at least 90%, and most preferably at least 95%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the proteins of the present invention include molecules having the amino acid sequence disclosed in SEQ ID Nos. 2, 4 or 6; fragments thereof having a consecutive sequence of at least about 3, 4, 5, 6, 10, 15, 20, 25, 30, 35 or more amino acid residues of the ICACC protein; amino acid sequence variants of such sequence wherein an amino acid residue has been inserted N- or C-terminal to, or within, the disclosed sequence; and amino acid sequence variants of the disclosed sequence, or their fragments as defined above, that have been substituted by another residue. Contemplated variants further include those containing predetermined mutations by, e.g., homologous recombination, site-directed or PCR mutagenesis, and the corresponding proteins of other animal species, including but not limited to rabbit, rat, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

As described below, members of the family of proteins can be used: 1) to identify agents which modulate at least one activity of the protein; 2) in methods of identifying binding partners for the protein; and 3) as an antigen to raise polyclonal or monoclonal antibodies.

B. Nucleic Acid Molecules

Figure 6:
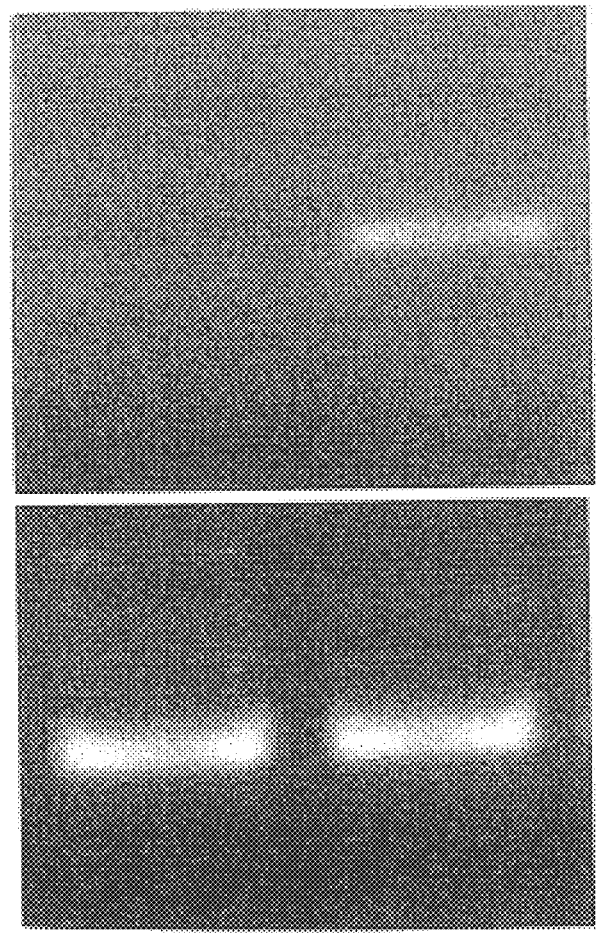
FIG. 6 shows ICACC-1 expression in the lung of normal mice (FVB) compared to transgenic mice overexpressing the IL-9 gene (Tg5).
Figure 12A:
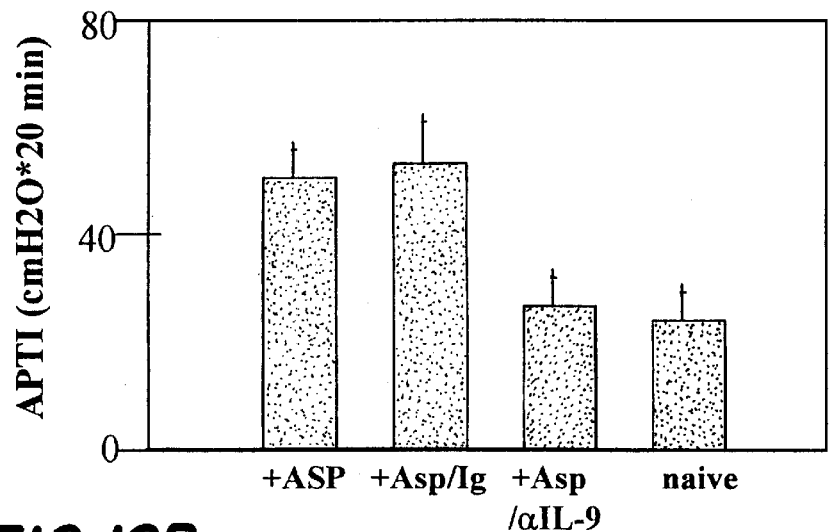
FIG. 12 shows the suppression of BHR and lung eosinophilia by anti-IL9 in mice exposed to *Aspergillus fumagatus*.
Figure 12B:
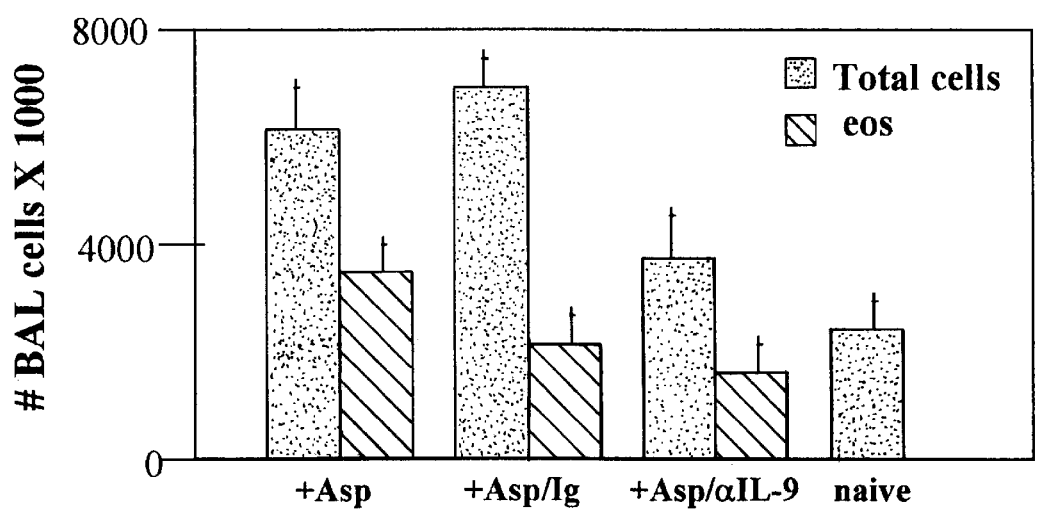
Figure 13:
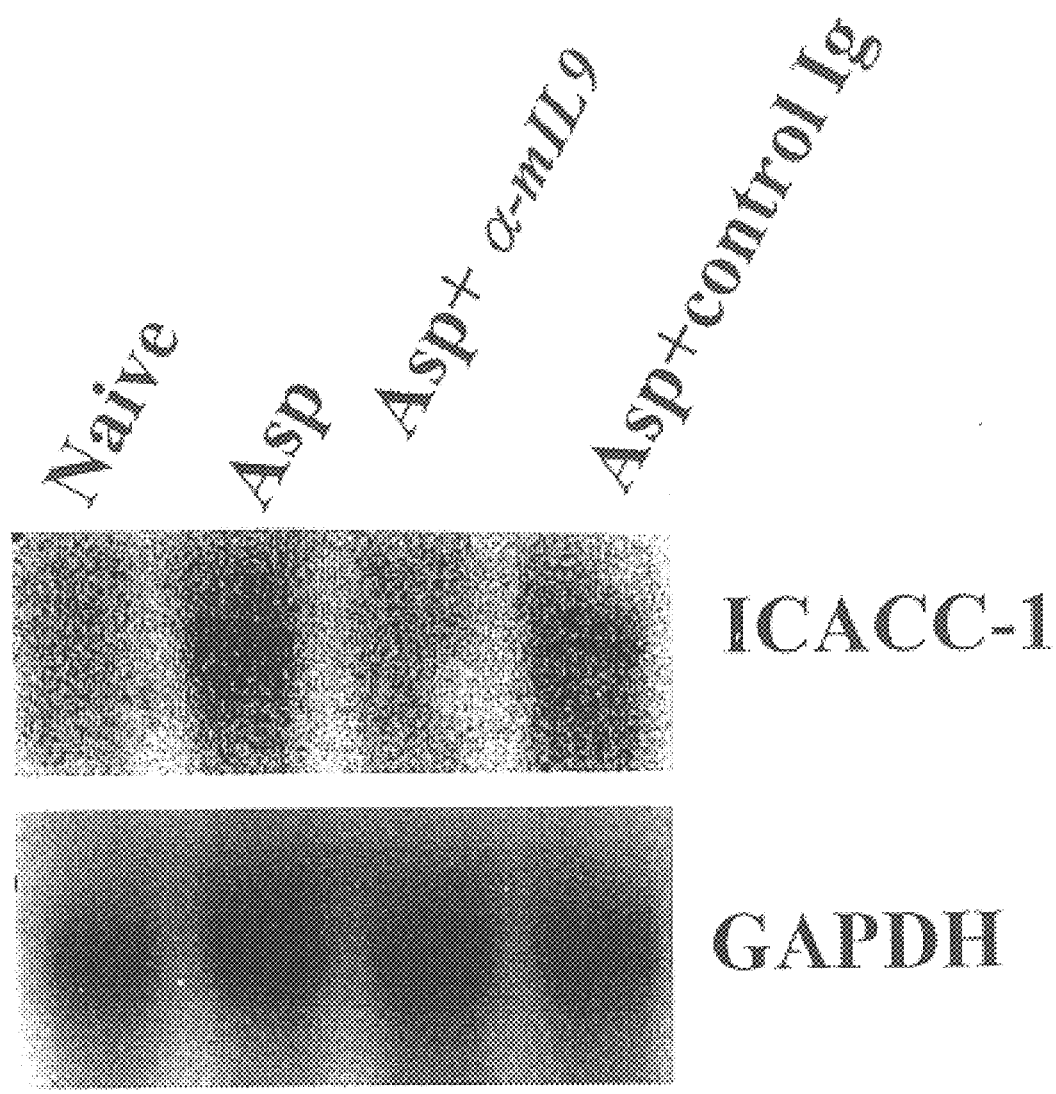
FIG. 13 shows suppression of ICACC-1 in antigen exposed animals treated with anti-IL9.

The murine ICACC-1 gene was identified by subtractive cDNA cloning experiments 15 that were performed in order to identify genes specifically induced by IL-9. A schematic diagram of the subtractive cDNA cloning method is provided in FIG. 1. RNA derived from lungs of transgenic mice overexpressing the murine IL-9 transgene (Tg5) was used to isolate genes expressed in response to IL-9 as opposed to those which are not expressed in the parental strain (FVB). FIG. 6 shows a Northern blot with RNA from a lung of a Tg5 mouse (right lane) and a FVB mouse (left lane) demonstrating these findings. Expression of ICACC-1 was also observed in the lung of the DBA murine strain which has been shown to express elevated baseline IL-9 levels in their lungs (FIG. 7). ICACC-1 expression was not observed in the lungs of the C57B6 strain where IL-9 expression is below the limits of detection (FIG. 7) (Nicolaides et al., 1997). The direct effect of IL-9 on inducing ICACC-1 expression was demonstrated when IL-9 was instilled into the trachea of the C57B6 mouse. The results of this experiment demonstrated that ICACC-1 was expressed in the lungs of the IL-9 instilled mice but not in naive or vehicle treated mice (FIG. 8), indicating that this gene is induced by IL-9. The results also show that ICACC-1 gene expression is induced in the lung of antigen exposed mice which exhibit asthmatic-like features (BHR, lung eosinophilia) (FIGS. 10 and 12). The antigen induced BHR and lung eosinophilia can be suppressed in mice by treatment with anti-IL9 (FIG. 12), which also results in down regulation of ICACC-1 (FIG. 13).

The murine ICACC-1 gene displayed significant homology (~50%) with a member of the bovine calcium activated chloride channel family (FIG. 3) (Cunningham et al., 1995). The full length cDNA was cloned from a murine cDNA library (FIG. 2). Several EST were identified which displayed partial homology to the murine ICACC-1. These EST were obtained from the IMAGE consortium (Lawrence Livermore National Laboratory) and sequenced. A full length cDNA sequence was isolated for human ICACC-1 and 2 by library screening and 5'-and 3' RACE cloning (Clonetech). Analysis of the encoded murine protein sequence identified several conserved motifs including multiple transmembrane domains and several phosphorylation and glycosylation sites.

Expression of murine ICACC-1 was undetectable using standard commercial tissue blots but elevated expression of ICACC-1 was observed in lung, lymph node, colon, spleen, stomach, uterus and ovary derived from IL-9 transgenic mice (FIG. 9). Interestingly, these tissues all contain various epithelial cell types, suggesting that this gene may be restricted to IL-9 responsive epithelial cells. This data is supported by the finding that ICACC-1 gene expression is induced in antigen exposed mice and this induction can be suppressed by anti-IL9 treatment (FIGS. 10, 12, and 13).

Figure 14:
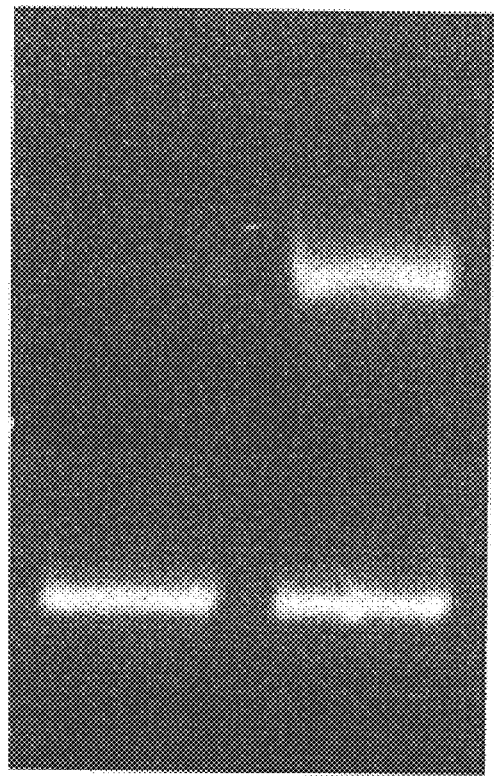
FIG. 14 shows ICACC-1 induction by IL-9 in human primary lung epithelial cells (NHBE).
Figure 15:
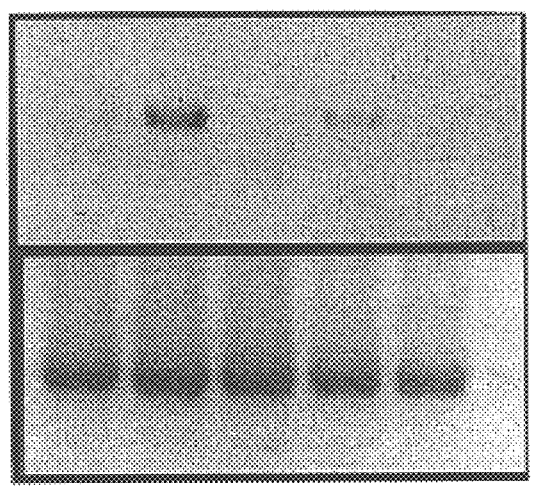
FIG. 15 shows ICACC-1 induction by IL-9 in human primary lung cultures.

To further understand which cell type is capable of expressing ICACC-1, Applicants tested human lung epithelial cells for their responsiveness to IL-9 as determined by ICACC-1 induced gene expression. As shown in FIG. 14, the human lung epithelial cell line designated NHBE (Clonetics), expressed ICACC-1 mRNA when grown in the presence, but not in the absence of IL-9. When human primary lung cultures were grown in the presence of recombinant IL-9, ICACC-1 expression was induced in contrast to cell cultures grown in medium alone (FIG. 15).

The nucleic acid molecules of the present invention include nucleic acid molecules that encode the proteins having SEQ ID No.2, SEQ ID No.4, SEQ ID NO:6 and the related proteins herein described, preferably in isolated form. As used herein, "nucleic acid" is defined as RNA or DNA that encodes a protein or peptide as defined above, or is complementary to nucleic acid sequence encoding such peptides, or hybridizes to such nucleic acid and remains stably bound to it under appropriate stringency conditions, or encodes a polypeptide sharing at least 55% sequence identity, 75% sequence identity, preferably at least 80%, and more preferably at least 85%, with the peptide sequences. Specifically contemplated are genomic DNA, cDNA, mRNA and antisense molecules, as well as nucleic acids based on alternative backbones or including alternative bases whether derived from natural sources or synthesized. Such hybridizing or complementary nucleic acids, however, are defined further as being novel and unobvious over any prior art nucleic acid including that which encodes, hybridizes under appropriate stringency conditions, or is complementary to nucleic acid encoding a protein according to the present invention.

Homology or identity is determined by BLAST (Basic Local Alignment Search Tool) analysis using the algorithm employed by the programs blastp, blastn, blastx, tblastn and tblastx (Karlin, et al. Proc. Natl. Acad. Sci. USA 87: 2264–2268 (1990) and Altschul, S. F. J. Mol. Evol. 36: 290–300(1993), fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (Nature Genetics 6: 119–129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff, et al. Proc. Natl. Acad. Sci. USA 89: 10915–10919 (1992), fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

"Stringent conditions" are those that (1) employ low ionic strength and high temperature for washing, for example, 0.015M NaCl/0.0015M sodium titrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

The present invention further provides fragments of the encoding nucleic acid molecule. As used herein, a fragment of an encoding nucleic acid molecule refers to a small portion of the entire protein encoding sequence. The size of the fragment will be determined by the intended use. For example, if the fragment is chosen so as to encode an active portion of the protein, the fragment will need to be large enough to encode the functional region(s) of the protein or may encode regions of homology between the ICACC proteins in FIG. 5. If the fragment is to be used as a nucleic acid probe or PCR primer, then the fragment length is chosen so as to obtain a relatively small number of false positives during probing/priming.

Fragments of the encoding nucleic acid molecules of the present invention (i.e., synthetic oligonucleotides) that are used as probes or specific primers for the polymerase chain reaction (PCR), or to synthesize gene sequences encoding proteins of the invention can easily be synthesized by chemical techniques, for example, the phosphotriester method of Matteucci, et al., (*J. Am. Chem. Soc.* 103:3185–3191, 1981) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

C. Isolation of Other Related Nucleic Acid Molecules

As described above, the identification of the murine nucleic acid molecule having SEQ ID NO:1 and the human nucleic acid molecules having SEQ ID No.3 or SEQ ID No 5 allows a skilled artisan to isolate nucleic acid molecules that encode other members of the ICACC protein family in addition to the murine or human sequences herein described.

Essentially, a skilled artisan can readily use the amino acid sequence of SEQ ID NOS: 2, 4 or 6 to generate antibody probes to screen expression libraries prepared from appropriate cells. Typically, polyclonal antiserum from mammals such as rabbits immunized with the purified protein (as described below) or monoclonal antibodies can be used to probe a mammalian cDNA or genomic expression library, such as lambda gtll library, to obtain the appropriate coding sequence for other members of the protein family. The cloned cDNA sequence can be expressed as a fusion protein, expressed directly using its own control sequences, or expressed by constructions using control sequences appropriate to the particular host used for expression of the enzyme.

Alternatively, a portion of the coding sequence herein described can be synthesized and used as a probe to retrieve DNA encoding a member of the protein family from any mammalian organism. Oligomers containing approximately 18–20 nucleotides (encoding about a 6–7 amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

D. rDNA Molecules Containing a Nucleic Acid Molecule

The present invention further provides recombinant DNA molecules (rDNAs) that contain a ICACC coding sequence. As used herein, a rDNA molecule is a DNA molecule that has been subjected to molecular manipulation in situ. Methods for generating rDNA molecules are well known in the art, for example, see Sambrook et al., *Molecular Cloning* (1989). In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pPL and pKK223 available from Pharmacia, Piscataway, N.J.

Expression vectors compatible with eukaryotic cells, preferably those compatible with vertebrate cells, can also be used to form a rDNA molecules that contains a coding sequence. Eukaryotic cell expression vectors are well known in the art and are available from several commercial sources. Typically, such vectors are provided containing convenient restriction sites for insertion of the desired DNA segment Typical of such vectors are pSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., *J. Mol. Anal. Genet.* 1:327–341, 1982.) Alternatively, the selectable marker can be present on a separate plasmid, and the two vectors are introduced by co-transfection of the host cell, and selected by culturing in the appropriate drug for the selectable marker.

E. Host Cells Containing an Exogenously Supplied Coding Nucleic Acid Molecule

The present invention further provides host cells transformed with a nucleic acid molecule that encodes an ICACC protein, preferably an ICACC-1 protein, of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eukaryotic tissue culture cell lines. Any prokaryotic host can be used to express a rDNA molecule encoding a protein of the invention. The preferred prokaryotic host is *E. coli.*

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc. Natl. Acad. Sci. USA* 69:2110, 1972; and Maniatis et al., *Molecular Cloning. A Laboratory Mammal,* Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol.* 52:456, 1973; Wigler et al., *Proc. Natl. Acad. Sci. USA* 76:1373–76, 1979.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.* 98:503, 1975, or Berent et al., *Biotech.* 3:208, 1985 or the proteins produced from the cell assayed via an immunological method.

F. Production of Recombinant Proteins using a rDNA Molecule

The present invention further provides methods for producing an ICACC protein of the invention using nucleic acid molecules herein described. In general terms, the production of a recombinant form of a protein typically involves the following steps:

First, a nucleic acid molecule is obtained that encodes a protein of the invention, such as the nucleic acid molecule depicted in SEQ ID NOS.1, 3 or 5 or the open reading frames of these molecules. If the encoding sequence is uninterrupted by introns, it is directly suitable for expression in any host.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

G. Methods to Identify Binding Partners

Another embodiment of the present invention provides methods for use in isolating and identifying binding partners of proteins of the invention In detail, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner that bound to the protein of the invention can then be removed and further analyzed. To identify and isolate a binding partner, the entire protein, for instance a ICACC protein of SEQ E) No.2, SEQ ID No. 4 or SEQ ID NO:6 can be used. Alternatively, a fragment of the protein or a membrane fragment containing the protein may be used.

As used herein, a cellular extract refers to a preparation or fraction which is made from a lysed or disrupted cell. The preferred source of cellular extracts are cells derived from human tissues or cells.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture. To aid in separating associated binding partner pairs from the mixed extract, the protein of the invention can be immobilized on a solid support For example, the protein can be attached to a nitrocellulose matrix or acrylic beads. Attachment of the protein to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al. (1997) Methods Mol. Biol. 69:171–84 or Sauder et al. J Gen. Virol. 77(5):991–6 or identified through the use of epitope tagged proteins or GST fusion proteins.

Alternatively, the nucleic acid molecules of the invention can be used in a yeast two-hybrid system, preferably systems for screening binding partners of membrane proteins. The yeast two-hybrid system has been used to identify other protein partner pairs and can readily be adapted to employ the nucleic acid molecules herein described.

H. Methods to Identify Agents that Modulate the Expression a Nucleic Acid Encoding and ICACC Protein.

Another embodiment of the present invention provides methods for identifying agents that modulate the expression of a nucleic acid encoding a protein of the invention such as a protein having the amino acid sequence of SEQ ID NO:2 or SEQ ID NO:6. Such assays may utilize any available means of monitoring for changes in the expression level of the nucleic acids of the invention. As used herein, an agent is said to modulate the expression of a nucleic acid of the invention, for instance a nucleic acid encoding the protein having the sequence of SEQ ID NO:2 or SEQ ID NO:6 if it is capable of up or down-regulating expression of the nucleic acid in a cell.

Agents of the invention may relate to antisense or gene therapy. It is now known in the art that altered DNA molecules can be tailored to provide a selected effect, when provided as antisense or gene therapy. The native DNA segment coding for ICACC-1 has two strands; a sense strand and an antisense strand held together by hydrogen bonds. The MRNA coding for the receptor has a nucleotide sequence identical to the sense strand, with the expected substitution of thymidine by uridine. Thus, based upon the knowledge of the receptor sequence, synthetic oligonucleotides can be synthesized. These oligonucleotides can bind to the DNA and RNA coding for ICACC-1. The active fragments of the invention, which are complementary to MRNA and the coding strand of DNA, are usually at least about 15 nucleotides, more usually at least 20 nucleotides, preferably 30 nucleotides and more preferably may be 50 nucleotides or more. The binding strength between the sense and antisense strands is dependent upon the total hydrogen bonds. Therefore, based upon the total number of bases in the mRNA, the optimal length of the oligonucleotide sequence may be easily calculated by the skilled artisan.

The sequence may be complementary to any portion of the sequence of the mRNA. For example, it may be proximal to the 5'-terminus or capping site or downstream from the capping site, between the capping site and the initiation codon and may cover all or only a portion of the non-coding region or the coding region. The particular site(s) to which the antisense sequence binds will vary depending upon the degree of inhibition desired, the uniqueness of the sequence, the stability of the antisense sequence, etc.

In the practice of the invention, expression of ICACC-1. is down-regulated by administering an effective amount of antisense oligonucleotide sequences described above. The oligonucleotide compounds of the invention bind to the mRNA coding for human ICACC-1 thereby inhibiting expression (translation) of these proteins. The isolated DNA sequences, containing various mutations such as point mutations, insertions, deletions or spliced mutations of ICACC-1 are useful in gene therapy as well.

In one assay format for agents, cell lines that contain reporter gene fusions between the open reading frame and any assayable fusion partner may be prepared. Numerous assayable fusion partners are known and readily available including the firefly luciferase gene and the gene encoding chloramphenicol acetyltransferase (Alam et al. (1990) *Anal. Biochem.* 188:245–254). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding an ICACC-1 protein.

Additional assay formats may be used to monitor the ability of the agent to modulate the expression of a nucleic acid encoding a protein of the invention, such as the protein having SEQ ID NO:2 or SEQ ID NO:6. For instance, MRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al. (Molecular Cloning: A Laboratory Manual, 2nd Ed. Clod Spring Harbor Laboratory Press, 1989). Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al. (*Molecular Cloning: A Laboratory Approach,* Cold Spring Harbor Press, NY, 1989) or Ausubel et al. (*Current Protocols in Molecular Biology,* Greene Publishing Co., NY, 1995).

Hybridization conditions are modified using known methods, such as those described by Sambrook et al. and Ausubel et al. as required for each probe. Hybridization of total cellular RNA or RNA enriched for polyA RNA can be accomplished in any available format For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a porous glass wafer. The glass wafer can then be exposed to total cellular RNA or polyA RNA from a sample under conditions in which the affixed sequences will specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding an ICACC protein, preferably an ICACC-1 protein, are identified.

Hybridization for qualitative and quantitative analysis of mRNAs may also be carried out by using a RNase Protection Assay (i.e., RPA, see Ma et al. (1996) Methods 10: 273-238). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising 80% formamide, 40 mM Pipes, pH 6.4,0.4 M NaCl and 1 mM EDTA. The resulting hybrids are then digested in a buffer comprising 40 $\mu$g/ml ribonuclease A and 2 $\mu$g/ml ribonuclease. After deactivation and extraction of extraneous proteins, the samples are loaded onto urea/polyacrylamide gels for analysis.

In another assay format for agents which effect the expression of the instant gene products, cells or cell lines would first be identified which express said gene products physiologically (e.g., see the Figures for tissue distribution). Cell and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Further, such cells or cell lines would be transduced or transfected with an expression vehicle (e.g., a plasmid or viral vector) construct comprising an operable non-translated 5'-promoter containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag. Such a process is well known in the art (see Maniatis). Cells may be exposed to IL-9.

Cells or cell lines transduced or transfected as outlined above would then be contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art Subsequent to contacting the cells with the agent, said cells will be disrupted and the polypeptides of the disruptate are fractionated such that a polypeptide fraction is pooled and contacted with an antibody to be further processed by immunological assay (e.g., ELISA, immunoprecipitation or Western blot). The pool of proteins isolated from the "agent contacted" sample will be compared with a control sample where only the excipient is contacted with the cells and an increase or decrease in the immunologically generated signal from the "agent contacted" sample compared to the control will be used to distinguish the effectiveness of the agent.

I. Methods to Identify Agents that Modulate at Least One Activity of an ICACC Protein.

Another embodiment of the present invention provides methods for identifying agents that modulate at least one activity of a protein of the invention, such as a protein having the amino acid sequence of SEQ ID No.2, SEQ ID NO:4 or SEQ ID No.6 and preferably, an ICACC-1 protein. Such methods or assays may utilize any means of monitoring or detecting the desired activity.

Specific assays may be based on monitoring the cellular functions of ICACC-1. Antagonists of the invention include those molecules that interact or bind to ICACC-1 and inactivate this receptor. To identify other allosteric, inverse or weak antagonists of the invention, one may test for binding to ICACC-1. The present invention includes antagonists of ICACC-1 that block activation of this receptor. Antagonists are compounds that are themselves devoid of pharmacological activity but cause effects by preventing the action of an agonist. To identify an antagonist of the invention, one may test for competitive binding with natural ligands of ICACC-1. Assays of antagonistic binding and activity can be derived from monitoring ICACC-1 functions for down-regulation as described herein and in the cited literature. The binding of the antagonist may involve all known types of interactions including ionic forces, hydrogen bonding, hydrophobic interactions, van der Waals forces and covalent bonds. In many cases, bonds of multiple types are important in the interaction of an agonist or antagonist with a molecule like ICACC-1.

In a further embodiment, these compounds may be analogues of ICACC-1 or its ligands. ICACC-1 analogues may be produced by point mutations in the isolated DNA sequence for the gene, nucleotide substitutions and/or deletions which can be created by methods that are all well described in the art (Simoncsits et al., 1994). This invention also includes spliced variants of ICACC-1 and discloses isolated nucleic acid sequences of ICACC-1, which contain deletions of one or more of its exons. The term "spliced variants" as used herein denotes a purified and isolated DNA molecule encoding human ICACC-1 comprising at least one exon. There is no evidence of naturally expressed spliced mutants in the art. It must be understood that these exons may contain various point mutations.

Structure-activity relationships may be used to modify the antagonists of the invention. For example, the techniques of X-ray crystallography and NMR may be used to make modifications of the invention. For example, one can create a three-dimensional structure of human ICACC-1 that can be used as a template for building structural models of deletion mutants using molecular graphics. These models can then be used to identify and construct a ligand for ICACC-1 which alters normal chloride channel function. In still another embodiment, these compounds may also be used as dynamic probes for ICACC-1 structure and to develop ICACC-1 antagonists using cell lines or other suitable means of assaying ICACC-1 activity.

In addition, this invention also provides compounds that prevent the synthesis or reduce the biologic stability of ICACC-1. Biologic stability is a measure of the time between the synthesis of the molecule and its degradation. For example, the stability of a protein, peptide or peptide mimetic (Kauvar, 1996) therapeutic may be prolonged by using D-amino acids or shortened by altering its sequence to make it more susceptible to enzymatic degradation.

In another embodiment, antagonists of the invention are antibodies to ICACC-1. The antibodies to ICACC-1 may be either monoclonal or polyclonal, made using standard techniques well known in the art (See Harlow & Lane's *Antibodies: A Laboratory Manual,* Cold Spring Harbor Laboratory Press, 1988). They can be used to block ICACC-1 activation by binding to extracellular regions of the protein required for ligand binding or activation. In one embodiment, the antibodies interact with ICACC-1, in another they interact with the ligands for ICACC-1. The ICACC-1 used to elicit these antibodies can be the ICACC-1 protein or any of the ICACC-1 variants or fragments discussed above. Antibodies are also produced from peptide sequences of ICACC-1 using standard techniques in the art (see *Protocols in Immunology,* John Wiley & Sons, 1994).

In one assay format, the relative amounts of ICACC-1 protein of the invention between a cell population that has been exposed to the agent to be tested compared to an unexposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes are prepared by immunizing suitable mammalian hosts in appropriate immunization protocols using the peptides. polypeptides or proteins of the invention if they are of sufficient length, or, if desired, or if required to enhance immunogenicity, conjugated to suitable carriers. Methods for preparing immunogenic conjugates with carriers such as BSA, KLH, or other carrier proteins are well known in the art In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at either the amino or carboxy terminus with a Cys residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten polypeptide or protein. When the appropriate immortalized cell culture secreting the desired antibody is identified, the cells can be cultured either in vitro or by production in ascites fluid.

The desired monoclonal antibodies are then recovered from the culture supernatant or from the ascites supernatant Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin. Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action.

The agents of the present invention can be, as examples, peptides, small molecules, vitamin derivatives, as well as carbohydrates. A skilled artisan can readily recognize that there is no limit as to the structural nature of the agents of the present invention. The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

J. Uses for Agents that Modulate at Least One Activity of an ICACC Protein.

Further evidence defining the role of ICACC-1 in the pathogenesis of atopic allergy, bronchial hyperresponsiveness, asthma and related disorders is derived directly from the Applicants observation that IL-9 selectively induces ICACC-1. Thus, the pleiotropic role for IL-9, which is important to a number of antigen induced responses is dependent in part, on the up-regulation of ICACC-1 in cells critical to atopic allergy. When the functions of IL-9 are down-regulated by antibody pretreatment prior to aerosol challenge with antigen, animals can be completely protected from the antigen induced responses. These responses include: bronchial hyperresponsiveness, eosinophilia and elevated cell counts in bronchial lavage, histologic changes in lung associated with inflammation and elevated serum IgE. The suppression of IL-9 and asthmatic-like responses is associated with down regulated expression of ICACC-1 (FIG. 13). Thus, treatment of such responses, which underlie the pathogenesis of atopic allergy and characterize allergic inflammation associated with this disorder, by down-regulating ICACC-1, is within the scope of this invention.

Figure 17:
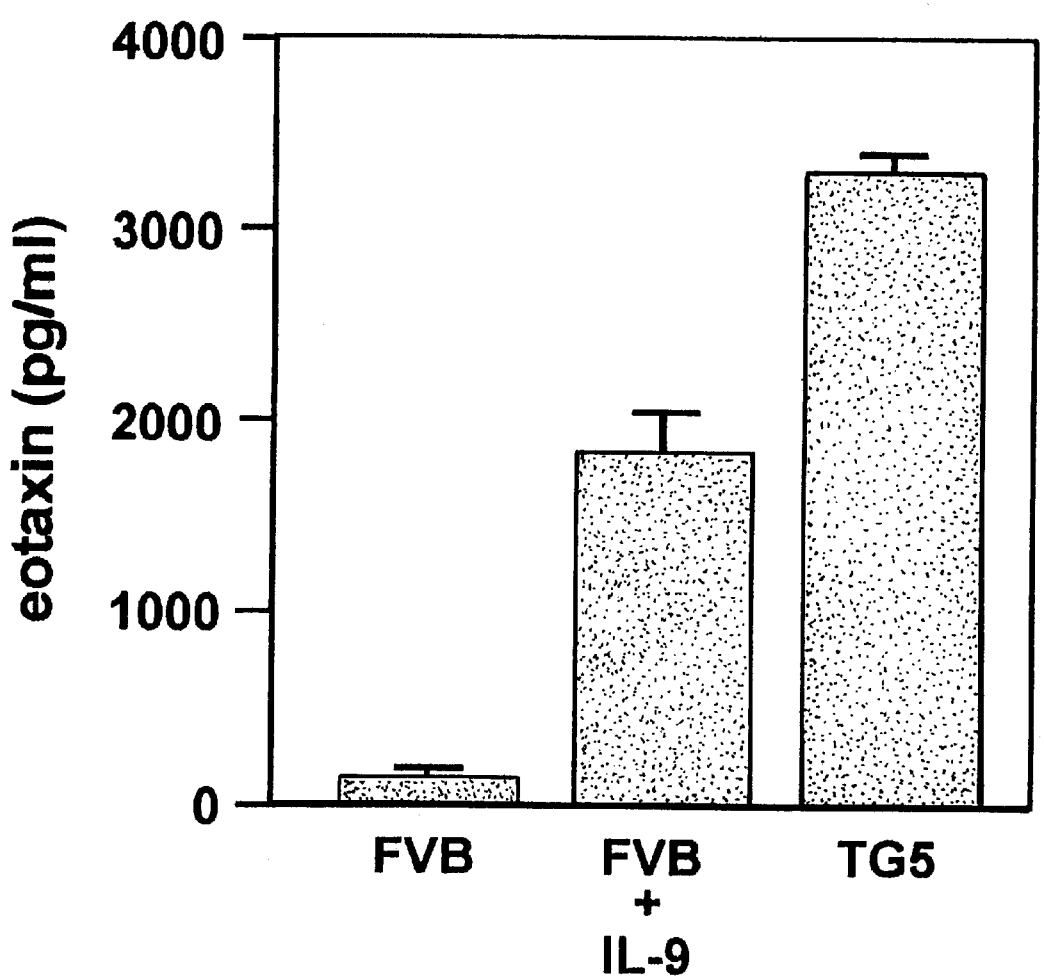
FIG. 17 shows IL-9 induces eotaxin production from epithelial cells in primary lung cultures

The involvement of chloride channels in IL-9 biologic responses is addressed by in vitro primary lung cultures that produce secreted eotaxin protein upon IL9 stimulation (FIG. 17). The treatment of these cultures with known chloride channel inhibitors results in suppression of the IL-9 induced eotaxin response (FIG. 18) and thus provides an assay for screening for ICACC-1 inhibitors. In another embodiment cell lines in which ICACC-1 expression vectors are introduced can be used to screen for specific chloride channel inhibitors.

Applicants also teach the down-regulation of ICACC-1 by administering antagonists of ICACC-1. The skilled artisan will recognize that all molecules containing the requisite three-dimensional structural conformation critical for activation of, or ligand binding to ICACC-1 are within the scope of this invention.

The demonstration of an IL-9 sequence associated with an asthma-like phenotype and one associated with the absence of an asthma-like phenotype, indicates that the inflammatory response to antigen in the lung is IL9 dependent Down-regulating ICACC-1, which is selectively induced downstream in the IL-9 pathway, will therefore protect against this antigen induced response.

In addition to the direct regulation of the ICACC-1 gene, this invention also encompasses methods of inhibiting the intracellular signaling by ICACC-1. It is known in the art that highly exergonic phosphoryl-transfer reactions are catalyzed by various enzymes known as kinases. In other words, a kinase transfers phosphoryl groups between ATP and a metabolite. Included within the scope of this invention are specific inhibitors of protein kinases. Thus, inhibitors of these kinases are useful in the down-regulation of ICACC-1 and are therefore useful in the treatment of atopic allergies and asthma.

In still another aspect of the invention, surprisingly, aminosterol compounds were found to be useful in the inhibition of ICACC-1 induction by IL-9. Aminosterol compounds which are useful in this invention are described in U.S. patent application, Ser. No. 08/290,826 and its related applications Ser. Nos. 08/416,883 and 08/478,763 as well as in Ser. No. 08/483,059 and its related applications Ser. Nos. 08/483,057, 08/479,455, 08/479,457, 08/475,572, 08/476, 855, 08/474,799 and 08/487,443, which are specifically incorporated herein by reference in their entirety.

While a therapeutic potential for ICACC-1 down-regulation has been identified, Applicants have also recognized a therapeutic potential for up-regulation of ICACC-1 as well. Patients with cystic fibrosis are hampered by lung disease characterized by thick secretions, which cause airway obstruction and subsequent colonization and infection by inhaled pathogenic microorganisms (Eng et al., 1996). Airway epithelia from cystic fibrosis patients exhibit a broad spectrum of ion transport properties that differ from normal including not only defective cAMP-mediated chloride secretion, but also increased sodium absorption and increased calcium-mediated chloride secretion (Johnson et al., 1995). Restoration of overall chloride secretion in primary cystic fibrosis airway epithelial cells leads to correction of sodium hyperabsorption and normal airway epithelial cell function (Johnson et al., 1995). Applicants therefore provide a method for treating cystic fibrosis by further increasing calcium-dependent chloride secretion in these cells through up-regulation of ICACC-1 activity in airway epithelia In this manner, the decrease in chloride secretion due to the defect in cAMP-mediated chloride secretion is compensated for through up-regulation of ICACC-1. The result being a restoration of the cellular chloride gradient and normal airway epithelial cell function. In another indication, up regulation of ICACC-1 will be useful for treating autoimmune associated diseases such as IBD.

As provided in the Examples, the proteins and nucleic acids of the invention, such as the ICACC-1 proteins having the amino acid sequence of SEQ ID NOS: 2 or 6, are induced by IL-9. Agents that modulate or down-regulate the expression of the protein or agents such as agonists or antagonists of at least one activity of the protein may be used to modulate biological and pathologic processes associated with the protein's function and activity. As used herein, a subject can be any mammal, so long as the mammal is in need of modulation of a pathological or biological process mediated by a protein of the invention.

The term "mammal" is meant an individual belonging to the class Mammalian The invention is particularly useful in the treatment of human subjects.

Pathological processes refer to a category of biological processes which produce a deleterious effect. For example, expression of a protein of the invention may be associated with atopic allergy, asthma and/or cystic fibrosis. As used herein, an agent is said to modulate a pathological process when the agent reduces the degree or severity of the process. For instance, atopic allergy, asthma and/or cystic fibrosis may be prevented or disease progression modulated by the administration of agents which reduce or modulate in some way the expression or at least one activity of a protein of the invention The agents of the present invention can be provided alone, or in combination with other agents that modulate a particular pathological process. For example, an agent of the present invention can be administered in combination with anti-asthma agents. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route or directly to the lungs. The dosage administered will be dependent upon the age, health, and weight of the recipient, kind of concurrent treatment, if any, frequency of treatment, and the nature of the effect desired.

The compounds used in the method of treatment of this invention may be administered systemically or topically, depending on such considerations as the condition to be treated, need for site-specific treatment, quantity of drug to be administered and similar considerations.

Topical administration may be used. Any common topical formation such as a solution, suspension, gel, ointment or salve and the like may be employed. Preparation of such topical formulations are well described in the art of pharmaceutical formulations as exemplified, for example, by *Remington's Pharmaceutical Sciences*. For topical application, these compounds could also be administered as a powder or spray, particularly in aerosol form. The active ingredient may be administered in pharmaceutical compositions adapted for systemic administration. As is known, if a drug is to be administered systemically, it may be confected as a powder, pill, tablet or the like or as a syrup or elixir for oral administration. For intravenous, intraperitoneal or intra-lesional administration, the compound will be prepared as a solution or suspension capable of being administered by injection. In certain cases, it may be useful to formulate these compounds in suppository form or as an extended release formulation for deposit under the skin or intramuscular injection. In a preferred embodiment, the compounds of this invention may be administered by inhalation. For inhalation therapy the compound may be in a solution useful for administration by metered dose inhalers or in a form suitable for a dry powder inhaler.

An effective amount is that amount which will downregulate ICACC-1. A given effective amount will vary from condition to condition and in certain instances may vary with the severity of the condition being treated and the patient's susceptibility to treatment. Accordingly, a given effective amount will be best determined at the time and place through routine experimentation. However, it is anticipated that in the treatment of atopic allergy and asthma-related disorders in accordance with the present invention, a formulation containing between 0.001 and 5 percent by weight, preferably about 0.01 to 1%, will usually constitute a therapeutically effective amount. When administered systemically, an amount between 0.01 and 100 mg per kg body weight per day, but preferably about 0.1 to 10 mg/kg, will effect a therapeutic result in most instances.

The invention also includes pharmaceutical compositions comprising the compounds of the invention together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in *Remington's Pharmaceutical Sciences,* Mack Publishing Company, 1995. In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice. The compounds of this invention can be utilized in vivo, ordinarily in mammals, preferably in humans.

In still another embodiment, the compounds of the invention may be coupled to chemical moieties, including proteins that alter the functions or regulation of ICACC-1 for therapeutic benefit in atopic allergy and asthma (Kreitman et al., 1994). These proteins may include in combination other inhibitors of cytokines and growth factors including anti-IL-4, anti-IL-5, anti-IL-3, anti-IL-2, anti-IL-13, anti-IL-11 and anti-IL-10 that may offer additional therapeutic benefit in atopic allergy and asthma In addition, the molecules of the invention may also be conjugated through phosphorylation to biotinylate, thioate, acetylate, iodinate using any of the cross-linking reagents well known in the art.

K. Diagnostics

Also included in the invention are methods of diagnosing susceptibility to atopic allergy and related disorders and for treating these disorders based on the relationship between IL-9, its receptor and ICACC-1.

These disorders also include the monitoring of ICACC-1 gene expression for the diagnosis of autoimmune disease of the bowel such as inflammatory bowel disease (IBD). In the case of IBD the lack or suppression of ICACC-1 gene expression would be a diagnostic marker for the disease and the ability to follow ICACC-1 levels would aid in monitoring treatment.

One diagnostic embodiment involves the recognition of variations in the DNA sequence of ICACC-1. One method involves the introduction of a nucleic acid molecule (also known as a probe) having a sequence complementary to ICACC-1 of the invention under sufficient hybridizing conditions, as would be understood by those in the art. In one embodiment, the sequence will bind specifically to one allele of ICACC-1 or a fragment thereof and in another embodiment will bind to both alleles. Another method of recognizing DNA sequence variation associated with these disorders is direct DNA sequence analysis by multiple methods well known in the art (Ott, 1991). Another embodiment involves the detection of DNA sequence variation in the ICACC-1 gene associated with these disorders (Schwengel et al., 1993; Sheffield et al., 1993; Orita et al., 1989; Sarkar et al., 1992; Cotton, 1989). These include the polymerase chain reaction, restriction fragment length polymorphism analysis and single stranded conformational analysis.

The practice of the present invention will employ the conventional terms and techniques of molecular biology, pharmacology, immunology and biochemistry that are within the ordinary skill of those in the art. For example, see Sambrook et al., *Molecular Cloning: A Laboratory Manual*, 2nd edition, Cold Spring Harbor Laboratory Press, 1985.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1 cDNA Difference Analysis of IL-9 Expressed Genes

Lungs extracted from transgenic IL-9 mice (Tg5) were used to isolate IL-9 induced genes. Tg5 is a FVB mouse overexpressing the IL-9 gene as previously described (Renauld et al., 1994). This strain has been shown to overexpress IL-9 in most tissues of the mouse. In order to identify specific IL-9 induced genes, suppressive PCR cDNA difference analysis was performed on mRNA from lungs of Tg5 mice and parental FVB mice using a commercially available PCR-select cDNA subtraction kit (Clonetech).

cDNA synthesis. Total RNA was prepared from lungs of FVB and Tg5 mice using Trizol as described by the manufacturer (Gibco/BRL). Lungs were removed from euthanized mice and frozen in liquid nitrogen. Frozen lungs were then placed in Trizol and pulverized using a tissue grinder. Polyadenylated RNA was purified from total RNA with oligo(dT) cellulose columns (Pharmacia). Double stranded cDNA was prepared using Superscript II reverse transcriptase and an oligo(dT) primer as suggested by the manufacturer (Clonetech). cDNA was then prepared by phenol-chloroform extraction and ethanol precipitation. Products were resuspended in nuclease-free water and analyzed on agarose gels to determine quality of products as described below.

cDNA difference analysis protocol. Differential cDNA analysis of Tg5 and FVB lungs was carried out following the manufacturers protocol (Clonetech) as depicted in FIG. 1. The results of the subtraction between the cDNA of these lungs resulted in the generation of 1200 recombinant clones. Analysis of these clones revealed multiples of several species, each accounting for 2–5% of the library. The most prominent transcript in the library was the IL-9 cDNA which served as a control for the efficiency of subtraction since it was a subtraction between an IL-9 constitutively expressing mouse (Tg5) and its parental control. Another cDNA which was found in multiple copies (represented 3% of library) was a novel calcium activated chloride channel which is described below.

Example 2

Identification of the Murine ICACC-1 cDNA in the Lung of IL-9 Transgenic Mice

ICACC-1 probes as described in Example 1 were used to probe a murine lung cDNA library (Clonetech) according to the manufacturers recommendation. One million recombinant clones were screened and several overlapping phage were identified. Subsequent screens enabled identification and isolation of a single plaque containing a phagemid which was then transformed into a double-stranded plasmid by phage rescue according to the manufacturers protocol. Recombinant clones were prepared and sequenced using primers directed to the plasmid vector as well as internal sequences identified from the partially subtracted probe. Clones were then aligned and contiged to generate the full-length sequence.

The 2931 bp cDNA isolated contained an open reading frame encoding a protein of 925 amino acids. FIG. 2 shows the nucleotide and amino acid sequence of the murine ICACC-1 cDNA. A nucleotide BLAST (Altschul et al., 1990) database search of GenBank with the full length cDNA revealed that it was similar to the bovine chloride channel protein. FIG. 3 shows an alignment to the bovine calcium activated chloride channel cDNA Motif analysis of the encoded polypeptide demonstrated several features such as multiple trismembrane regions and glycosylation sites. The primary sequence of murine ICACC-1 was used to perform an EST database search and several undescribed human ESTs were found to be homologous to small portions of the novel cDNA. FIGS. 4A and 4B show the sequences of the human ICACC-1 and ICACC-2 genes. Both full length human ICACC sequences were obtained by screening a human cDNA library.

Example 3

ICACC-1 is Induced in vivo by IL-9 in Murine Cells

To confirm that ICACC-1 is induced by IL-9 in the lung, RNA from the lungs of Tg5 and FVB mice were isolated as described in Example 1. cDNA was generated using random hexamers (Pharmacia) and Superscript II (Gibco/BRL) as suggested by the manufacturer. Message was analyzed by PCR as described (Nicolaides et al., 1995) and via Northern blot. Primers used to generate murine ICACC-1 message were; sense 5'-CCAGATCCACACCAAAACGAGAAG-3'

(SEQ ID NO:7) (nucleotides 689–712) and antisense 5'-CACTGTCAAAGGTCACCATCCCGA-3' (SEQ ID NO:8) (nucleotides 1041–1064) which produce a gene product of 376 bp. DHFR was assayed as an internal control to measure for cDNA integrity using primers previously described (Nicolaides et al., 1991). Amplification conditions used were 95° C. for 30 seconds, 58° C. for 1.5 minutes and 72° C. for 1.5 minutes for 35 cycles. For Northern blot analysis, total RNA derived from Tg5 or FVB lungs was electrophoresed on 1.5% formaldehyde gels, transferred to nylon membranes and probed with a DNA fragment comprising the murine ICACC-1 cDNA.

The results of the expression studies demonstrated that ICACC-1 is specifically expressed in the lung of the IL-9 transgenic mouse but not in the parental strain (FIG. 6). This data demonstrated a direct effect of IL-9 on ICACC-1 expression in the lung, where IL-9 responsive cells contained within the lung express ICACC-1.

Example 4

ICACC-1 Expression can be Induced in the Murine Lung by IL-9

ICACC-1 gene expression was assessed in vivo using the C57B6 mouse (bronchial hyporesponsive) which does not express detectable levels of IL-9 and the DBA mouse (bronchial hyperresponsive) which expresses robust levels of IL-9 (Nicolaides et al., 1997). RT-PCR and Northern blot analysis of ICACC-1 from these lungs demonstrated that ICACC-1 was expressed in the lung of mice which naturally express high levels of IL-9 (DBA) but not in those with low levels of IL-9 (C57B6) (FIG. 7).

To confirm that the expression of IL-9 was critically related to the expression of ICACC-1 and to control for genetic background specifically, recombinant murine IL-9 was introduced into the lung of murine strain C57B6. Recombinant IL9 was instilled into the trachea of anesthetized mice by addition of 50 µl of a 0.1 mg/ml IL-9 solution or vehicle alone (0.1% bovine serum albumin) daily for ten days. After ten days, the mice were euthanized and lungs extracted for either RNA expression analysis using Trizol as described by the manufacturer (Gibco/BRL) or Western blot analysis to determine levels of IL-9 instilled. The Western blot analysis for IL-9 demonstrated that direct addition of IL-9 to the lung resulted in an increase of overall amount of IL-9 in the lung while none was observed in the mouse instilled with vehicle alone.

Expression of ICACC-1 RNA was measured as described in Example 3. RT-PCR analysis for ICACC-1 RNA expression indicated that expression increased when recombinant IL-9 was administered to the lungs of the C57B6 mice, while no expression was observed in the lungs of mice treated with vehicle only (FIG. 8). This data demonstrates a direct role of IL-9 on inducing ICACC-1 expression in the lung.

Example 5

Tissue Distribution of ICACC-1 in Mice

To address the possibility that ICACC-1 expression occurs only in the presence of IL-9 expression, various organs were extracted from Tg5 mice and analyzed for RNA expression via Northern blot. BALBc mice were used as a control because they express low levels of IL-9 in the lung when compared to Tg5 mice. Tissue blots derived from BALBc murine organs were commercially obtained (Clonetech) while tissue blots for Tg5 murine organs were prepared by extracting organs followed by freezing in liquid nitrogen. Total RNA was extracted from each of these organs using Trizol as described by the manufacturer (Gibco/BRL). RNA was gel electrophoresed and analyzed as described in Example 4. Lanes were standardized by probing with β-actin as an internal control.

Tissue blots were probed using a DNA fragment comprising the ICACC-1 cDNA. As shown in FIG. 9 (bottom), no signal was observed in any of the tissues present on blots from normal mice. Analysis of ICACC-1 expression in Tg5 organs revealed expression in the lung, lymph node, colon, spleen, stomach, ovary and uterus (FIG. 9, top). This data demonstrated that ICACC-1 is expressed in several tissues in mice overexpressing IL9 but not in those with low IL-9 levels. This data suggests that ICACC-1 may play a role in the physiology of these organs in response to IL9.

Example 5A

Induction of ICACC-1 in the Lung by Exposure to Antigen

Figure 10A:
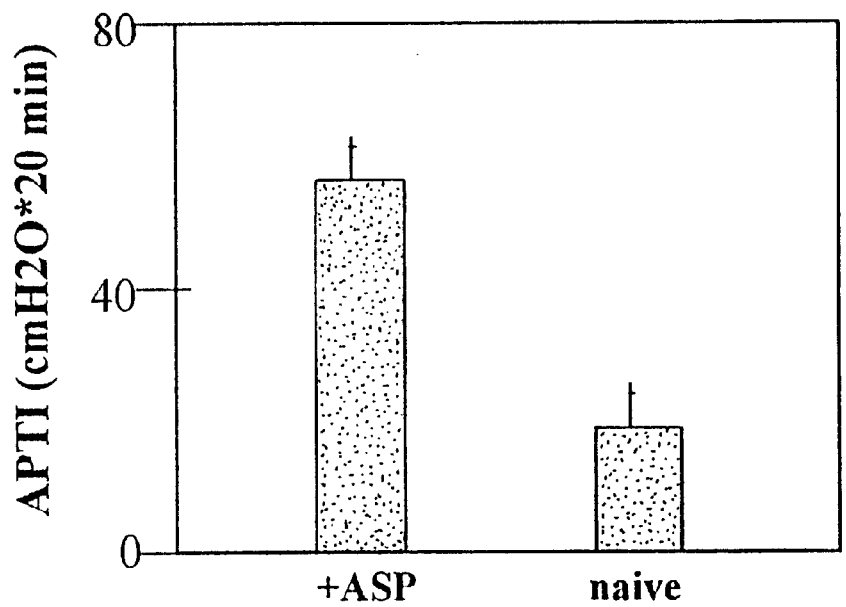
FIG. 10 shows *Aspergillus fumagatus*-antigen induced BHR and eosinophilia in Balb/C mice.
Figure 10B:
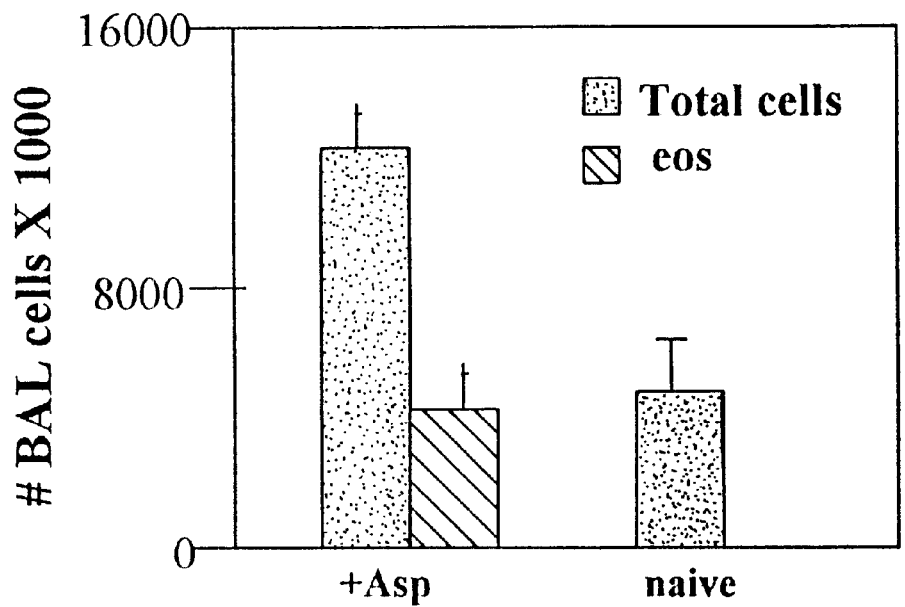
Figure 11:
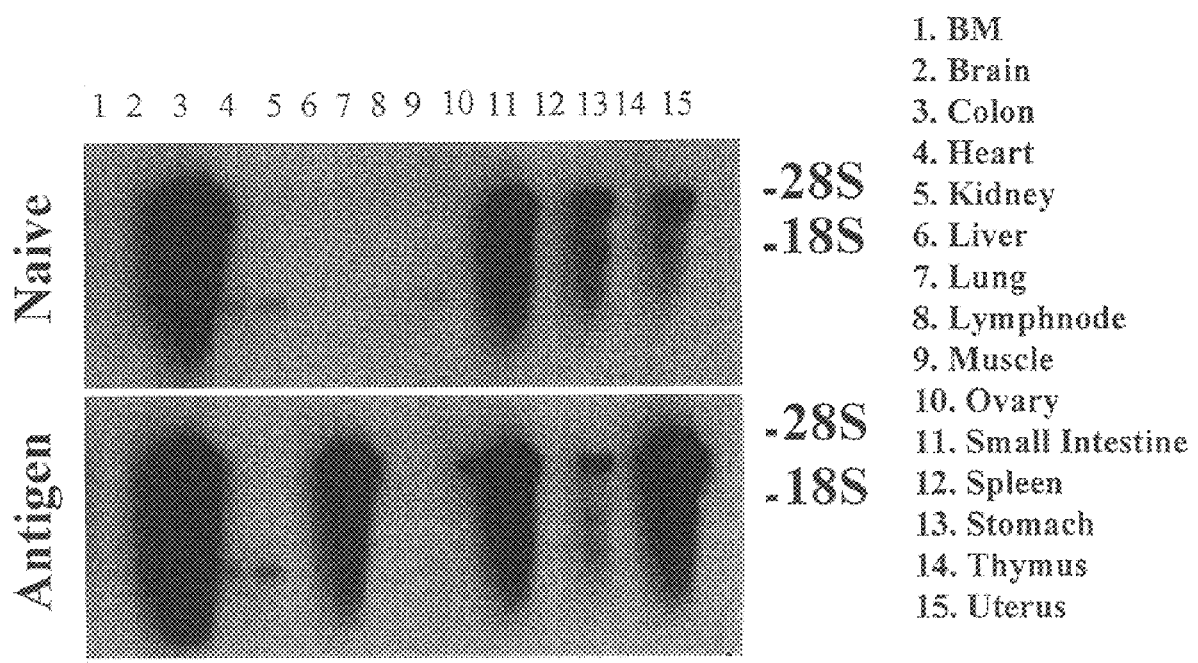
FIG. 11 shows the tissue distribution of ICACC-1 in naïve and antigen exposed Balb/C mice.

Antigen sensitzation and phenotyping of animals was carried out as previously described (McLane, M P, et al. Am. J. Respir. Cell Mol. Biol. 19:713–720, 1998). Briefly, Balb/C mice were intranasally exposed to *Aspergillus fumagatus* for 3–4 weeks. One day after the final exposure, antigen exposed mice and naïve controls were phenotyped for bronchial hyperresponsiveness (BHR) and cellularity in the airway. After phenotyping, organs were removed and total RNA was prepared as described in Example 5 and ICACC-1 expression was assessed in naïve and antigen treated tissues. As shown in FIG. 10, antigen exposed Balb/C mice had a significant increase in BHR (FIG. 10A) and inflammatory cell influx (the majority being eosinophils) as compared to controls (FIG. 10B). These features are very similar to clinical human asthma, and reinforce the notion that this is a relevant model to study molecular mechanisms and pharmaceutical target discovery for the development of asthma drugs. ICACC-1 gene expression was tightly associated with the asthmatic-like lung where robust expression was found in the antigen treated lung (bottom panel, FIG. 11), while no expression was found in the naïve "normal" lung ( top panel, FIG. 11). These data suggest that: 1) ICACC-1 is a potential therapeutic target for the treatment of asthma, and 2) inhibiting the expression or function of ICACC-1 will result in no toxic effects to the lung.

Example 5B

Inhibition of Antigen Induced Induction of ICACC-1 in the Lung with Anti-IL-9

IL-9 is a major mediator of the asthmatic response in man and mouse models of asthma (Nicolaides, et al. Proc. Natl. Acad. Sci. 94:13175–13180, 1997; McLane, M P, et al. Am. J. Respir. Cell Mol. Biol. 19:713–720, 1998; Temann et al., J. Exp. Med. 188:1307–1320, 1998: Levitt and Nicolaides, Emerg. Thera. Targets 3:1–11, 1999). The use of IL-9 blocking antibodies in antigen exposed mice suppresses the asthmatic-like phenotype (bronchial hyperresponsiveness and influx of inflammatory cells such as eosinophils). (B6D2)F1 mice were exposed to *Aspergillus fumagatus* antigen as described in Example 5A on day 0, 7, 14, 21, and 22. A subset of mice were also treated with 200 µgs of anti-mIL9 (Pharmingen hamster antimouse IL-9 ) intra nasally on day 0, 7, 14, and 21; or an isotype control Ig; or saline alone. All mice and naïve controls were phenotyped for BHR and BAL analysis as described in Example 5A. As shown in FIG. 12A, anti-IL9 treatment (Asp+α-mIL9) was able to significantly suppress BHR to levels near that of naïve, while isotype control Ig (Asp+Ig) had no effect on reducing BHR. A similar result was found for airway eosinophilia where a significant eosinophilia resulted upon antigen treatment (Asp−) that was suppressed by anti-mIL9 treatment (Asp+α-mIL9). Northern blot analysis of whole lungs from these mice showed that anti-mIL9 also suppressed ICACC-1 gene expression found in lungs of antigen exposed mice (FIG. 13). GADPH which is a ubiquitously expressed house keeping gene was used as a control to assure equal loading of RNA and overall gene expression. Together, these data demonstrate a tight correlation of ICACC-1 gene expression and the asthmatic response. These data suggest that blocking ICACC-1 expression or function would suppress the asthmatic response.

Example 6

ICACC1 Inducibility by IL-9 in Human Lung Epithelial Cells

To assess the ability of ICACC-1 to be induced by IL-9 in epithelial cells, the human primary lung epithelial cell line NHBE was assayed for expression levels of ICACC-1 in the presence of L-9. $1 \times 10^7$ cells were harvested and washed three times with phosphate-buffered saline and plated in medium in the presence or absence of 50 ng/ml IL-9 for 72 hours. Cells were then harvested and total RNA was extracted using Trizol as described by the manufacturer (Gibco/BRL). RNA was processed and reverse transcribed into cDNA as described in Example 3. Primers used to generate human ICACC-1 message were; sense 5'-GATTCCAGGAACAGCTAAGC-3' (SEQ ID NO:9) and antisense 5'-TATTTCATAGCTTGTAGCCTGG-3' (SEQ ID NO:10) which produce a gene product of 722 bp. γ-actin was assayed as an internal control to measure for cDNA integrity using primers previously described (Nicolaides et al., 1991). RT-PCR data derived from human lung epithelial cells, shows that ICACC-1 is induced in cells treated with IL-9 while no expression was observed in untreated cells, indicating that the cells expressing ICACC-1 directly respond to IL-9 (FIG. 14).

Furthermore, human primary lung cultures that were established from human lung biopsies were analyzed for IL-9 induced expression of ICACC-1. Lung tissues were first minced with scissors and passed through a wire mesh. Tissues were then digested with 175 iU/ml of collagenase (Sigma) for 1 hour at 37° C. Tissue was passed through 45 μm and 15 μm filters and then resuspended in Dubelco Iscove's medium, and plated into 10 cm tissue culture plates. Plates were incubated for 1 hour at 37° C. to allow macrophages to adhere to the plate and then non-adherent cells were harvested and resuspended at $2 \times 10^5$ cell/ml in Dulbelco Iscoive's medium supplemented with 10% FBS, antibiotics and cultured at 37° C. with 5% $CO_2$ for 4–5 days. For ICACC-1 IL-9 induction studies, cells were incubated for 4–5 days with or without 20 ng/ml recombinant human IL-9. Cells were then harvested and total RNA was extracted by trizol as described above. RNA was reverse transcribed and PCR'd for ICACC-1 using 5'-primer 5'-CCCAAAGGAAGCCAACTCTGA-3' (SEQ ID NO: 11) and 3' primer 5'-GTGAATGCCAGGAATGGTGCT-3' (SEQ ID NO:12) which resulted in a 253 bp product. PMS2 which is a ubiquitously expressed house keeping gene was used as an internal control as described (Nicolaides et al. Genomics 29: 329–334, 1995). Products were electrophoresed on 2% agarose gels and visualized by ethidium bromide staining. As shown in FIG. 15, IL-9 induced ICACC-1 expression in human primary lung cultures, while cultures grown in the absence of IL-9 had no detectable amounts of ICACC-1.

Example 6A

ICACC-1 Antiserum

Antisera were prepared to mICACC-1 by immunizing rabbits with peptides selected from the mICACC-1 sequence using methods described in Current Protocols in Immunology, Chapter 9, John Wiley & Sons, Inc. The peptides used for the immunizations were; residues 309–330, CLVLDKSGSMLNDDRLNRMNQA (SEQ ID NO:13), residues 357–375, QSELKQLNSGADRDLLIKHC (SEQ ID NO:14), residues 398–422, KKKYPTDGSEIV-LLTDGEDNTISSC (SEQ ID NO:15), residues 524–546, TTHPPTIFRWDPSGVEQNGFILDC (SEQ ID NO:16), residues 590–610, CPPITVTPVVNKNTGKFPSPVT (SEQ ID NO:17). The peptides were synthesized by standard techniques of automated peptide synthesis as either octavalent multiple antigen peptides (MAP) or as single peptides. The single peptides were coupled to KLH for immunization while the MAPs were used uncoupled. Rabbits were immunized with a mixture of all five peptides either as KLH conjugates or MAPs. Both immunogens produced useful antisera as indicated by their ability to immunoprecipitate MICACC-1.

Figure 16:
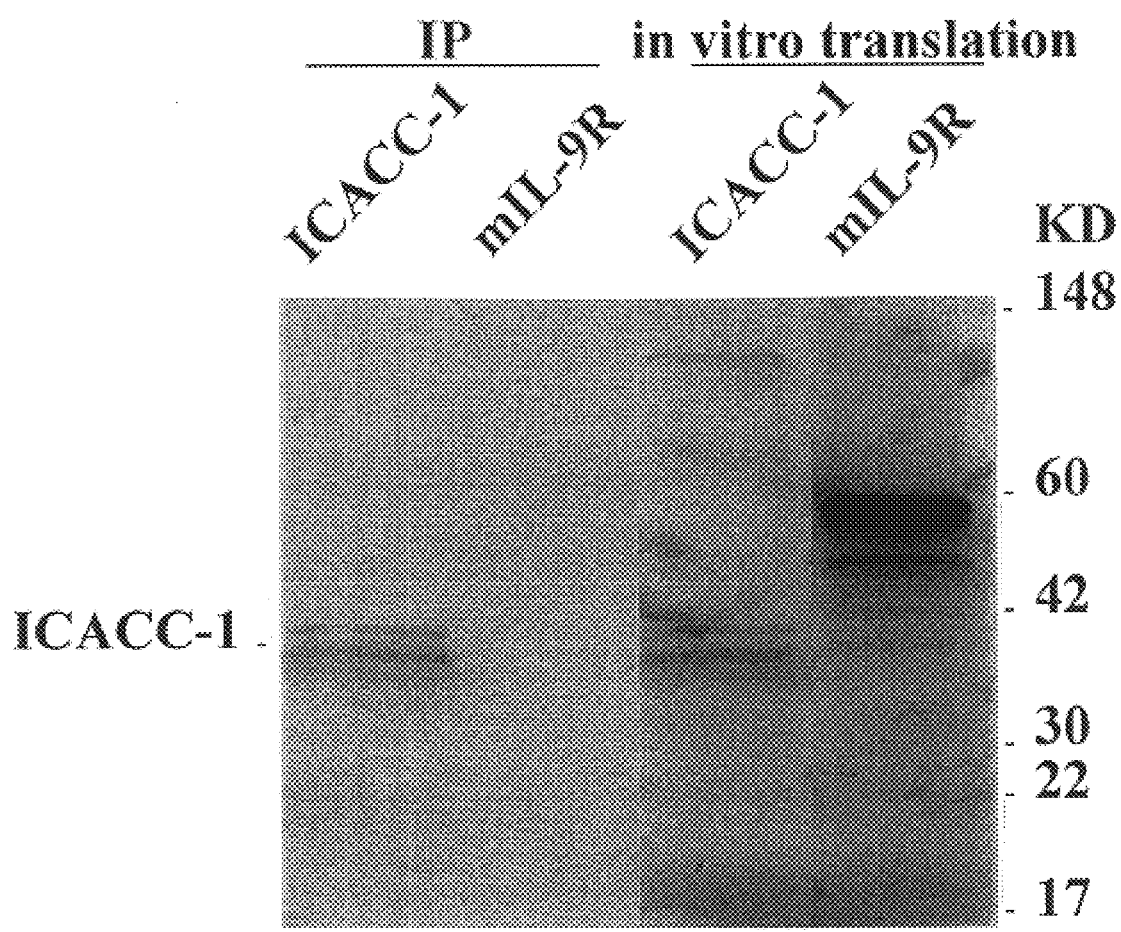
FIG. 16 shows antisera generated against ICACC-1 peptides is able to recognize native ICACC-1

Immunoprecipitation of in vitro translated ICACC-1 was performed to analyze the activities of these antibodies. A $^{35}S$ labeled ICACC-1 fragment (429 amino acids in length corresponding to amino acids 289–618 of the full length ICACC-1 ) was in vitro translated using TNT Coupled Reticulocyte Lysate Systems (Promega). Radio labeled ICACC-1 could be immunoprecipitated by 5 μl of ICACC-1 antisera or 1 μg of protein A purified polyclonal antibody. To assess the specificity of the ICACC-1 antisera, the $^{35}S$-labeled mIL-9 receptor fragment (60 KD mIL-9R) was used as a negative control. Under the same precipitation conditions, none of the mIL-9R protein was precipitated by the ICACC-1 antisera (FIG. 16). These results indicated that antisera and protein A purified polyclonal antibodies raised against ICACC-1 could recognize ICACC-1 and therefore could potentially be used as pharmaceutical reagents to block ICACC-1 function.

Example 6B

Figure 18:
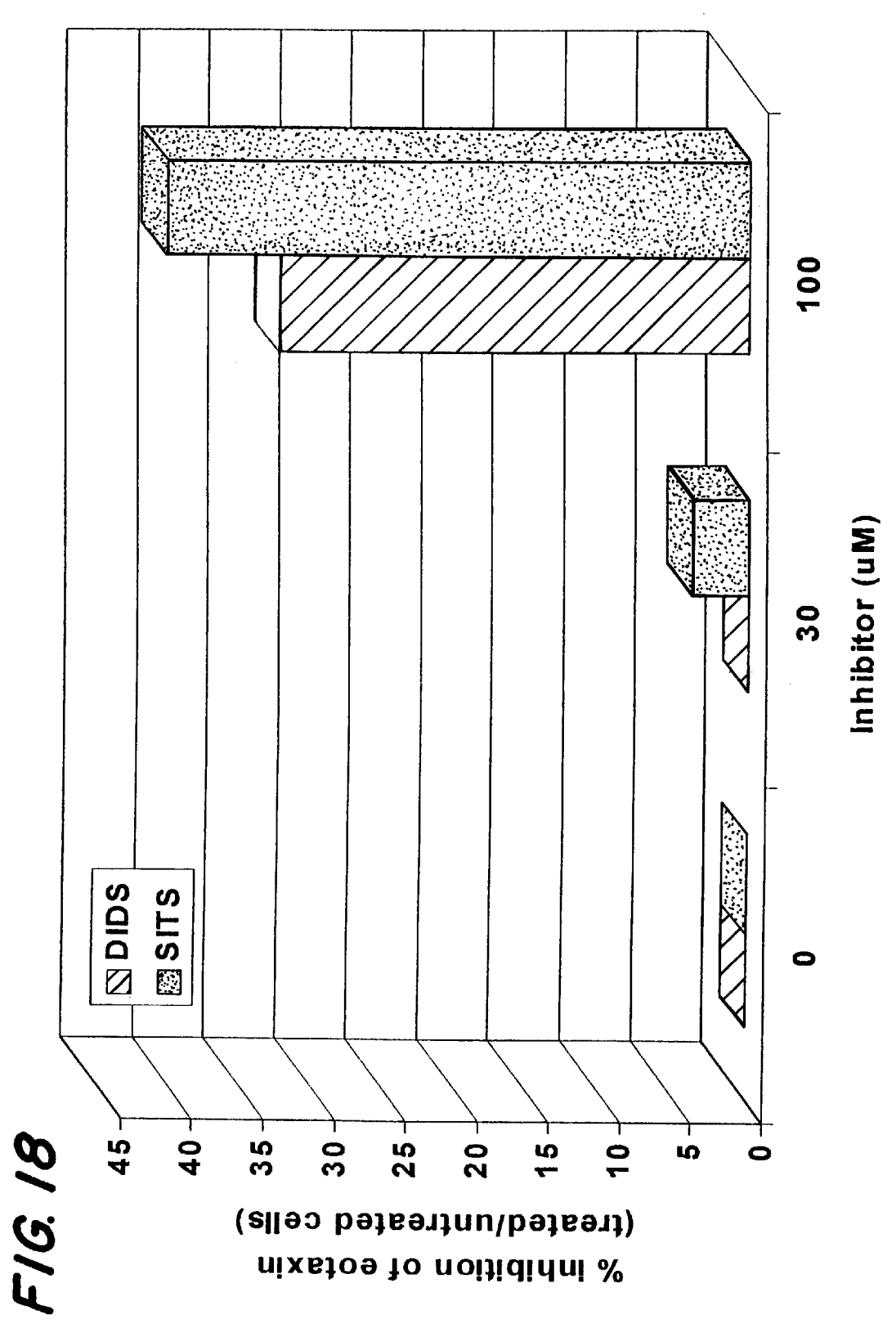

Suppression of IL-9 Induced Eotaxin Expression in the Lung using Chloride Channel Blockers IL-9 is known to induce eotaxin from lung epithelial cells (Dong, et.al., submitted for publication, Eur. J. Immunol.). In situ expression analysis of IL-9 transgenic mice found ICACC-1 expression to be predominant in airway epithelial cells. These epithelial cells also produce eotaxin, and eotaxin can be induced by IL-9 in these cells as well as primary lung cultures from a variety of different mouse strains. Because eotaxin and ICACC-1 are both induced by IL-9 in lung epithelial cells, it is possible that inhibiting ICACC-1 can inhibit eotaxin or other cytokines such as IL-4 or IL-13 (Doucet et al., J. Clin. Invest. 101:2129–2139, 1998.) that induce eotaxin production in lung epithelial cells. To test this hypothesis, we employed a murine primary lung assays, where lung cells were harvested from FVB/NJ mice as described in Example 5A and processed for in vitro analysis as described in Example 6 for human primary lung culture. Cells were incubated with or without 20 ng/ml recombinant mIL-9 for 48 hours. After 48 hours, conditioned supernatant was collected and analyzed for murine eotaxin production using an eotaxin ELISA kit (R&D Systems). Recombinant murine eotaxin was used to generate a standard curve. As shown in FIG. 17, FVB primary cells when cultured with IL-9 produce up to 2 ng/ml of eotaxin in contrast to nearly undetectable levels in FVB cultures grown in medium alone. A culture derived from IL-9 transgenic mouse lung (TG5 lane) was used as a positive control. This assay was used to assess the ability to suppress IL-9 induced eotaxin using chloride channel inhibitors DIDS and SITS. Cultures were plated with or without mIL-9 in the presence of 0, 30 $\mu$M and 100 $\mu$M channel blocker. As shown in FIG. 18, eotaxin production was inhibited 33% and 41% by 100 $\mu$M DIDS or SITS respectively. These data demonstrate the ability to suppress the biological function of IL-9 on epithelial cells by inhibiting chloride channel function. These data further indicate that suppression of a chloride channel such as the asthma associated ICACC-1 can result in a therapeutic benefit by the suppression of antigen induced asthmatic responses. This screening assay and technique can be used to evaluate other IL9 induced genes whose products are secreted proteins and is not restricted to using eotaxin as the only marker. A similar approach will be taken using the human ICACC-1 and human functional assays to identify "specific" chloride channel inhibitors that suppress: 1) IL-9 induced effects such as de novo gene expression, and 2) ICACC-1 biologic function(s).

Example 7

Specific Blocking of ICACC-1 Signaling in vivo by Small Molecule Inhibitors

To demonstrate the specificity of ICACC-1 signaling which is induced by IL-9, transfected cells expressing constitutively active ICACC-1 are treated with chloride channel blocking compounds to determine if inhibition of ICACC-1 blocks chloride channel activity. Cells transfected with a constitutively activated ICACC-1 gene are plated at 3000 cells/well in the presence or absence of IL-9 plus blocking compound and assessed for chloride channel activity using a fluorescent chloride probe. Wild-type cells do not exhibit the same amount of chloride channel activity as those constitutively expressing ICACC-1. The addition of the blocking compound on chloride channel activity is compared between wild-type cells and those expressing constitutively activated ICACC-1.

Example 8

Blocking of ICACC-1 Induction by Aminosterols in Murine Lung

Lungs from the DBA bronchial hyperresponsive mouse are treated with aminosterol compounds to test for their ability to block expression of ICACC-1. This group of aminosterols was identified from the liver of the dogfish shark as a class of molecules that appear to be antiproliferative. An example of these compounds are referred to in related U.S. patent application Ser. No. 08/290,826. This series of aminosterols are assayed for their ability to inhibit ICACC-1 expression and TH2 activity from the DBA mouse as described below.

DBA mice are injected daily intraperitoneally with various aminosterols at 10 mg/kg for 15 days. At day 15, mice are phenotyped (see Example 9), euthanized and lungs extracted as described in Example 1. RNA is isolated and processed for Northern blot analysis using a ICACC-1 cDNA probe. The level of ICACC-1 RNA detected by the probe indicates the extent of inhibition by aminosterols when compared to control. The ability of specific aminosterols, such as 1459, 1409, 1436 and 1569, to block the expression of ICACC-1 in vivo is assessed.

Example 9

Role of ICACC-1 in Murine Models of Asthma: Airway Response of Unsensitized Animals Certified virus-free male and female mice of the following strains, DBA, C57B6 and B6D2F1 are purchased from the National Cancer Institute or Jackson Laboratories (Bar Harbor Me.). IL-9 transgenic mice (Tg5) and their parent strain (FVB), are obtained from the Ludwig Institute (Brussels, Belgium). Animals are housed in high-efficiency particulate filtered air laminar flow hoods in a virus and antigen free facility and allowed free access to food and water for 3 to 7 days prior to experimental manipulation. The animal facilities are maintained at 22° C. and the light:dark cycle is automatically controlled (10:14 hour light:dark).

Phenotyping and efficacy of pretreatment. To determine the bronchoconstrictor response, respiratory system pressure is measured at the trachea and recorded before and during exposure to the drug. Mice are anesthetized and instrumented as previously described. (Levitt et al., 1988; Levitt et al., 1989; Kleeberger et al., 1990; Levitt et al., 1991; Levitt et al., 1995; Ewart et al., 1995). Airway responsiveness is measured to one or more of the following: 5-hydroxytryptamine, acetylcholine, atracurium or a substance-P analog. A simple and repeatable measure of the change in peak inspiratory pressure following bronchoconstrictor challenge is used which has been termed the Airway Pressure Time Index (APTI) (Levitt et al., 1988; Levitt et al., 1989). The APTI is assessed by the change in peak respiratory pressure integrated from the time of injection until the peak pressure returns to baseline or plateau. The APTI is comparable to airway resistance, however, the APTI includes an additional component related to the recovery from bronchoconstriction.

Prior to sacrifice, whole blood is collected for serum IgE measurements by needle puncture of the inferior vena cava in anesthetized animals. Samples are centrifuged to separate cells and serum is collected and used to measure total IgE levels. Samples not measured immediately are frozen at −20° C.

All IgE serum samples are measured using an ELISA antibody-sandwich assay. Microtiter plates are coated, 50 $\mu$l per well, with rat anti-murine IgE antibody (Southern Biotechnology) at a concentration of 2.5 $\mu$g/ml in a coating buffer of sodium carbonate-sodium bicarbonate with sodium azide. Plates are covered with plastic wrap and incubated at 4° C. for 16 hours. The plates are washed three times with a wash buffer of 0.05% Tween-20 in phosphate-buffered saline, incubating for five minutes for each wash. Blocking of nonspecific binding sites is accomplished by adding 200 $\mu$l per well 5% bovine serum albumin in phosphate-buffered saline, covering with plastic wrap and incubating for 2 hours at 37° C. After washing three times with wash buffer, duplicate 50 $\mu$l test samples are added to each well. Test samples are assayed after being diluted 1:10, 1:50 and 1:100 with 5% bovine serum albumin in wash buffer. In addition to the test samples, a set of IgE standards (PharMingen) at concentrations from 0.8 ng/ml to 200 ng/ml in 5% bovine serum albumin in wash buffer, are assayed to generate a standard curve. A blank of no sample or standard is used to zero the plate reader (background). After adding samples and standards, the plate is covered with plastic wrap and incubated for 2 hours at room temperature. After washing three times with wash buffer, 50 µl of secondary antibody rat anti-murine IgE-horseradish peroxidase conjugate is added at a concentration of 250 ng/ml in 5% bovine serum albumin in wash buffer. The plate is covered with plastic wrap and incubated 2 hours at room temperature. After washing three times with wash buffer, 100 µl of the substrate 0.5 mg/ml o-phenylenediamine in 0.1 M citrate buffer is added to every well. After 5-10 minutes the reaction is stopped with 50 µl of 12.5% sulfuric acid and absorbance is measured at 490 nm on a MR5000 plate reader (Dynatech). A standard curve is constructed from the standard IgE concentrations with antigen concentration on the x axis (log scale) and absorbance on the y axis (linear scale). The concentration of IgE in the samples is interpolated from the standard curve.

Bronchoalveolar lavage and cellular analysis are preformed as previously described (Kleeberger et al., 1990). Lung histology is carried out after the lungs are extracted. Since prior instrumentation may introduce artifact, separate animals are used for these studies. Thus, a small group of animals is treated in parallel exactly the same as the cohort undergoing various pretreatments except these animals are not used for other tests aside from bronchial responsiveness testing. After bronchial responsiveness testing, the lungs are removed and submersed in liquid nitrogen. Cryosectioning and histologic examination is carried out in a manner obvious to those skilled in the art.

Polyclonal antibodies which block the murine ICACC-1 pathway are used therapeutically to down-regulate the functions of, and assess the importance of this pathway to bronchial responsiveness, serum IgE and bronchoalveolar lavage in sensitized and unsensitized mice. After antibody pretreatment, baseline bronchial hyperresponsiveness, bronchoalveolar lavage and serum IgE levels relative to Ig matched controls are determined.

Example 10

Role of ICACC-1 in Murine Models of Asthma: Airway Response of Sensitized Animals The data of Example 6a demonstrate that antisera is able to be generated against ICACC-1 that recognizes the native protein structure as determined by the ability to recognize the protein in immunoprecipitation studies (FIG. 16). ICACC-1 blocking antibodies represent potential therapeutic agents in suppressing the function of ICACC-1. Studies are carried out using antigen sensitized animals and protocols as described Examples 5A, 5B, and 10. Animals are given ICACC-1 blocking antibodies via intranasal administration as described in example 5B and at day 23 animals are phenotyped for BHR, BAL, and immunoglobulin levels. The effect of pretreatment with ICACC-1 antibodies is used to assess the effect of down-regulating ICACC-1 on the asthma phenotype.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art.

REFERENCES

The following references are herein incorporated by reference in their entirety, as are all references, patents or patent applications referred to in this application:

Alexander A G, Barnes N C and Kay A B. Trial of cyclosporin in corticosteroid-dependent chronic severe asthma. *Lancet* 339, 324-328, 1992.

Altschul S F, Gish W, Miller W, Myers E W and Lipman D J. Basic Local alignment search tool. *J. Mol Biol.* 215, 403-410, 1990.

Burrows B, Sears M R, Flannery E M, Herbison G P and Holdaway M D. Relationship of bronchial responsiveness assessed by methacholine to serum IgE, lung function, symptoms and diagnoses in 11-year-old New Zealand children. *J. Allergy Clin. Immunol.* 90, 376–385, 1992.

Burrows B, Martinez F D, Halonen M, Barbee R A and Cline M G. Association of asthma with serum IgE levels and skin-test reactivity to allergens. *New Eng. J. Med* 320, 271–277, 1989.

Cotton R G. Detection of single base changes in nucleic acids. *Biochemical Journal* 263(1), 1–10, 1989.

Chu J W and Sharom F J. Glycophorin A interacts with interleukin-2 and inhibits interleukin-2-dependent T-lymphocyte proliferation. *Cell. Immunol.* 145, 223–239, 1992.

Clifford R D, Pugsley A, Radford M and Holgate S T. Symptoms, atopy and bronchial response to methacholine in parents with asthma and their children. *Arch. Dis. Childhood* 62, 66–73, 1987.

Cunningham S A, Awayda M S, Bubien J K, Ismailov I I, Arrate M P, Berdiev B K, Benos D J and Fuller C M. Cloning of an epithelial chloride channel from bovine trachea *J. Biol. Chem.* 270, 31016–31026, 1995.

Doull I, Lawrence S, Watson M, Begishvili T, Beasley R, Lampe F, Holgate S T and Morton N E. Allelic association of makers on chromosome 5q and 11q with atopy and bronchial hyperresponsiveness. *Am. J. Respir. Crit. Care Med.* 153, 1280–1284, 1996.

Dugas B, Renauld J C, Pene J, Bonnefoy J, Peti-Frere C, Braquet P, Bousquet J, Van Snick J, Mencia-Huerta J M. Interleukin-9 potentiates the interleukin-4-induced immunoglobulin (IgG, IgM and IgE) production by normal human B lymphocytes. *Eur. J. Immunol.* 23, 1687–1692, 1993.

Eklund K K, Ghildyal N, Austen K F and Stevens R L. Induction by IL-9 and suppression by IL-3 and IL4 of the levels of chromosome 14-derived transcripts that encode late-expressed mouse mast cell proteases. *J. Immunol.* 151, 4266–4273, 1993.

Eng P A, Morton J, Douglass J A, Riedler J, Wilson J and Robertson C F. Short-term efficacy of ultrasonically nebulized hypertonic saline in cystic fibrosis. *Pediatr Pulmonol.* 21, 77–83, 1996.

Ewart S, Levitt R C and Mitzner W. Respiratory system mechanics in mice measured by end-inflation occlusion. *J. Appl. Phs.* 79, 560–566, 1995.

Gergen P J and Weiss K B. The increasing problem of asthma in the United States. *Am. Rev. Respir. Dis.* 146, 823–824, 1992.

Gergen P J. The association of allergen skin test reactivity and respiratory disease among whites in the U.S. population. *Arch. Intern. Med.* 151. 487–492, 1991.

Halonen M, Stern D, Taussig L M, Wright A, Ray C G and Martinez F D. The predictive relationship between serum IgE levels at birth and subsequent incidences of lower respiratory illnesses and eczema in infants. *Am. Rev. Respir. Dis.* 146, 666–670, 1992.

Johannson S G O, Bennich H H and Berg T. The clinical significance of IgE. *Prog. Clin. Immunol.* 1, 1–25, 1972.

Johnson L G, Boyles S E, Wilson J and Boucher R C. Normalization of raised sodium absorption and raised calcium-mediated chloride secretion by adenovirus-mediated expression of cystic fibrosis transmembrane conductance regulator in primary human cystic fibrosis airway epithelial cells. *J Clin Invest* 95, 1377–1382, 1995.

Kauvar L M. Peptide mimetic drugs: A comment on progress and prospects. *Nature Biotechnology,* 14, 709, 1996.

Kleeberger S R, Bassett D J, Jakab G J and Levitt R C. A genetic model for evaluation of susceptibility to ozone-induced inflammation. *Am. J. Physiol.* 258, L313–320, 1990.

Kreitman R J, Puri R K, Leland P et al. Site-specific conjugation to interleukin-4 containing mutated cysteine residues produces interleukin 4-toxin conjugates with improved binding and activity. *Biochemistry* 33, 11637–11644, 1994.

Levitt R C and Ewart S L. Genetic susceptibility to atracurium-induced bronchoconstriction. *Am. J. Respir. Crit. Care. Med* 151, 1537–1542, 1995.

Levitt R C. Understanding biological variability in susceptibility to respiratory disease. *Pharmacogenetics* 1, 94–97, 1991.

Levitt R C and Mitzner W. Autosomal recessive inheritance of airway hyperreactivity to 5-hydroxytryptamine. *J. Appl. Physiol.* 67, 1125–1132, 1989.

Levitt R C, Mitzner W et al. Expression of airway hyperreactivity to acetylcholine as a simple autosomal recessive trait in mice. *FASEB J.* 2, 2605–2608, 1988.

Louahed J, Kermouni A, Van Snick J and Renauld J C. IL-9 induces expression of granzymes and high affinity IgE receptor in murine T helper clones. *J. Immunol.* 154, 5061–5070, 1995.

Marsh D G, Meyers D A and Bias W B. The epidemiology and genetics of atopic allergy. *New Eng. J. Med.* 305, 1551–1559, 1982.

Molinoff P et al., *Goodman and Gilman's The Pharmacologic Basis of Therapeutics,* MacMillan Publishing Company, New York N.Y., 1995.

Morely J. Cyclosporin A in asthma therapy: A pharmacological rationale. *J. Autoimmun.* 5 Suppl A, 265–269, 1992.

Nicolaides et al. IL9: A candidate gene for asthma *Proc. Natl. Acad. Sci. USA* 94, 13175–13180, 1997.

Nicolaides N C, Carter K C, Shell B K, Papadopoulos N, Vogelstein B and Kinzler K W. Genomic organization of the human PMS2 gene family. *Genomics* 30, 195–206, 1995.

Nicolaides N C, Gualdi R, Casadevall C, Manzella L, Calabretta B et al. Positive autoregulation of c-myb expression via Myb binding sites in the 5' flanking region of the human c-myb gene. *Mol. Cell. Biol.* 11, 6166–6176, 1991.

Orita M, Suzuki Y, Sekiya T and Hayashi K. Rapid and sensitive detection of point mutations and DNA polymorphisms using the polymerase chain reaction. *Genomics* 5, 874–879, 1989.

Ott J. *Analysis of human genetic linkage.* John Hopkins University Press, Baltimore Md., 1991.

Petit-Frere C, Dugas B, Braquet P, Mencia-Huerta J M. Interleukin-9 potentiates the interleukin-4 induced IgE and IgG1 release from murine B lymphocytes. *Immunology* 79, 146–151, 1993.

Renauld J C, van der Lugt N, Vink A, van Roon M, Godfraind C, Warnier G, Merz H, Feller A, Berns A and Van Snick J. Thymic lymphomas in interleukin 9 htransgenic mice. *Oncogene* 9, 1327–1332, 1994.

Sarkar G, Yoon H-S and Sommer S S. Dideoxy fingerprint (ddF): A rapid and efficient screen for the presence of mutations. *Genomics* 13, 441–443, 1992.

Schwengel D, Nouri N, Meyers D and Levitt R C. Linkage mapping of the human thromboxane A2 receptor (TBXA2R) to chromosome 19p13.3 using transcribed 3' untranslated DNA sequence polymorphisms. *Genomics* 18, 212–215, 1993.

Sears M R, Burrows B, Flannery E M, Herbison G P, Hewitt C J and Holdaway M D. Relation between airway responsiveness and serum IgE in children with asthma and in apparently normal children *New Engl. J. Med.* 325(15), 1067–1071, 1991.

Sheffield V C, Beck J S, Kwitek A E, Sandstrom D W and Stone E M. The sensitivity of single-strand conformation polymorphism analysis for the detection of single base substitutions. *Genomics* 16, 325–332, 1993.

Simoncsits A, Bristulf J, Tjornhammar M L et al. Deletion mutants of human interleukin 1 beta significantly reduced agonist properties: search for the agonist/antagonist switch in ligands to the interleukin 1 receptors. *Cytokine* 6, 206–214, 1994.

Zavyalov V P, Navolotskaya E V, Isaev I S et al. Nonapeptide corresponding to the sequence 27–35 of the mature human IL-2 efficiently competes with rIL-2 for binding to thymocyte receptors. *Immunol. Lett.* 31, 285–288, 1992.

What is claimed:

1. A method of identifying an agent which modulates an activity of a protein, wherein the protein comprises SEQ ID NO: 6, or a protein with at least 95 percent amino acid sequence identity to SEQ ID NO: 6 and which transports chloride ions across a membrane comprising:
   (a) exposing cells which express the protein to the agent; and
   (b) measuring chloride ion transport in the exposed cells, wherein a change in chloride ion transport compared to a control is indicative of an agent capable of modulating an activity of the protein.

2. The method of claim 1, wherein the control is a negative control comprising cells that do not express the protein.

3. The method of claim 1, wherein the control is a negative control comprising cells expressing the protein that have been contacted with a chloride channel blocker.

4. The method of claim 1, wherein the cells are eukaryotic or prokaryotic cells.

5. The method of claim 1, wherein the cells are yeast cells.

6. The method of claim 1, further comprising measuring expression of one or more proteins, wherein expression of the one or more proteins is associated with the activity of a protein comprising SEQ ID NO: 6 or a protein with at least 95 percent amino acid sequence identity to SEQ ID NO: 6.

7. The method of claim 6, wherein the protein is a chemokine.

8. The method of claim 7, wherein the chemokine is eotaxin.

9. The method of claim 6, wherein the protein is mucin.

10. The method of claim 1, farther comprising measuring tyrosine, threonine or serine phosphorylation.

11. The method of claim 1, further comprising measuring differentiation or proliferation of the cells.

12. The method of claim 11, wherein the cells are selected from the group consisting of mast cells, eosinophils, lymphocytes and epithelial cells.

13. The method of claim 1, wherein the agent is selected from the group consisting of chemical compounds, oligonucleotides, peptides and antibodies.

14. The method of claim 1, wherein the cells are disrupted subsequent to contact with the agent.

15. The method of claim 1 or 14, wherein the agent is labeled.

16. The method of claim 15, further comprising measuring binding of the labeled agent to said protein.

17. The method of claim 1, wherein the control is a positive control comprising cells expressing the protein that have been contacted with a cytokine.

18. The method of claim 17, wherein the cytokine is selected from the group consisting of IL-3, IL-4, IL-5, IL-9, IL-10, IL-11 and IL-13.

19. The method of claim 1, further comprising contacting the cells with a cytokine.

20. The method of claim 19, wherein the cytokine is selected from the group consisting of IL-3, IL-4, IL-5, IL-9, IL-10, IL-11 and IL-13.

21. The method of claim 19, further comprising measuring expression of one or more proteins by the cells contacted with the cytokine, wherein expression of the one or more proteins is associated with the activity of a protein comprising SEQ ID NO:6 or a protein with at least 95 percent amino acid sequence identity to SEQ ID NO:6.

22. The method of claim 21, wherein the chemokine is eotaxin.

23. The method of claim 1, wherein the cells are exposed to the agent in vitro.

24. The method of claim 23, wherein the cells are transfected with a nucleic acid encoding said protein.

25. The method of claim 24, wherein the nucleic acid comprises the nucleotide sequence of SEQ ID NO: 5.

26. The method of claim 24, wherein the nucleic acid consists of the nucleotide sequence of SEQ ID NO:5.

27. The method of claim 1 wherein the protein consists of the amino acid sequence of SEQ ID NO:6.

28. The method of claim 1, wherein said protein is labeled.

29. The method of claim 1, further comprising measuring acetylation of amino-terminal amino acid residues or lysine residues.

30. The method of claim 1, further comprising measuring methylation of homocysteine amino acid residues.

31. The method of claim 6, further comprising measuring expression of a protein comprising SEQ ID NO:6 or a protein with at least 95 percent amino acid sequence identity to SEQ ID) NO: 6.

32. The method of claim 21, further comprising measuring expression of a protein comprising SEQ ID NO:6 or a protein with at least 95 percent amino acid sequence identity to SEQ ID NO:6.

* * * * *

UNITED STATES PATENT AND TRADEMARK OFFICE
CERTIFICATE OF CORRECTION

| | |
|---|---|
| PATENT NO. | : 6,576,434 B1 |
| APPLICATION NO. | : 09/623624 |
| DATED | : June 10, 2003 |
| INVENTOR(S) | : Kenneth J. Holroyd et al. |

It is certified that error appears in the above-identified patent and that said Letters Patent is hereby corrected as shown below:

Column 78, line 16, replace "ID)" with --ID--.

In the sequence listing:

For SEQ ID NO: 6, at position 215, replace the amino acid "Xaa" with --Val--.

Signed and Sealed this

Eighteenth Day of November, 2008

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 2931
<212> TYPE: DNA
<213> ORGANISM: Mus musculus
<220> FEATURE:
<221> NAME/KEY: CDS
<222> LOCATION: (8)..(2746)

<400> SEQUENCE: 1
```

-continued

| | | |
|---|---|---|
| ctgcagg atg gaa tct ttg aag agt cct gtc ttc ctc ttg atc ctc cac<br>        Met Glu Ser Leu Lys Ser Pro Val Phe Leu Leu Ile Leu His<br>         1                    5                          10 | 49 |
| ctt ctg gaa gga gtt ctg agt gag tcc ctc atc caa ctg aac aac aac<br>Leu Leu Glu Gly Val Leu Ser Glu Ser Leu Ile Gln Leu Asn Asn Asn<br> 15                    20                   25                   30 | 97 |
| ggc tat gag ggc atc gtc atc gcc ata gac cac gac gtg ccg gaa gat<br>Gly Tyr Glu Gly Ile Val Ile Ala Ile Asp His Asp Val Pro Glu Asp<br>                35                    40                        45 | 145 |
| gaa gcc ctc att caa cac ata aag gac atg gtg act cag gcc tct cca<br>Glu Ala Leu Ile Gln His Ile Lys Asp Met Val Thr Gln Ala Ser Pro<br>           50                   55                   60 | 193 |
| tac ctg ttt gaa gct aca gga aaa aga ttt tac ttc aaa aat gtt gcc<br>Tyr Leu Phe Glu Ala Thr Gly Lys Arg Phe Tyr Phe Lys Asn Val Ala<br>        65                   70                   75 | 241 |
| att ttg att ccc gag agc tgg aag gca aag cct gaa tat acg agg cca<br>Ile Leu Ile Pro Glu Ser Trp Lys Ala Lys Pro Glu Tyr Thr Arg Pro<br>         80                   85                   90 | 289 |
| aaa ctt gaa acc ttc aaa aac gct gat gtc ctt gta tca aca acc agc<br>Lys Leu Glu Thr Phe Lys Asn Ala Asp Val Leu Val Ser Thr Thr Ser<br>95                  100                105                110 | 337 |
| cct cta ggc aat gat gag ccc tac acc gaa cat ata gga gca tgt gga<br>Pro Leu Gly Asn Asp Glu Pro Tyr Thr Glu His Ile Gly Ala Cys Gly<br>             115                  120                125 | 385 |
| gaa aag ggg atc agg att cac ctg act cct gac ttc tta gca gga aag<br>Glu Lys Gly Ile Arg Ile His Leu Thr Pro Asp Phe Leu Ala Gly Lys<br>          130                    135                140 | 433 |
| aag ctg act cag tat ggg cca caa gac agg acc ttt gtc cat gag tgg<br>Lys Leu Thr Gln Tyr Gly Pro Gln Asp Arg Thr Phe Val His Glu Trp<br>             145                  150                155 | 481 |
| gct cac ttc cga tgg gga gtg ttt aat gaa tac aac aac gac gag aag<br>Ala His Phe Arg Trp Gly Val Phe Asn Glu Tyr Asn Asn Asp Glu Lys<br>         160                  165                170 | 529 |
| ttc tac tta tcc aaa gga aaa ccc caa gca gtg agg tgt tca gca gcc<br>Phe Tyr Leu Ser Lys Gly Lys Pro Gln Ala Val Arg Cys Ser Ala Ala<br>175                  180                185                190 | 577 |
| att acc ggt aaa aat caa gtt cgt cgg tgc cag gga ggc agt tgt atc<br>Ile Thr Gly Lys Asn Gln Val Arg Arg Cys Gln Gly Gly Ser Cys Ile<br>             195                  200                205 | 625 |
| act aac gga aag tgt gta atc gac aga gta acg gga ctg tat aaa gac<br>Thr Asn Gly Lys Cys Val Ile Asp Arg Val Thr Gly Leu Tyr Lys Asp<br>          210                    215                220 | 673 |
| aat tgt gta ttt gta cca gat cca cac caa aac gag aag gct tcc atc<br>Asn Cys Val Phe Val Pro Asp Pro His Gln Asn Glu Lys Ala Ser Ile<br>             225                  230                235 | 721 |
| atg ttt aac caa aat atc aat tct gtg gtt gaa ttc tgt aca gaa aaa<br>Met Phe Asn Gln Asn Ile Asn Ser Val Val Glu Phe Cys Thr Glu Lys<br>         240                  245                250 | 769 |
| aat cac aat caa gaa gcc cca aat gac caa aac caa cga tgc aat ctc<br>Asn His Asn Gln Glu Ala Pro Asn Asp Gln Asn Gln Arg Cys Asn Leu<br>255                  260                265                270 | 817 |
| cga agc acg tgg gaa gtc atc cag gaa tct gag gac ttc aag caa acc<br>Arg Ser Thr Trp Glu Val Ile Gln Glu Ser Glu Asp Phe Lys Gln Thr<br>             275                  280                285 | 865 |
| act ccc atg aca gcc cag cca cct gca ccc acc ttc tca ctg ctg caa<br>Thr Pro Met Thr Ala Gln Pro Pro Ala Pro Thr Phe Ser Leu Leu Gln<br>          290                    295                300 | 913 |
| att gga caa aga att gtg tgc tta gtt ctt gat aag tcc ggg agc atg<br>Ile Gly Gln Arg Ile Val Cys Leu Val Leu Asp Lys Ser Gly Ser Met<br>         305                  310                315 | 961 |

```
ctg aac gat gat cgt ctt aac cga atg aat cag gca agc cgg ctt ttc    1009
Leu Asn Asp Asp Arg Leu Asn Arg Met Asn Gln Ala Ser Arg Leu Phe
        320                 325                 330 ctg ctg cag act gtg gag cag gga tcc tgg gtc ggg atg gtg acc ttt    1057
Leu Leu Gln Thr Val Glu Gln Gly Ser Trp Val Gly Met Val Thr Phe
335                 340                 345                 350 gac agt gct gcc tat gta caa agc gaa ctc aaa cag tta aac agt ggt    1105
Asp Ser Ala Ala Tyr Val Gln Ser Glu Leu Lys Gln Leu Asn Ser Gly
                355                 360                 365 gct gac aga gat ctg ctg atc aag cac tta ccc aca gta tct gca gga    1153
Ala Asp Arg Asp Leu Leu Ile Lys His Leu Pro Thr Val Ser Ala Gly
        370                 375                 380 ggg aca tct ata tgc tct ggc ctt cgg aca gca ttt aca gtg ata aag    1201
Gly Thr Ser Ile Cys Ser Gly Leu Arg Thr Ala Phe Thr Val Ile Lys
            385                 390                 395 aag aag tat cca act gat gga tct gaa att gtg ctg ctg acc gat ggg    1249
Lys Lys Tyr Pro Thr Asp Gly Ser Glu Ile Val Leu Leu Thr Asp Gly
400                 405                 410 gag gac aac acc att agc agc tgc ttt gac ctg gtg aag cag agc ggg    1297
Glu Asp Asn Thr Ile Ser Ser Cys Phe Asp Leu Val Lys Gln Ser Gly
415                 420                 425                 430 gcc atc atc cat aca gtg gcc ctg gga ccg gct gcc gct aaa gag ctt    1345
Ala Ile Ile His Thr Val Ala Leu Gly Pro Ala Ala Ala Lys Glu Leu
                435                 440                 445 gag cag ctg tcc aaa atg aca gga ggc ctg cag aca tac tct tcg gat    1393
Glu Gln Leu Ser Lys Met Thr Gly Gly Leu Gln Thr Tyr Ser Ser Asp
            450                 455                 460 cag gtt cag aac aat ggt ctt gtt gat gct ttc gca gca ctc tcc tca    1441
Gln Val Gln Asn Asn Gly Leu Val Asp Ala Phe Ala Ala Leu Ser Ser
465                 470                 475 gga aat gcg gcg atc gct cag cac tcc atc cag ctg gag agc agg gga    1489
Gly Asn Ala Ala Ile Ala Gln His Ser Ile Gln Leu Glu Ser Arg Gly
        480                 485                 490 gtt aat ctc cag aat aac caa tgg atg aat ggc tca gtg atc gtg gac    1537
Val Asn Leu Gln Asn Asn Gln Trp Met Asn Gly Ser Val Ile Val Asp
495                 500                 505                 510 agc tcg gtg ggc aag gac acc ttg ttt ctt atc acc tgg aca acg cat    1585
Ser Ser Val Gly Lys Asp Thr Leu Phe Leu Ile Thr Trp Thr Thr His
                515                 520                 525 cct cct aca ata ttt atc tgg gat ccc agc gga gtg gaa caa aat ggt    1633
Pro Pro Thr Ile Phe Ile Trp Asp Pro Ser Gly Val Glu Gln Asn Gly
            530                 535                 540 ttt ata cta gac aca acc act aag gtg gcc tac ctc caa gtc cca ggc    1681
Phe Ile Leu Asp Thr Thr Thr Lys Val Ala Tyr Leu Gln Val Pro Gly
545                 550                 555 acg gct aag gtt ggc ttt tgg aaa tac agc att caa gcg agc tca cag    1729
Thr Ala Lys Val Gly Phe Trp Lys Tyr Ser Ile Gln Ala Ser Ser Gln
        560                 565                 570 act ctc acc ttg act gtc acc tcc cgt gca gca agt gct aca ctg cct    1777
Thr Leu Thr Leu Thr Val Thr Ser Arg Ala Ala Ser Ala Thr Leu Pro
575                 580                 585                 590 cct att aca gtg acc ccg gta gtg aat aag aac aca ggg aaa ttc ccc    1825
Pro Ile Thr Val Thr Pro Val Val Asn Lys Asn Thr Gly Lys Phe Pro
                595                 600                 605 agc cct gta aca gtg tat gca agc att cgc caa gga gcc tcg cct att    1873
Ser Pro Val Thr Val Tyr Ala Ser Ile Arg Gln Gly Ala Ser Pro Ile
            610                 615                 620 ctc agg gcc agc gtc aca gcc ttg att gaa tct gtg aat gga aaa aca    1921
Leu Arg Ala Ser Val Thr Ala Leu Ile Glu Ser Val Asn Gly Lys Thr
```

```
              625                 630                 635
gta acc ctg gaa tta ctg gat aac gga gca ggt gcc gat gcc acc aag      1969
Val Thr Leu Glu Leu Leu Asp Asn Gly Ala Gly Ala Asp Ala Thr Lys
        640                 645                 650 aat gat ggt gtc tac tca agg ttt ttt aca gct ttt gat gca aat ggt      2017
Asn Asp Gly Val Tyr Ser Arg Phe Phe Thr Ala Phe Asp Ala Asn Gly
655                 660                 665                 670 aga tac agc gtt aaa ata tgg gct ctg gga gga gtc act tca gac aga      2065
Arg Tyr Ser Val Lys Ile Trp Ala Leu Gly Gly Val Thr Ser Asp Arg
                675                 680                 685 cag aga gca gca cct ccg aag aac aga gcc atg tac ata gat ggc tgg      2113
Gln Arg Ala Ala Pro Pro Lys Asn Arg Ala Met Tyr Ile Asp Gly Trp
        690                 695                 700 att gag gat ggt gaa gta aga atg aac cca cca cgt cct gaa act agt      2161
Ile Glu Asp Gly Glu Val Arg Met Asn Pro Pro Arg Pro Glu Thr Ser
        705                 710                 715 tat gtt caa gac aag cag ctg tgc ttc agc agg aca tct tca ggg gga      2209
Tyr Val Gln Asp Lys Gln Leu Cys Phe Ser Arg Thr Ser Ser Gly Gly
        720                 725                 730 tcg ttt gtg gcc acc aat gtc ccc gca gca gct ccc att cct gac ctc      2257
Ser Phe Val Ala Thr Asn Val Pro Ala Ala Ala Pro Ile Pro Asp Leu
735                 740                 745                 750 ttt cca ccc tgt caa atc act gac ctg aag gcc agc atc caa ggg cag      2305
Phe Pro Pro Cys Gln Ile Thr Asp Leu Lys Ala Ser Ile Gln Gly Gln
                755                 760                 765 aac ctg gtg aat ctg acg tgg acg gct cct ggg gat gac tac gac cac      2353
Asn Leu Val Asn Leu Thr Trp Thr Ala Pro Gly Asp Asp Tyr Asp His
            770                 775                 780 ggg aga gct tcc aac tac atc atc cga atg agc acc agt atc gtt gat      2401
Gly Arg Ala Ser Asn Tyr Ile Ile Arg Met Ser Thr Ser Ile Val Asp
        785                 790                 795 ctc agg gac cac ttc aac acc tca ctc caa gtg aac act acc ggt ctt      2449
Leu Arg Asp His Phe Asn Thr Ser Leu Gln Val Asn Thr Thr Gly Leu
        800                 805                 810 atc ccc aaa gag gcc agc tct gag gaa atc ttt gag ttt gaa ctg gga      2497
Ile Pro Lys Glu Ala Ser Ser Glu Glu Ile Phe Glu Phe Glu Leu Gly
815                 820                 825                 830 ggc aac act ttt gga aat ggc aca gat atc ttc att gct atc cag gct      2545
Gly Asn Thr Phe Gly Asn Gly Thr Asp Ile Phe Ile Ala Ile Gln Ala
                835                 840                 845 gtg gat aag tcc aat ctg aaa tca gaa atc tcc aac att gca cgg gtg      2593
Val Asp Lys Ser Asn Leu Lys Ser Glu Ile Ser Asn Ile Ala Arg Val
            850                 855                 860 tct gtg ttc atc ccc gct cag gag ccg ccc att ccc gaa gac tca act      2641
Ser Val Phe Ile Pro Ala Gln Glu Pro Pro Ile Pro Glu Asp Ser Thr
        865                 870                 875 ccc cct tgt cct gac atc agc atc aac agc acc att cct ggc atc cac      2689
Pro Pro Cys Pro Asp Ile Ser Ile Asn Ser Thr Ile Pro Gly Ile His
        880                 885                 890 gtg ctg aag ata atg tgg aag tgg cta ggg gaa atg cag gtg aca cta      2737
Val Leu Lys Ile Met Trp Lys Trp Leu Gly Glu Met Gln Val Thr Leu
895                 900                 905                 910 ggt ttg cac tgaattttca ggcaagaaat caaccagtca ttcctttcac              2786
Gly Leu His tggagaattt tctaaaaatg tactttagac ttcctgtagg gggcggtata gtaacactcg    2846
aagctgtaaa actgggtctg ggtgcattaa aaattatctg ttcaaataca aaaaaaaaa     2906 aaaaaaaaaa aaaaaaaaaa aaaaa                                          2931
```

-continued

```
<210> SEQ ID NO 2
<211> LENGTH: 913
<212> TYPE: PRT
<213> ORGANISM: Mus musculus

<400> SEQUENCE: 2
```

| | | | | | | | | | | | | | | |
|---|---|---|---|---|---|---|---|---|---|---|---|---|---|---|
| Met | Glu | Ser | Leu | Lys | Ser | Pro | Val | Phe | Leu | Leu | Ile | Leu | His | Leu | Leu |
| 1 | | | | 5 | | | | | 10 | | | | | 15 | |

| Glu | Gly | Val | Leu | Ser | Glu | Ser | Leu | Ile | Gln | Leu | Asn | Asn | Gly | Tyr |
|---|---|---|---|---|---|---|---|---|---|---|---|---|---|---|
| | | | 20 | | | | | 25 | | | | | 30 | |

| Glu | Gly | Ile | Val | Ile | Ala | Ile | Asp | His | Asp | Val | Pro | Glu | Asp | Glu | Ala |
| | | 35 | | | | | 40 | | | | | 45 | | | |

| Leu | Ile | Gln | His | Ile | Lys | Asp | Met | Val | Thr | Gln | Ala | Ser | Pro | Tyr | Leu |
| 50 | | | | | 55 | | | | | 60 | | | | | |

| Phe | Glu | Ala | Thr | Gly | Lys | Arg | Phe | Tyr | Phe | Lys | Asn | Val | Ala | Ile | Leu |
| 65 | | | | | 70 | | | | | 75 | | | | | 80 |

| Ile | Pro | Glu | Ser | Trp | Lys | Ala | Lys | Pro | Glu | Tyr | Thr | Arg | Pro | Lys | Leu |
| | | | | 85 | | | | | 90 | | | | | 95 | |

| Glu | Thr | Phe | Lys | Asn | Ala | Asp | Val | Leu | Val | Ser | Thr | Thr | Ser | Pro | Leu |
| | | | | 100 | | | | | 105 | | | | | 110 | |

| Gly | Asn | Asp | Glu | Pro | Tyr | Thr | Glu | His | Ile | Gly | Ala | Cys | Gly | Glu | Lys |
| | | | 115 | | | | | 120 | | | | | 125 | | |

| Gly | Ile | Arg | Ile | His | Leu | Thr | Pro | Asp | Phe | Leu | Ala | Gly | Lys | Lys | Leu |
| | 130 | | | | | 135 | | | | | 140 | | | | |

| Thr | Gln | Tyr | Gly | Pro | Gln | Asp | Arg | Thr | Phe | Val | His | Glu | Trp | Ala | His |
| 145 | | | | | 150 | | | | | 155 | | | | | 160 |

| Phe | Arg | Trp | Gly | Val | Phe | Asn | Glu | Tyr | Asn | Asn | Asp | Glu | Lys | Phe | Tyr |
| | | | | 165 | | | | | 170 | | | | | 175 | |

| Leu | Ser | Lys | Gly | Lys | Pro | Gln | Ala | Val | Arg | Cys | Ser | Ala | Ala | Ile | Thr |
| | | | 180 | | | | | 185 | | | | | 190 | | |

| Gly | Lys | Asn | Gln | Val | Arg | Arg | Cys | Gln | Gly | Gly | Ser | Cys | Ile | Thr | Asn |
| | 195 | | | | | 200 | | | | | 205 | | | | |

| Gly | Lys | Cys | Val | Ile | Asp | Arg | Val | Thr | Gly | Leu | Tyr | Lys | Asp | Asn | Cys |
| 210 | | | | | 215 | | | | | 220 | | | | | |

| Val | Phe | Val | Pro | Asp | Pro | His | Gln | Asn | Glu | Lys | Ala | Ser | Ile | Met | Phe |
| 225 | | | | | 230 | | | | | 235 | | | | | 240 |

| Asn | Gln | Asn | Ile | Asn | Ser | Val | Val | Glu | Phe | Cys | Thr | Glu | Lys | Asn | His |
| | | | | 245 | | | | | 250 | | | | | 255 | |

| Asn | Gln | Glu | Ala | Pro | Asn | Asp | Gln | Asn | Gln | Arg | Cys | Asn | Leu | Arg | Ser |
| | | | 260 | | | | | 265 | | | | | 270 | | |

| Thr | Trp | Glu | Val | Ile | Gln | Glu | Ser | Glu | Asp | Phe | Lys | Gln | Thr | Thr | Pro |
| | 275 | | | | | 280 | | | | | 285 | | | | |

| Met | Thr | Ala | Gln | Pro | Pro | Ala | Pro | Thr | Phe | Ser | Leu | Leu | Gln | Ile | Gly |
| 290 | | | | | 295 | | | | | 300 | | | | | |

| Gln | Arg | Ile | Val | Cys | Leu | Val | Leu | Asp | Lys | Ser | Gly | Ser | Met | Leu | Asn |
| 305 | | | | | 310 | | | | | 315 | | | | | 320 |

| Asp | Asp | Arg | Leu | Asn | Arg | Met | Asn | Gln | Ala | Ser | Arg | Leu | Phe | Leu | Leu |
| | | | | 325 | | | | | 330 | | | | | 335 | |

| Gln | Thr | Val | Glu | Gln | Gly | Ser | Trp | Val | Gly | Met | Val | Thr | Phe | Asp | Ser |
| | | | 340 | | | | | 345 | | | | | 350 | | |

| Ala | Ala | Tyr | Val | Gln | Ser | Glu | Leu | Lys | Gln | Leu | Asn | Ser | Gly | Ala | Asp |
| | | 355 | | | | | 360 | | | | | 365 | | | |

| Arg | Asp | Leu | Leu | Ile | Lys | His | Leu | Pro | Thr | Val | Ser | Ala | Gly | Gly | Thr |
| | 370 | | | | | 375 | | | | | 380 | | | | |

-continued

```
Ser Ile Cys Ser Gly Leu Arg Thr Ala Phe Thr Val Ile Lys Lys Lys
385                 390                 395                 400

Tyr Pro Thr Asp Gly Ser Glu Ile Val Leu Leu Thr Asp Gly Glu Asp
                405                 410                 415

Asn Thr Ile Ser Ser Cys Phe Asp Leu Val Lys Gln Ser Gly Ala Ile
                420                 425                 430

Ile His Thr Val Ala Leu Gly Pro Ala Ala Lys Glu Leu Glu Gln
                435                 440                 445

Leu Ser Lys Met Thr Gly Gly Leu Gln Thr Tyr Ser Ser Asp Gln Val
    450                 455                 460

Gln Asn Asn Gly Leu Val Asp Ala Phe Ala Ala Leu Ser Ser Gly Asn
465                 470                 475                 480

Ala Ala Ile Ala Gln His Ser Ile Gln Leu Glu Ser Arg Gly Val Asn
                485                 490                 495

Leu Gln Asn Asn Gln Trp Met Asn Gly Ser Val Ile Val Asp Ser Ser
                500                 505                 510

Val Gly Lys Asp Thr Leu Phe Leu Ile Thr Trp Thr Thr His Pro Pro
    515                 520                 525

Thr Ile Phe Ile Trp Asp Pro Ser Gly Val Glu Gln Asn Gly Phe Ile
    530                 535                 540

Leu Asp Thr Thr Thr Lys Val Ala Tyr Leu Gln Val Pro Gly Thr Ala
545                 550                 555                 560

Lys Val Gly Phe Trp Lys Tyr Ser Ile Gln Ala Ser Ser Gln Thr Leu
                565                 570                 575

Thr Leu Thr Val Thr Ser Arg Ala Ala Ser Ala Thr Leu Pro Pro Ile
                580                 585                 590

Thr Val Thr Pro Val Val Asn Lys Asn Thr Gly Lys Phe Pro Ser Pro
                595                 600                 605

Val Thr Val Tyr Ala Ser Ile Arg Gln Gly Ala Ser Pro Ile Leu Arg
                610                 615                 620

Ala Ser Val Thr Ala Leu Ile Glu Ser Val Asn Gly Lys Thr Val Thr
625                 630                 635                 640

Leu Glu Leu Leu Asp Asn Gly Ala Gly Ala Asp Ala Thr Lys Asn Asp
                645                 650                 655

Gly Val Tyr Ser Arg Phe Phe Thr Ala Phe Asp Ala Asn Gly Arg Tyr
                660                 665                 670

Ser Val Lys Ile Trp Ala Leu Gly Gly Val Thr Ser Asp Arg Gln Arg
                675                 680                 685

Ala Ala Pro Pro Lys Asn Arg Ala Met Tyr Ile Asp Gly Trp Ile Glu
    690                 695                 700

Asp Gly Glu Val Arg Met Asn Pro Pro Arg Pro Glu Thr Ser Tyr Val
705                 710                 715                 720

Gln Asp Lys Gln Leu Cys Phe Ser Arg Thr Ser Gly Gly Ser Phe
                725                 730                 735

Val Ala Thr Asn Val Pro Ala Ala Pro Ile Pro Asp Leu Phe Pro
                740                 745                 750

Pro Cys Gln Ile Thr Asp Leu Lys Ala Ser Ile Gln Gly Gln Asn Leu
                755                 760                 765

Val Asn Leu Thr Trp Thr Ala Pro Gly Asp Asp Tyr Asp His Gly Arg
    770                 775                 780

Ala Ser Asn Tyr Ile Ile Arg Met Ser Thr Ser Ile Val Asp Leu Arg
785                 790                 795                 800
```

-continued

```
Asp His Phe Asn Thr Ser Leu Gln Val Asn Thr Thr Gly Leu Ile Pro
            805                 810                 815
Lys Glu Ala Ser Ser Glu Glu Ile Phe Glu Phe Glu Leu Gly Gly Asn
        820                 825                 830
Thr Phe Gly Asn Gly Thr Asp Ile Phe Ile Ala Ile Gln Ala Val Asp
            835                 840                 845
Lys Ser Asn Leu Lys Ser Glu Ile Ser Asn Ile Ala Arg Val Ser Val
    850                 855                 860
Phe Ile Pro Ala Gln Glu Pro Ile Pro Glu Asp Ser Thr Pro Pro
865                 870                 875                 880
Cys Pro Asp Ile Ser Ile Asn Ser Thr Ile Pro Gly Ile His Val Leu
            885                 890                 895
Lys Ile Met Trp Lys Trp Leu Gly Glu Met Gln Val Thr Leu Gly Leu
            900                 905                 910
His
```

<210> SEQ ID NO 3
<211> LENGTH: 3190
<212> TYPE: DNA
<213> ORGANISM: Homo sapiens
<220> FEATURE:
<221> NAME/KEY: CDS
<222> LOCATION: (120)..(2948)

<400> SEQUENCE: 3

```
cttcttgtgt tcttaaaccc ttgcaagttc agraagaaac ccatctgcat ccatattgaa        60
aacctgacac aatgtatgca gcaggctcag tgtgagtgaa ctggaggctt ctctacaac       119 atg acc caa agg agc att gca ggt cct att tgc aac ctg aag ttt gtg       167
Met Thr Gln Arg Ser Ile Ala Gly Pro Ile Cys Asn Leu Lys Phe Val
  1               5                  10                  15 act ctc ctg gtt gcc tta agt tca gaa ctc cca ttc ctg gga gct gga       215
Thr Leu Leu Val Ala Leu Ser Ser Glu Leu Pro Phe Leu Gly Ala Gly
                 20                  25                  30 gta cag ctt caa gac aat ggg tat aat gga ttg ctc att gca att aat       263
Val Gln Leu Gln Asp Asn Gly Tyr Asn Gly Leu Leu Ile Ala Ile Asn
             35                  40                  45 cct cag gta cct gag aat cag aac ctc atc tca aac att aag gaa atg       311
Pro Gln Val Pro Glu Asn Gln Asn Leu Ile Ser Asn Ile Lys Glu Met
         50                  55                  60 ata act gaa gct tca ttt tac cta ttt aat gct acc aag aga aga gta       359
Ile Thr Glu Ala Ser Phe Tyr Leu Phe Asn Ala Thr Lys Arg Arg Val
 65                  70                  75                  80 ttt ttc aga aat ata aag att tta ata cct gcc aca tgg aaa gct aat       407
Phe Phe Arg Asn Ile Lys Ile Leu Ile Pro Ala Thr Trp Lys Ala Asn
                 85                  90                  95 aat aac agc aaa ata aaa caa gaa tca tat gaa aag gca aat gtc ata       455
Asn Asn Ser Lys Ile Lys Gln Glu Ser Tyr Glu Lys Ala Asn Val Ile
            100                 105                 110 gtg act gac tgg tat agg gca cat gga gat gat cca tac acc cta caa       503
Val Thr Asp Trp Tyr Arg Ala His Gly Asp Asp Pro Tyr Thr Leu Gln
        115                 120                 125 tac aga ggg tgt gga aaa gag gga aaa tac att cat ttc aca cct aat       551
Tyr Arg Gly Cys Gly Lys Glu Gly Lys Tyr Ile His Phe Thr Pro Asn
    130                 135                 140 ttc cta ctg aat gat aac tta aca gct ggc tac gga tca cga ggc cga       599
Phe Leu Leu Asn Asp Asn Leu Thr Ala Gly Tyr Gly Ser Arg Gly Arg
145                 150                 155                 160 gtg ttt gtc cat gaa tgg gcc cac ctc cgt tgg ggt gtg ttc gat gag       647
```

```
Val Phe Val His Glu Trp Ala His Leu Arg Trp Gly Val Phe Asp Glu
            165                 170                 175 tat aac aat gac aaa cct ttc tac ata aat ggg caa aat caa att aaa      695
Tyr Asn Asn Asp Lys Pro Phe Tyr Ile Asn Gly Gln Asn Gln Ile Lys
        180                 185                 190 gtg aca agg tgt tca tct gac atc aca ggc att ttt gtg tgt gaa aaa      743
Val Thr Arg Cys Ser Ser Asp Ile Thr Gly Ile Phe Val Cys Glu Lys
            195                 200                 205 ggt cct tgc ccc caa gaa aac tgt att att agt aag ctt ttt aaa gaa      791
Gly Pro Cys Pro Gln Glu Asn Cys Ile Ile Ser Lys Leu Phe Lys Glu
    210                 215                 220 gga tgc acc ttt atc tac aat agc acc caa agt gca act gca tca ata      839
Gly Cys Thr Phe Ile Tyr Asn Ser Thr Gln Ser Ala Thr Ala Ser Ile
225                 230                 235                 240 atg ttc atg cga agt tta tct tct gtg gtt gaa ttt tgt aat gca agt      887
Met Phe Met Arg Ser Leu Ser Ser Val Val Glu Phe Cys Asn Ala Ser
                245                 250                 255 acc cac aac caa gaa gca cca aac cta cag aac cag atg tgc agc ctc      935
Thr His Asn Gln Glu Ala Pro Asn Leu Gln Asn Gln Met Cys Ser Leu
            260                 265                 270 aga agt gca tgg gat gta atc aca gac tct gct gac ttt cac cac agc      983
Arg Ser Ala Trp Asp Val Ile Thr Asp Ser Ala Asp Phe His His Ser
        275                 280                 285 ttt ccc atg aac ggg act gag ctt cca cct cct ccc aca ttc tcg ctt     1031
Phe Pro Met Asn Gly Thr Glu Leu Pro Pro Pro Pro Thr Phe Ser Leu
    290                 295                 300 gta gag gct ggt gac aaa gtg gtc tgt tta gtg ctg gat gcg tcc agc     1079
Val Glu Ala Gly Asp Lys Val Val Cys Leu Val Leu Asp Ala Ser Ser
305                 310                 315                 320 aag atg gca gag gct gac aga ctc ctt caa cta caa caa gcc gca gaa     1127
Lys Met Ala Glu Ala Asp Arg Leu Leu Gln Leu Gln Gln Ala Ala Glu
                325                 330                 335 ttt tat ttg atg cag att gtt gaa att cat acc ttc gtg ggc att gcc     1175
Phe Tyr Leu Met Gln Ile Val Glu Ile His Thr Phe Val Gly Ile Ala
            340                 345                 350 agt ttc gac agc aaa gga gag atc aga gcc cag cta cac caa att aac     1223
Ser Phe Asp Ser Lys Gly Glu Ile Arg Ala Gln Leu His Gln Ile Asn
        355                 360                 365 agc aat gat gat cga aag ttg ctg gtt tca tat ctg ccc acc act gta     1271
Ser Asn Asp Asp Arg Lys Leu Leu Val Ser Tyr Leu Pro Thr Thr Val
    370                 375                 380 tca gct aaa aca gac atc agc att tgt agc ggg ctt aag aaa gga ttt     1319
Ser Ala Lys Thr Asp Ile Ser Ile Cys Ser Gly Leu Lys Lys Gly Phe
385                 390                 395                 400 gag gtg gtt gaa aaa ctg aat gga aaa gct tat ggc tct gtg atg ata     1367
Glu Val Val Glu Lys Leu Asn Gly Lys Ala Tyr Gly Ser Val Met Ile
                405                 410                 415 tta gtg acc agc gga gat gat aag ctt ctt ggc aat tgc tta ccc act     1415
Leu Val Thr Ser Gly Asp Asp Lys Leu Leu Gly Asn Cys Leu Pro Thr
            420                 425                 430 gtg ctc agc agt ggt tca aca att cac tcc att gcc ctg ggt tca tct     1463
Val Leu Ser Ser Gly Ser Thr Ile His Ser Ile Ala Leu Gly Ser Ser
        435                 440                 445 gca gcc cca aat ctg gag gaa tta tca cgt ctt aca gga ggt tta aag     1511
Ala Ala Pro Asn Leu Glu Glu Leu Ser Arg Leu Thr Gly Gly Leu Lys
    450                 455                 460 ttc ttt gtt cca gat ata tca aac tcc aat agc atg att gat gct ttc     1559
Phe Phe Val Pro Asp Ile Ser Asn Ser Asn Ser Met Ile Asp Ala Phe
465                 470                 475                 480
```

```
agt aga att tcc tct gga act gga gac att ttc cag caa cat att cag    1607
Ser Arg Ile Ser Ser Gly Thr Gly Asp Ile Phe Gln Gln His Ile Gln
            485                 490                 495 ctt gaa agt aca ggt gaa aat gtc aaa cct cac cat caa ttg aaa aac    1655
Leu Glu Ser Thr Gly Glu Asn Val Lys Pro His His Gln Leu Lys Asn
        500                 505                 510 aca gtg act gtg gat aat act gtg ggc aac gac act atg ttt cta gtt    1703
Thr Val Thr Val Asp Asn Thr Val Gly Asn Asp Thr Met Phe Leu Val
    515                 520                 525 acg tgg cag gcc agt ggt cct cct gag att ata tta ttt gat cct gat    1751
Thr Trp Gln Ala Ser Gly Pro Pro Glu Ile Ile Leu Phe Asp Pro Asp
530                 535                 540 gga cga aaa tac tac aca aat aat ttt atc acc aat cta act ttt cgg    1799
Gly Arg Lys Tyr Tyr Thr Asn Asn Phe Ile Thr Asn Leu Thr Phe Arg
545                 550                 555                 560 aca gct agt ctt tgg att cca gga aca gct aag cct ggg cac tgg act    1847
Thr Ala Ser Leu Trp Ile Pro Gly Thr Ala Lys Pro Gly His Trp Thr
            565                 570                 575 tac acc ctg aac aat acc cat cat tct ctg caa gcc ctg aaa gtg aca    1895
Tyr Thr Leu Asn Asn Thr His His Ser Leu Gln Ala Leu Lys Val Thr
        580                 585                 590 gtg acc tct cgt gcc tcc aac tca gct gtg ccc cca gcc act gtg gaa    1943
Val Thr Ser Arg Ala Ser Asn Ser Ala Val Pro Pro Ala Thr Val Glu
    595                 600                 605 gcc ttt gtg gaa aga gac agc ctc cat ttt cct cat cct gtg atg att    1991
Ala Phe Val Glu Arg Asp Ser Leu His Phe Pro His Pro Val Met Ile
610                 615                 620 tat gcc aat gtg aaa cag gga ttt tat ccc att ctt aat gcc act gtc    2039
Tyr Ala Asn Val Lys Gln Gly Phe Tyr Pro Ile Leu Asn Ala Thr Val
625                 630                 635                 640 act gcc aca gtt gag cca gag act gga gat cct gtt acg ctg aga ctc    2087
Thr Ala Thr Val Glu Pro Glu Thr Gly Asp Pro Val Thr Leu Arg Leu
            645                 650                 655 ctt gat gat gga gca ggt gct gat gtt ata aaa aat gat gga att tac    2135
Leu Asp Asp Gly Ala Gly Ala Asp Val Ile Lys Asn Asp Gly Ile Tyr
        660                 665                 670 tcg agg tat ttt ttc tcc ttt gct gca aat ggt aga tat agc ttg aaa    2183
Ser Arg Tyr Phe Phe Ser Phe Ala Ala Asn Gly Arg Tyr Ser Leu Lys
    675                 680                 685 gtg cat gtc aat cac tct ccc agc ata agc acc cca gcc cac tct att    2231
Val His Val Asn His Ser Pro Ser Ile Ser Thr Pro Ala His Ser Ile
690                 695                 700 cca ggg agt cat gct atg tat gta cca ggt tac aca gca aac ggt aat    2279
Pro Gly Ser His Ala Met Tyr Val Pro Gly Tyr Thr Ala Asn Gly Asn
705                 710                 715                 720 att cag atg aat gct cca agg aaa tca gta ggc aga aat gag gag gag    2327
Ile Gln Met Asn Ala Pro Arg Lys Ser Val Gly Arg Asn Glu Glu Glu
            725                 730                 735 cga aag tgg ggc ttt agc cga gtc agc tca gga ggc tcc ttt tca gtg    2375
Arg Lys Trp Gly Phe Ser Arg Val Ser Ser Gly Gly Ser Phe Ser Val
        740                 745                 750 ctg gga gtt cca gct ggc ccc cac cct gat gtg ttt cca cca tgc aaa    2423
Leu Gly Val Pro Ala Gly Pro His Pro Asp Val Phe Pro Pro Cys Lys
    755                 760                 765 att att gac ctg gaa gct gta aaa gta gaa gag gaa ttg acc cta tct    2471
Ile Ile Asp Leu Glu Ala Val Lys Val Glu Glu Glu Leu Thr Leu Ser
770                 775                 780 tgg aca gca cct gga gaa gac ttt gat cag ggc cag gct aca agc tat    2519
Trp Thr Ala Pro Gly Glu Asp Phe Asp Gln Gly Gln Ala Thr Ser Tyr
785                 790                 795                 800
```

```
gaa ata aga atg agt aaa agt cta cag aat atc caa gat gac ttt aac     2567
Glu Ile Arg Met Ser Lys Ser Leu Gln Asn Ile Gln Asp Asp Phe Asn
                805                 810                 815 aat gct att tta gta aat aca tca aag cga aat cct cag caa gct ggc     2615
Asn Ala Ile Leu Val Asn Thr Ser Lys Arg Asn Pro Gln Gln Ala Gly
            820                 825                 830 atc agg gag ata ttt acg ttc tca ccc cag att tcc acg aat gga cct     2663
Ile Arg Glu Ile Phe Thr Phe Ser Pro Gln Ile Ser Thr Asn Gly Pro
835                 840                 845 gaa cat cag cca aat gga gaa aca cat gaa agc cac aga att tat gtt     2711
Glu His Gln Pro Asn Gly Glu Thr His Glu Ser His Arg Ile Tyr Val
    850                 855                 860 gca ata cga gca atg gat agg aac tcc tta cag tct gct gta tct aac     2759
Ala Ile Arg Ala Met Asp Arg Asn Ser Leu Gln Ser Ala Val Ser Asn
865                 870                 875                 880 att gcc cag gcg cct ctg ttt att ccc ccc aat tct gat cct gta cct     2807
Ile Ala Gln Ala Pro Leu Phe Ile Pro Pro Asn Ser Asp Pro Val Pro
                885                 890                 895 gcc aga gat tat ctt ata ttg aaa gga gtt tta aca gca atg ggt ttg     2855
Ala Arg Asp Tyr Leu Ile Leu Lys Gly Val Leu Thr Ala Met Gly Leu
            900                 905                 910 ata gga atc att tgc ctt att ata gtt gtg aca cat cat act tta agc     2903
Ile Gly Ile Ile Cys Leu Ile Ile Val Val Thr His His Thr Leu Ser
        915                 920                 925 agg aaa aag aga gca gac aag aaa gag aat gga aca aaa tta tta          2948
Arg Lys Lys Arg Ala Asp Lys Lys Glu Asn Gly Thr Lys Leu Leu
930                 935                 940 taaataaata tccaaagtgt cttccttctt agatataaga cccatggcct tcgactacaa    3008
aaacatacta acaaagtcaa attaacatca aaactgtatt aaaatgcatt gagttttgta    3068
caatacagat aagattttta catggtagat caacaaattc ttttttggggg tagattagaa   3128 aaccttacac tttggctatg aacaaataat aaaaattatt ctttaaaaaa aaaaaaaaaa    3188
aa                                                                    3190

<210> SEQ ID NO 4
<211> LENGTH: 943
<212> TYPE: PRT
<213> ORGANISM: Homo sapiens

<400> SEQUENCE: 4

Met Thr Gln Arg Ser Ile Ala Gly Pro Ile Cys Asn Leu Lys Phe Val
 1               5                  10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Arg Ala His Gly Asp Asp Pro Tyr Thr Leu Gln
        115                 120                 125
```

-continued

```
Tyr Arg Gly Cys Gly Lys Glu Gly Lys Tyr Ile His Phe Thr Pro Asn
    130                 135                 140

Phe Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
        210                 215                 220

Gly Cys Thr Phe Ile Tyr Asn Ser Thr Gln Ser Ala Thr Ala Ser Ile
225                 230                 235                 240

Met Phe Met Arg Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Ala Ser Ser
305                 310                 315                 320

Lys Met Ala Glu Ala Asp Arg Leu Leu Gln Leu Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
```

```
                    545                 550                 555                 560
             Thr Ala Ser Leu Trp Ile Pro Gly Thr Ala Lys Pro Gly His Trp Thr
                             565                 570                 575

Tyr Thr Leu Asn Asn Thr His His Ser Leu Gln Ala Leu Lys Val Thr
                         580                 585                 590

Val Thr Ser Arg Ala Ser Asn Ser Ala Val Pro Pro Ala Thr Val Glu
                         595                 600                 605

Ala Phe Val Glu Arg Asp Ser Leu His Phe Pro His Pro Val Met Ile
                     610                 615                 620

Tyr Ala Asn Val Lys Gln Gly Phe Tyr Pro Ile Leu Asn Ala Thr Val
                 625                 630                 635                 640

Thr Ala Thr Val Glu Pro Glu Thr Gly Asp Pro Val Thr Leu Arg Leu
                             645                 650                 655

Leu Asp Asp Gly Ala Gly Ala Asp Val Ile Lys Asn Asp Gly Ile Tyr
                         660                 665                 670

Ser Arg Tyr Phe Phe Ser Phe Ala Ala Asn Gly Arg Tyr Ser Leu Lys
                         675                 680                 685

Val His Val Asn His Ser Pro Ser Ile Ser Thr Pro Ala His Ser Ile
                     690                 695                 700

Pro Gly Ser His Ala Met Tyr Val Pro Gly Tyr Thr Ala Asn Gly Asn
                 705                 710                 715                 720

Ile Gln Met Asn Ala Pro Arg Lys Ser Val Gly Arg Asn Glu Glu Glu
                             725                 730                 735

Arg Lys Trp Gly Phe Ser Arg Val Ser Ser Gly Gly Ser Phe Ser Val
                         740                 745                 750

Leu Gly Val Pro Ala Gly Pro His Pro Asp Val Phe Pro Pro Cys Lys
                         755                 760                 765

Ile Ile Asp Leu Glu Ala Val Lys Val Glu Glu Leu Thr Leu Ser
                     770                 775                 780

Trp Thr Ala Pro Gly Glu Asp Phe Asp Gln Gly Gln Ala Thr Ser Tyr
             785                 790                 795                 800

Glu Ile Arg Met Ser Lys Ser Leu Gln Asn Ile Gln Asp Asp Phe Asn
                             805                 810                 815

Asn Ala Ile Leu Val Asn Thr Ser Lys Arg Asn Pro Gln Gln Ala Gly
                         820                 825                 830

Ile Arg Glu Ile Phe Thr Phe Ser Pro Gln Ile Ser Thr Asn Gly Pro
                         835                 840                 845

Glu His Gln Pro Asn Gly Glu Thr His Glu Ser His Arg Ile Tyr Val
                     850                 855                 860

Ala Ile Arg Ala Met Asp Arg Asn Ser Leu Gln Ser Ala Val Ser Asn
             865                 870                 875                 880

Ile Ala Gln Ala Pro Leu Phe Ile Pro Pro Asn Ser Asp Pro Val Pro
                             885                 890                 895

Ala Arg Asp Tyr Leu Ile Leu Lys Gly Val Leu Thr Ala Met Gly Leu
                         900                 905                 910

Ile Gly Ile Ile Cys Leu Ile Ile Val Val Thr His Thr Leu Ser
                         915                 920                 925

Arg Lys Lys Arg Ala Asp Lys Lys Glu Asn Gly Thr Lys Leu Leu
                 930                 935                 940

<210> SEQ ID NO 5
<211> LENGTH: 2745
<212> TYPE: DNA
<213> ORGANISM: Homo sapiens
```

```
<220> FEATURE:
<221> NAME/KEY: CDS
<222> LOCATION: (1)..(2742)

<400> SEQUENCE: 5 atg ggg cca ttt aag agt tct gtg ttc atc ttg att ctt cac ctt cta      48
Met Gly Pro Phe Lys Ser Ser Val Phe Ile Leu Ile Leu His Leu Leu
 1               5                  10                  15 gaa ggg gcc ctg agt aat tca ctc att cag ctg aac aac aat ggc tat      96
Glu Gly Ala Leu Ser Asn Ser Leu Ile Gln Leu Asn Asn Asn Gly Tyr
             20                  25                  30 gaa ggc att gtc gtt gca atc gac ccc aat gtg cca gaa gat gaa aca     144
Glu Gly Ile Val Val Ala Ile Asp Pro Asn Val Pro Glu Asp Glu Thr
         35                  40                  45 ctc att caa caa ata aag gac atg gtg acc cag gca tct ctg tat ctg     192
Leu Ile Gln Gln Ile Lys Asp Met Val Thr Gln Ala Ser Leu Tyr Leu
     50                  55                  60 ttt gaa gct aca gga aag cga ttt tat ttc aaa aat gtt gcc att ttg     240
Phe Glu Ala Thr Gly Lys Arg Phe Tyr Phe Lys Asn Val Ala Ile Leu
 65                  70                  75                  80 att cct gaa aca tgg aag aca aag gct gac tat gtg aga cca aaa ctt     288
Ile Pro Glu Thr Trp Lys Thr Lys Ala Asp Tyr Val Arg Pro Lys Leu
                 85                  90                  95 gag acc tac aaa aat gct gat gtt ctg gtt gct gag tct act cct cca     336
Glu Thr Tyr Lys Asn Ala Asp Val Leu Val Ala Glu Ser Thr Pro Pro
            100                 105                 110 ggt aat gat gaa ccc tac act gag cag atg ggc aac tgt gga gag aag     384
Gly Asn Asp Glu Pro Tyr Thr Glu Gln Met Gly Asn Cys Gly Glu Lys
        115                 120                 125 ggt gaa agg atc cac ctc act cct gat ttc att gca gga aaa aag tta     432
Gly Glu Arg Ile His Leu Thr Pro Asp Phe Ile Ala Gly Lys Lys Leu
    130                 135                 140 gct gaa tat gga cca caa ggt agg gca ttt gtc cat gag tgg gct cat     480
Ala Glu Tyr Gly Pro Gln Gly Arg Ala Phe Val His Glu Trp Ala His
145                 150                 155                 160 cta cga tgg gga gta ttt gac gag tac aat aat gat gag aaa ttc tac     528
Leu Arg Trp Gly Val Phe Asp Glu Tyr Asn Asn Asp Glu Lys Phe Tyr
                165                 170                 175 tta tcc aat gga aga ata caa gca gta aga tgt tca gca ggt att act     576
Leu Ser Asn Gly Arg Ile Gln Ala Val Arg Cys Ser Ala Gly Ile Thr
            180                 185                 190 ggt aca aat gta gta aag aag tgt cag gga ggc agc tgt tac acc aaa     624
Gly Thr Asn Val Val Lys Lys Cys Gln Gly Gly Ser Cys Tyr Thr Lys
        195                 200                 205 aga tgc aca ttc aat aaa gtw aca gga ctc tat gaa aaa gga tgt gag     672
Arg Cys Thr Phe Asn Lys Xaa Thr Gly Leu Tyr Glu Lys Gly Cys Glu
    210                 215                 220 ttt gtt ctc caa tcc cgc cag acg gag aag gct tct ata atg ttt gca     720
Phe Val Leu Gln Ser Arg Gln Thr Glu Lys Ala Ser Ile Met Phe Ala
225                 230                 235                 240 caa cat gtt gat tct ata gtt gaa ttc tgt aca gaa caa aac cac aac     768
Gln His Val Asp Ser Ile Val Glu Phe Cys Thr Glu Gln Asn His Asn
                245                 250                 255 aaa gaa gct cca aac aag caa aat caa aaa tgc aat ctc cga agc aca     816
Lys Glu Ala Pro Asn Lys Gln Asn Gln Lys Cys Asn Leu Arg Ser Thr
            260                 265                 270 tgg gaa gtg atc cgt gat tct gag gac ttt aag aaa acc act cct atg     864
Trp Glu Val Ile Arg Asp Ser Glu Asp Phe Lys Lys Thr Thr Pro Met
        275                 280                 285 aca aca cag cca cca aat ccc acc ttc tca ttg ctg cag att gga caa     912
```

```
Thr Thr Gln Pro Pro Asn Pro Thr Phe Ser Leu Leu Gln Ile Gly Gln
        290                 295                 300 aga att gtg tgt tta gtc ctt gac aaa tct gga agc atg gcg act ggt        960
Arg Ile Val Cys Leu Val Leu Asp Lys Ser Gly Ser Met Ala Thr Gly
305                 310                 315                 320 aac cgc ctc aat cga ctg aat caa gca ggc cag ctt ttc ctg ctg cag       1008
Asn Arg Leu Asn Arg Leu Asn Gln Ala Gly Gln Leu Phe Leu Leu Gln
                325                 330                 335 aca gtt gag ctg ggg tcc tgg gtt ggg atg gtg aca ttt gac agt gct       1056
Thr Val Glu Leu Gly Ser Trp Val Gly Met Val Thr Phe Asp Ser Ala
        340                 345                 350 gcc cat gta caa agt gaa ctc ata cag ata aac agt ggc agt gac agg       1104
Ala His Val Gln Ser Glu Leu Ile Gln Ile Asn Ser Gly Ser Asp Arg
    355                 360                 365 gac aca ctc gcc aaa aga tta cct gca gca gct tca gga ggg acg tcc       1152
Asp Thr Leu Ala Lys Arg Leu Pro Ala Ala Ala Ser Gly Gly Thr Ser
370                 375                 380 atc tgc agc ggg ctt cga tcg gca ttt act gtg att agg aag aaa tat       1200
Ile Cys Ser Gly Leu Arg Ser Ala Phe Thr Val Ile Arg Lys Lys Tyr
385                 390                 395                 400 cca act gat gga tct gaa att gtg ctg ctg acg gat ggg gaa gac aac       1248
Pro Thr Asp Gly Ser Glu Ile Val Leu Leu Thr Asp Gly Glu Asp Asn
                405                 410                 415 act ata agt ggg tgc ttt aac gag gtc aaa caa agt ggt gcc atc atc       1296
Thr Ile Ser Gly Cys Phe Asn Glu Val Lys Gln Ser Gly Ala Ile Ile
        420                 425                 430 cac aca gtc gct ttg ggg ccc tct gca gct caa gaa cta gag gag ctg       1344
His Thr Val Ala Leu Gly Pro Ser Ala Ala Gln Glu Leu Glu Glu Leu
    435                 440                 445 tcc aaa atg aca gga ggt tta cag aca tat gct tca gat caa gtt cag       1392
Ser Lys Met Thr Gly Gly Leu Gln Thr Tyr Ala Ser Asp Gln Val Gln
450                 455                 460 aac aat ggc ctc att gat gct ttt ggg gcc ctt tca tca gga aat gga       1440
Asn Asn Gly Leu Ile Asp Ala Phe Gly Ala Leu Ser Ser Gly Asn Gly
465                 470                 475                 480 gct gtc tct cag cgc tcc atc cag ctt gag agt aag gga tta acc ctc       1488
Ala Val Ser Gln Arg Ser Ile Gln Leu Glu Ser Lys Gly Leu Thr Leu
                485                 490                 495 cag aac agc cag tgg atg aat ggc aca gtg atc gtg gac agc acc gtg       1536
Gln Asn Ser Gln Trp Met Asn Gly Thr Val Ile Val Asp Ser Thr Val
        500                 505                 510 gga aag gac act ttg ttt ctt atc acc tgg aca acg cag cct ccc caa       1584
Gly Lys Asp Thr Leu Phe Leu Ile Thr Trp Thr Thr Gln Pro Pro Gln
    515                 520                 525 atc ctt ctc tgg gat ccc agt gga cag aag caa ggt ggc ttt gta gtg       1632
Ile Leu Leu Trp Asp Pro Ser Gly Gln Lys Gln Gly Gly Phe Val Val
530                 535                 540 gac aaa aac acc aaa atg gcc tac ctc caa atc cca ggc att gct aag       1680
Asp Lys Asn Thr Lys Met Ala Tyr Leu Gln Ile Pro Gly Ile Ala Lys
545                 550                 555                 560 gtt ggc act tgg aaa tac agt ctg caa gca agc tca caa acc ttg acc       1728
Val Gly Thr Trp Lys Tyr Ser Leu Gln Ala Ser Ser Gln Thr Leu Thr
                565                 570                 575 ctg act gtc acg tcc cgt gcg tcc aat gct acc ctg cct cca att aca       1776
Leu Thr Val Thr Ser Arg Ala Ser Asn Ala Thr Leu Pro Pro Ile Thr
        580                 585                 590 gtg act tcc aaa acg aac aag gac acc agc aaa ttc ccc agc cct ctg       1824
Val Thr Ser Lys Thr Asn Lys Asp Thr Ser Lys Phe Pro Ser Pro Leu
    595                 600                 605
```

```
gta gtt tat gca aat att cgc caa gga gcc tcc cca att ctc agg gcc    1872
Val Val Tyr Ala Asn Ile Arg Gln Gly Ala Ser Pro Ile Leu Arg Ala
610                 615                 620 agt gtc aca gcc ctg att gaa tca gtg aat gga aaa aca gtt acc ttg    1920
Ser Val Thr Ala Leu Ile Glu Ser Val Asn Gly Lys Thr Val Thr Leu
625                 630                 635                 640 gaa cta ctg gat aat gga gca ggt gct gat gct act aag gat gac ggt    1968
Glu Leu Leu Asp Asn Gly Ala Gly Ala Asp Ala Thr Lys Asp Asp Gly
                645                 650                 655 gtc tac tca agg tat ttc aca act tat gac acg aat ggt aga tac agt    2016
Val Tyr Ser Arg Tyr Phe Thr Thr Tyr Asp Thr Asn Gly Arg Tyr Ser
            660                 665                 670 gta aaa gtg cgg gct ctg gga gga gtt aac gca gcc aga cgg aga gtg    2064
Val Lys Val Arg Ala Leu Gly Gly Val Asn Ala Ala Arg Arg Arg Val
        675                 680                 685 ata ccc cag cag agt gga gca ctg tac ata cct ggc tgg att gag aat    2112
Ile Pro Gln Gln Ser Gly Ala Leu Tyr Ile Pro Gly Trp Ile Glu Asn
    690                 695                 700 gat gaa atc caa tgg aat cca cca aga cct gaa att aat aag gat gat    2160
Asp Glu Ile Gln Trp Asn Pro Pro Arg Pro Glu Ile Asn Lys Asp Asp
705                 710                 715                 720 gtt caa cac aag caa gtg tgt ttc agc aga aca tcc tcg gga ggc tca    2208
Val Gln His Lys Gln Val Cys Phe Ser Arg Thr Ser Ser Gly Gly Ser
                725                 730                 735 ttt gtg gct tct gat gtc cca aat gct ccc ata cct gat ctc ttc cca    2256
Phe Val Ala Ser Asp Val Pro Asn Ala Pro Ile Pro Asp Leu Phe Pro
                740                 745                 750 cct ggc caa atc acc gac ctg aag gcg gaa att cac ggg ggc agt ctc    2304
Pro Gly Gln Ile Thr Asp Leu Lys Ala Glu Ile His Gly Gly Ser Leu
            755                 760                 765 att aat ctg act tgg aca gct cct ggg gat gat tat gac cat gga aca    2352
Ile Asn Leu Thr Trp Thr Ala Pro Gly Asp Asp Tyr Asp His Gly Thr
770                 775                 780 gct cac aag tat atc att cga ata agt aca agt att ctt gat ctc aga    2400
Ala His Lys Tyr Ile Ile Arg Ile Ser Thr Ser Ile Leu Asp Leu Arg
785                 790                 795                 800 gac aag ttc aat gaa tct ctt caa gtg aat act act gct ctc atc cca    2448
Asp Lys Phe Asn Glu Ser Leu Gln Val Asn Thr Thr Ala Leu Ile Pro
                805                 810                 815 aag gaa gcc aac tct gag gaa gtc ttt ttg ttt aaa cca gaa aac att    2496
Lys Glu Ala Asn Ser Glu Glu Val Phe Leu Phe Lys Pro Glu Asn Ile
            820                 825                 830 act ttt gaa aat ggc aca gat ctt ttc att gct att cag gct gtt gat    2544
Thr Phe Glu Asn Gly Thr Asp Leu Phe Ile Ala Ile Gln Ala Val Asp
        835                 840                 845 aag gtc gat ctg aaa tca gaa ata tcc aac att gca cga gta tct ttg    2592
Lys Val Asp Leu Lys Ser Glu Ile Ser Asn Ile Ala Arg Val Ser Leu
850                 855                 860 ttt att cct cca cag act ccg cca gag aca cct agt cct gat gaa acg    2640
Phe Ile Pro Pro Gln Thr Pro Pro Glu Thr Pro Ser Pro Asp Glu Thr
865                 870                 875                 880 tct gct cct tgt cct aat att cat atc aac agc acc att cct ggc att    2688
Ser Ala Pro Cys Pro Asn Ile His Ile Asn Ser Thr Ile Pro Gly Ile
                885                 890                 895 cac att tta aaa att atg tgg aag tgg ata gga gaa ctg cag ctg tca    2736
His Ile Leu Lys Ile Met Trp Lys Trp Ile Gly Glu Leu Gln Leu Ser
            900                 905                 910 ata gcc tag                                                        2745
Ile Ala
```

```
<210> SEQ ID NO 6
<211> LENGTH: 914
<212> TYPE: PRT
<213> ORGANISM: Homo sapiens

<400> SEQUENCE: 6
```

Met Gly Pro Phe Lys Ser Ser Val Phe Ile Leu Ile Leu His Leu Leu
 1               5                  10                  15

Glu Gly Ala Leu Ser Asn Ser Leu Ile Gln Leu Asn Asn Asn Gly Tyr
            20                  25                  30

Glu Gly Ile Val Val Ala Ile Asp Pro Asn Val Pro Glu Asp Glu Thr
        35                  40                  45

Leu Ile Gln Gln Ile Lys Asp Met Val Thr Gln Ala Ser Leu Tyr Leu
    50                  55                  60

Phe Glu Ala Thr Gly Lys Arg Phe Tyr Phe Lys Asn Val Ala Ile Leu
65                  70                  75                  80

Ile Pro Glu Thr Trp Lys Thr Lys Ala Asp Tyr Val Arg Pro Lys Leu
                85                  90                  95

Glu Thr Tyr Lys Asn Ala Asp Val Leu Val Ala Glu Ser Thr Pro Pro
            100                 105                 110

Gly Asn Asp Glu Pro Tyr Thr Glu Gln Met Gly Asn Cys Gly Glu Lys
        115                 120                 125

Gly Glu Arg Ile His Leu Thr Pro Asp Phe Ile Ala Gly Lys Lys Leu
    130                 135                 140

Ala Glu Tyr Gly Pro Gln Gly Arg Ala Phe Val His Glu Trp Ala His
145                 150                 155                 160

Leu Arg Trp Gly Val Phe Asp Glu Tyr Asn Asn Asp Glu Lys Phe Tyr
                165                 170                 175

Leu Ser Asn Gly Arg Ile Gln Ala Val Arg Cys Ser Ala Gly Ile Thr
            180                 185                 190

Gly Thr Asn Val Val Lys Lys Cys Gln Gly Gly Ser Cys Tyr Thr Lys
        195                 200                 205

Arg Cys Thr Phe Asn Lys Xaa Thr Gly Leu Tyr Glu Lys Gly Cys Glu
    210                 215                 220

Phe Val Leu Gln Ser Arg Gln Thr Glu Lys Ala Ser Ile Met Phe Ala
225                 230                 235                 240

Gln His Val Asp Ser Ile Val Glu Phe Cys Thr Glu Gln Asn His Asn
                245                 250                 255

Lys Glu Ala Pro Asn Lys Gln Asn Gln Lys Cys Asn Leu Arg Ser Thr
            260                 265                 270

Trp Glu Val Ile Arg Asp Ser Glu Asp Phe Lys Lys Thr Thr Pro Met
        275                 280                 285

Thr Thr Gln Pro Pro Asn Pro Thr Phe Ser Leu Leu Gln Ile Gly Gln
    290                 295                 300

Arg Ile Val Cys Leu Val Leu Asp Lys Ser Gly Ser Met Ala Thr Gly
305                 310                 315                 320

Asn Arg Leu Asn Arg Leu Asn Gln Ala Gly Gln Leu Phe Leu Leu Gln
                325                 330                 335

Thr Val Glu Leu Gly Ser Trp Val Gly Met Val Thr Phe Asp Ser Ala
            340                 345                 350

Ala His Val Gln Ser Glu Leu Ile Gln Ile Asn Ser Gly Ser Asp Arg
        355                 360                 365

Asp Thr Leu Ala Lys Arg Leu Pro Ala Ala Ala Ser Gly Gly Thr Ser
    370                 375                 380

-continued

```
Ile Cys Ser Gly Leu Arg Ser Ala Phe Thr Val Ile Arg Lys Lys Tyr
385                 390                 395                 400

Pro Thr Asp Gly Ser Glu Ile Val Leu Leu Thr Asp Gly Glu Asp Asn
                405                 410                 415

Thr Ile Ser Gly Cys Phe Asn Glu Val Lys Gln Ser Gly Ala Ile Ile
                420                 425                 430

His Thr Val Ala Leu Gly Pro Ser Ala Gln Glu Leu Glu Glu Leu
                435                 440                 445

Ser Lys Met Thr Gly Gly Leu Gln Thr Tyr Ala Ser Asp Gln Val Gln
450                 455                 460

Asn Asn Gly Leu Ile Asp Ala Phe Gly Ala Leu Ser Ser Gly Asn Gly
465                 470                 475                 480

Ala Val Ser Gln Arg Ser Ile Gln Leu Glu Ser Lys Gly Leu Thr Leu
                485                 490                 495

Gln Asn Ser Gln Trp Met Asn Gly Thr Val Ile Val Asp Ser Thr Val
                500                 505                 510

Gly Lys Asp Thr Leu Phe Leu Ile Thr Trp Thr Thr Gln Pro Pro Gln
                515                 520                 525

Ile Leu Leu Trp Asp Pro Ser Gly Gln Lys Gln Gly Gly Phe Val Val
530                 535                 540

Asp Lys Asn Thr Lys Met Ala Tyr Leu Gln Ile Pro Gly Ile Ala Lys
545                 550                 555                 560

Val Gly Thr Trp Lys Tyr Ser Leu Gln Ala Ser Ser Gln Thr Leu Thr
                565                 570                 575

Leu Thr Val Thr Ser Arg Ala Ser Asn Ala Thr Leu Pro Pro Ile Thr
                580                 585                 590

Val Thr Ser Lys Thr Asn Lys Asp Thr Ser Lys Phe Pro Ser Pro Leu
                595                 600                 605

Val Val Tyr Ala Asn Ile Arg Gln Gly Ala Ser Pro Ile Leu Arg Ala
                610                 615                 620

Ser Val Thr Ala Leu Ile Glu Ser Val Asn Gly Lys Thr Val Thr Leu
625                 630                 635                 640

Glu Leu Leu Asp Asn Gly Ala Gly Ala Asp Ala Thr Lys Asp Asp Gly
                645                 650                 655

Val Tyr Ser Arg Tyr Phe Thr Thr Tyr Asp Thr Asn Gly Arg Tyr Ser
                660                 665                 670

Val Lys Val Arg Ala Leu Gly Gly Val Asn Ala Ala Arg Arg Arg Val
                675                 680                 685

Ile Pro Gln Gln Ser Gly Ala Leu Tyr Ile Pro Gly Trp Ile Glu Asn
690                 695                 700

Asp Glu Ile Gln Trp Asn Pro Pro Arg Pro Glu Ile Asn Lys Asp Asp
705                 710                 715                 720

Val Gln His Lys Gln Val Cys Phe Ser Arg Thr Ser Ser Gly Gly Ser
                725                 730                 735

Phe Val Ala Ser Asp Val Pro Asn Ala Pro Ile Pro Asp Leu Phe Pro
                740                 745                 750

Pro Gly Gln Ile Thr Asp Leu Lys Ala Glu Ile His Gly Gly Ser Leu
                755                 760                 765

Ile Asn Leu Thr Trp Thr Ala Pro Gly Asp Asp Tyr Asp His Gly Thr
                770                 775                 780

Ala His Lys Tyr Ile Ile Arg Ile Ser Thr Ser Ile Leu Asp Leu Arg
785                 790                 795                 800
```

-continued

Asp Lys Phe Asn Glu Ser Leu Gln Val Asn Thr Thr Ala Leu Ile Pro
            805                 810                 815

Lys Glu Ala Asn Ser Glu Glu Val Phe Leu Phe Lys Pro Glu Asn Ile
        820                 825                 830

Thr Phe Glu Asn Gly Thr Asp Leu Phe Ile Ala Ile Gln Ala Val Asp
        835                 840                 845

Lys Val Asp Leu Lys Ser Glu Ile Ser Asn Ile Ala Arg Val Ser Leu
    850                 855                 860

Phe Ile Pro Pro Gln Thr Pro Pro Glu Thr Pro Ser Pro Asp Glu Thr
865                 870                 875                 880

Ser Ala Pro Cys Pro Asn Ile His Ile Asn Ser Thr Ile Pro Gly Ile
            885                 890                 895

His Ile Leu Lys Ile Met Trp Lys Trp Ile Gly Glu Leu Gln Leu Ser
            900                 905                 910

Ile Ala

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: sense
      primer for mouse ICACC-1 RNA

<400> SEQUENCE: 7
ccagatccac accaaaacga gaag                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: anti-sense
      primer for mouse ICACC-1 RNA

<400> SEQUENCE: 8
cactgtcaaa ggtcaccatc ccga                                          24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: sense
      primer for human ICACC-1 RNA

<400> SEQUENCE: 9
gattccagga acagctaagc                                               20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: anti-sense
      primer for human ICACC-1 RNA

<400> SEQUENCE: 10
tatttcatag cttgtagcct gg                                            22

<210> SEQ ID NO 11
<211> LENGTH: 21
<212> TYPE: DNA

```
<213> ORGANISM: Artificial Sequence
<220> FEATURE:
<223> OTHER INFORMATION: Description of Artificial Sequence:  PCR 5'
      primer for ICACC-1

<400> SEQUENCE: 11
cccaaaggaa gccaactctg a                                            21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:  PCR 3'
      primer for ICACC-1

<400> SEQUENCE: 12
gtgaatgcca ggaatggtgc t                                            21

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence:  peptide
      for immunization to mICACC-1

<400> SEQUENCE: 13

Cys Leu Val Leu Asp Lys Ser Gly Ser Met Leu Asn Asp Asp Arg Leu
  1               5                  10                  15

Asn Arg Met Asn Gln Ala
             20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence:  peptide
      for immunization to mICACC-1

<400> SEQUENCE: 14

Gln Ser Glu Leu Lys Gln Leu Asn Ser Gly Ala Asp Arg Asp Leu Leu
  1               5                  10                  15

Ile Lys His Cys
             20

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence:  peptide
      for immunization to mICACC-1

<400> SEQUENCE: 15

Lys Lys Lys Tyr Pro Thr Asp Gly Ser Glu Ile Val Leu Leu Thr Asp
  1               5                  10                  15

Gly Glu Asp Asn Thr Ile Ser Ser Cys
             20                  25

<210> SEQ ID NO 16
<211> LENGTH: 24
<212> TYPE: PRT
<213> ORGANISM: Artificial Sequence
<220> FEATURE:
```

```
<223> OTHER INFORMATION: Description of Artificial Sequence: peptide
      for immunization to mICACC-1

<400> SEQUENCE: 16

Thr Thr His Pro Pro Thr Ile Phe Ile Trp Asp Pro Ser Gly Val Glu
  1               5                  10                  15

Gln Asn Gly Phe Ile Leu Asp Cys
             20

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: peptide
      for immunization to mICACC-1

<400> SEQUENCE: 17

Cys Pro Pro Ile Thr Val Thr Pro Val Val Asn Lys Asn Thr Gly Lys
  1               5                  10                  15

Phe Pro Ser Pro Val Thr
             20

<210> SEQ ID NO 18
<211> LENGTH: 903
<212> TYPE: PRT
<213> ORGANISM: Bos taurus

<400> SEQUENCE: 18

Met Val Pro Arg Leu Thr Val Ile Leu Phe Leu Thr Leu His Leu Leu
  1               5                  10                  15

Pro Gly Met Lys Ser Ser Met Val Asn Leu Ile Asn Asn Gly Tyr Asp
             20                  25                  30

Gly Ile Val Ile Ala Ile Asn Pro Ser Val Pro Glu Asp Glu Lys Leu
         35                  40                  45

Ile Gln Asn Ile Lys Glu Met Val Thr Glu Ala Ser Thr Tyr Leu Phe
     50                  55                  60

His Ala Thr Lys Arg Arg Val Tyr Phe Arg Asn Val Ser Ile Leu Ile
 65                  70                  75                  80

Pro Met Thr Trp Lys Ser Lys Ser Glu Tyr Leu Met Pro Lys Gln Glu
                 85                  90                  95

Ser Tyr Asp Gln Ala Glu Val Val Ala Asn Pro Tyr Leu Lys His
             100                 105                 110

Gly Asp Asp Pro Tyr Thr Leu Gln Tyr Gly Arg Cys Gly Glu Lys Gly
         115                 120                 125

Gln Tyr Ile His Phe Thr Pro Asn Phe Leu Leu Thr Asn Asn Leu Pro
    130                 135                 140

Ile Tyr Gly Ser Arg Gly Arg Ala Phe Val His Glu Trp Ala His Leu
145                 150                 155                 160

Arg Trp Gly Ile Phe Asp Glu Tyr Asn Gly Asp Gln Pro Phe Tyr Ile
                165                 170                 175

Ser Arg Arg Asn Thr Ile Glu Ala Thr Arg Cys Ser Thr His Ile Thr
            180                 185                 190

Gly Thr Asn Val Ile Val Lys Cys Gln Gly Gly Ser Cys Ile Thr Arg
        195                 200                 205

Pro Cys Arg Arg Asp Ser Gln Thr Gly Leu Tyr Glu Ala Lys Cys Thr
    210                 215                 220

Phe Ile Pro Glu Lys Ser Gln Thr Ala Arg Glu Ser Ile Met Phe Met
```

-continued

```
                225                 230                 235                 240
            Gln Ser Leu His Ser Val Thr Glu Phe Cys Thr Glu Lys Thr His Asn
                                245                 250                 255
            Val Glu Ala Pro Asn Leu Gln Asn Lys Met Cys Asn Gly Lys Ser Thr
                                260                 265                 270
            Trp Asp Val Ile Met Asn Ser Thr Asp Phe Gln Asn Thr Ser Pro Met
                    275                 280                 285
            Thr Glu Met Asn Pro Pro Thr Gln Pro Thr Phe Ser Leu Leu Lys Ser
                    290                 295                 300
            Lys Gln Arg Val Val Cys Leu Val Leu Asp Lys Ser Gly Ser Met Ser
            305                 310                 315                 320
            Ser Glu Asp Arg Leu Phe Arg Met Asn Gln Ala Ala Glu Leu Phe Leu
                                325                 330                 335
            Ile Gln Ile Ile Glu Lys Gly Ser Leu Val Gly Met Val Thr Phe Asp
                                340                 345                 350
            Ser Val Ala Glu Ile Arg Asn Asn Leu Thr Lys Ile Thr Asp Asp Asn
                    355                 360                 365
            Val Tyr Glu Asn Ile Thr Ala Asn Leu Pro Gln Glu Ala Asn Gly Gly
                    370                 375                 380
            Thr Ser Ile Cys Arg Gly Leu Lys Ala Gly Phe Gln Ala Ile Ile Gln
            385                 390                 395                 400
            Ser Gln Gln Ser Thr Ser Gly Ser Glu Ile Ile Leu Leu Thr Asp Gly
                                405                 410                 415
            Glu Asp Asn Glu Ile His Ser Cys Ile Glu Val Lys Gln Ser Gly
                                420                 425                 430
            Val Ile Ile His Thr Ile Ala Leu Gly Pro Ser Ala Ala Lys Glu Leu
                    435                 440                 445
            Glu Thr Leu Ser Asp Met Thr Gly Gly His Arg Phe Tyr Ala Asn Lys
                    450                 455                 460
            Asp Ile Asn Gly Leu Thr Asn Ala Phe Ser Arg Ile Ser Ser Arg Ser
            465                 470                 475                 480
            Gly Ser Ile Thr Gln Gln Thr Ile Gln Leu Glu Ser Lys Ala Leu Ala
                                485                 490                 495
            Ile Thr Glu Lys Lys Trp Val Asn Gly Thr Val Pro Val Asp Ser Thr
                                500                 505                 510
            Ile Gly Asn Asp Thr Phe Phe Val Val Thr Trp Thr Ile Lys Lys Pro
                    515                 520                 525
            Glu Ile Leu Leu Gln Asp Pro Lys Gly Lys Lys Tyr Lys Thr Ser Asp
                    530                 535                 540
            Phe Lys Glu Asp Lys Leu Asn Ile His Ser Ala Arg Leu Arg Ile Pro
            545                 550                 555                 560
            Gly Ile Ala Glu Thr Gly Thr Trp Thr Tyr Ser Leu Leu Asn Asn His
                                565                 570                 575
            Ala Ser Pro Gln Ile Leu Thr Val Thr Val Thr Thr Arg Ala Arg Ser
                                580                 585                 590
            Pro Thr Thr Pro Pro Val Thr Ala Thr His Met Ser Gln Asn Thr
                    595                 600                 605
            Ala His Tyr Pro Ser Pro Val Ile Val Tyr Ala Gln Val Ser Gln Gly
                    610                 615                 620
            Phe Leu Pro Val Leu Gly Ile Asn Val Thr Ala Ile Ile Glu Thr Glu
            625                 630                 635                 640
            Asp Gly His Gln Val Thr Leu Glu Leu Trp Asp Asn Gly Ala Gly Ala
                                645                 650                 655
```

```
Asp Thr Val Lys Asn Asp Gly Ile Tyr Ser Arg Tyr Phe Thr Asp Tyr
            660                 665                 670

Arg Gly Asn Gly Arg Tyr Ser Leu Lys Val His Ala Glu Ala Arg Asn
        675                 680                 685

Asn Thr Ala Arg Leu Ser Leu Arg Gln Pro Gln Asn Lys Ala Leu Tyr
        690                 695                 700

Ile Pro Gly Tyr Ile Glu Asn Gly Lys Ile Ile Leu Asn Pro Pro Arg
705                 710                 715                 720

Pro Glu Val Lys Asp Asp Leu Ala Lys Ala Glu Ile Glu Asp Phe Ser
                725                 730                 735

Arg Leu Thr Ser Gly Gly Ser Phe Thr Val Ser Gly Ala Pro Pro Gly
            740                 745                 750

Asn His Pro Ser Val Leu Pro Pro Asn Lys Ile Ile Asp Leu Glu Ala
            755                 760                 765

Lys Phe Lys Glu Asp His Ile Gln Leu Ser Trp Thr Ala Pro Ala Asn
            770                 775                 780

Val Leu Asp Lys Gly Lys Ala Asn Ser Tyr Ile Ile Arg Ile Ser Lys
785                 790                 795                 800

Ser Phe Leu Asp Leu Gln Lys Asp Phe Asp Asn Ala Thr Leu Val Asn
                805                 810                 815

Thr Ser Ser Leu Lys Pro Lys Glu Ala Gly Ser Asp Glu Asn Phe Glu
                820                 825                 830

Phe Lys Pro Glu Pro Phe Arg Ile Glu Asn Gly Thr Asn Phe Tyr Ile
            835                 840                 845

Ala Val Gln Ala Ile Asn Glu Ala Asn Leu Thr Ser Glu Val Ser Asn
    850                 855                 860

Ile Ala Gln Ala Ile Lys Phe Ile Pro Met Pro Glu Asp Ser Val Pro
865                 870                 875                 880

Ala Leu Gly Thr Lys Ile Ser Ala Ile Asn Leu Ala Ile Phe Ala Leu
            885                 890                 895

Ala Met Ile Leu Ser Ile Val
            900
```